(12) United States Patent
Hayoz et al.

(10) Patent No.: US 10,793,668 B2
(45) Date of Patent: Oct. 6, 2020

(54) NAPHTHOINDACENODITHIOPHENES AND POLYMERS

(71) Applicant: CLAP Co., Ltd., Seoul (KR)

(72) Inventors: Pascal Hayoz, Hofstetten (CH); Daniel Kaelblein, Speyer (DE); Iain McCulloch, Eastleigh (GB); Astrid-Caroline Knall, Graz (AT)

(73) Assignee: CLAP Co., Ltd., Seoul (KR)

( * ) Notice: Subject to any disclaimer, the term of this patent is extended or adjusted under 35 U.S.C. 154(b) by 0 days.

(21) Appl. No.: 16/060,728

(22) PCT Filed: Dec. 8, 2016

(86) PCT No.: PCT/EP2016/080309
§ 371 (c)(1),
(2) Date: Jun. 8, 2018

(87) PCT Pub. No.: WO2017/097924
PCT Pub. Date: Jun. 15, 2017

(65) Prior Publication Data
US 2018/0362704 A1 Dec. 20, 2018

(30) Foreign Application Priority Data
Dec. 10, 2015 (EP) ..................................... 15199279

(51) Int. Cl.
*C08G 61/12* (2006.01)
*C07D 495/04* (2006.01)
(Continued)

(52) U.S. Cl.
CPC ......... *C08G 61/126* (2013.01); *C07D 495/04* (2013.01); *C08G 61/123* (2013.01);
(Continued)

(58) Field of Classification Search
CPC ...... C08G 2261/3223; C08G 2261/126; C08G 2261/124; C08G 2261/95; C08G 2261/91;
(Continued)

(56) References Cited

U.S. PATENT DOCUMENTS 9,796,811 B2  10/2017  Kashiki et al.
2012/0184089 A1  7/2012  Zuberi et al.
2015/0333263 A1  11/2015  D'Iavari et al.

FOREIGN PATENT DOCUMENTS

GB  2472413 A  2/2011
JP  2010-177642 A  8/2010
(Continued)

OTHER PUBLICATIONS

International Search Report and Written Opinion of the International Searching Authority dated Mar. 3, 2017 in PCT/EP2016/080309 filed Dec. 8, 2016, 10 pages.
(Continued)

*Primary Examiner* — Shane Fang
(74) *Attorney, Agent, or Firm* — Oblon, McClelland, Maier & Neustadt, L.L.P.

(57) ABSTRACT

Polymers comprising at least one unit of formula 1 and compounds of the formula 1' wherein, in formulae 1 and 1' n is 0, 1, 2, 3 or 4 m is 0, 1, 2, 3 or 4 X is at each occurrence selected from the group consisting of O, S, Se or Te, Q is at each occurrence selected from the group consisting of C, Si or Ge R is at each occurrence selected from the group consisting of hydrogen, $C_{1-30}$-alkyl, $C_{2-30}$-alkenyl, $C_{2-30}$-alkynyl, $C_{5-12}$-cycloalkyl, $C_{6-18}$-aryl, $R^2$, $R^{2'}$, $R^*$ are at each occurrence independently selected from the group consisting of hydrogen, $C_{1-30}$-alkyl, $C_{2-30}$-alkenyl, $C_{2-30}$-alkynyl, $C_{5-12}$-cycloalkyl, $C_{6-18}$-aryl, 5 to 20 membered hetero-aryl, $OR^{21}$, $OC(O)-R^{21}$, $C(O)-OR^{21}$, $C(O)-R^{21}$, $NR^{21}_R{}^{22}$,
(Continued)

$NR^{21}$—$C(O)R^{22}$, $C(O)$—$NR^{21}R^{22}$, $N[C(O)R^{21}][C(O)R^{22}]$, $SR^{21}$, halogen, CN, $SiR^{Sis}R^{Sit}R^{Siu}$ and OH, $L^1$ and $L^2$ are independently from each other and at each occurrence selected from the group consisting of $C_{6-30}$-arylene, 5 to 30 membered heteroarylene.

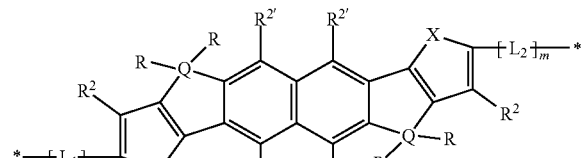

(1)

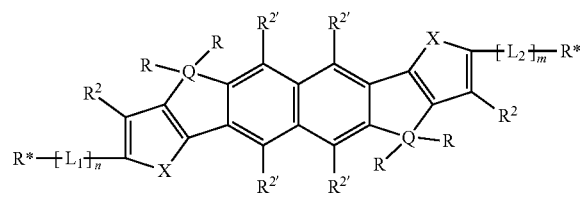

(1')

20 Claims, 2 Drawing Sheets

(51) Int. Cl.
*H01L 51/00* (2006.01)
*H01L 51/05* (2006.01)

(52) U.S. Cl.
CPC .... *H01L 51/0043* (2013.01); *C08G 2261/124* (2013.01); *C08G 2261/3243* (2013.01); *C08G 2261/3246* (2013.01); *C08G 2261/344* (2013.01); *C08G 2261/411* (2013.01); *C08G 2261/51* (2013.01); *C08G 2261/92* (2013.01); *H01L 51/0545* (2013.01); *H01L 51/0558* (2013.01)

(58) Field of Classification Search
CPC ..... C07D 417/14; C07D 495/22; H01L 51/00; H01L 51/0074; H01L 51/0071; H01L 51/0072; H01L 51/0073; H01L 51/0558
See application file for complete search history.

(56) References Cited

FOREIGN PATENT DOCUMENTS

WO WO 2014/086457 A1 6/2014
WO WO 2015/025981 A1 2/2015

OTHER PUBLICATIONS

International Preliminary Report on Patentability dated Dec. 8, 2017 in PCT/EP2016/080309 filed Dec. 8, 2016, 27 pages.
Yunlong Ma, et al., "Ladder-Type Dithienonaphthalene-Based Donor-Acceptor Copolymers for Organic Solar Cells" Macromolecules, vol. 46, No. 12, XP055096407, Jun. 25, 2013, pp. 4813-4821.
Yunlong Ma, et al., "Improving the Photovoltaic Performance of Ladder-Type Dithienonaphthalene-Containing Copolymers Through Structural Isomerization" Journal of Materials Chemistry A, vol. 2, 2014, pp. 13905-13915.

NAPHTHOINDACENODITHIOPHENES AND POLYMERS

The present invention relates to new Naphthoindacenodithiophenes (NDTs) and NDT-containing polymers made thereof, to a process for the preparation of these NDT compounds and NDT-containing polymers, to intermediates, to electronic devices comprising these polymers, as well as to the use of these polymers as semiconducting material.

Organic semiconducting materials can be used in electronic devices such as organic photovoltaic devices (OPVs), organic field-effect transistors (OFETs), organic light emitting diodes (OLEDs), organic photodiodes (OPDs) and organic electrochromic devices (ECDs).

It is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

For application in organic photovoltaic devices (OPVs), organic field-effect transistors (OFETs), and organic photodiodes (OPDs), it is further desirable that the organic semiconducting materials show high charge carrier mobility.

For application in organic photovoltaic devices (OPVs) and organic photodiodes (OPDs), the organic semiconducting materials should also show a strong absorption of the visible light and of the near infra-red light.

The use of regioisomeric Naphthoindacenodithiophene compounds as semiconducting materials in electronic devices is known in the art.

Ma et al., Macromolecules, 2013, 46, 4813-4821 describe semiconducting polymers comprising the following units of formula F1

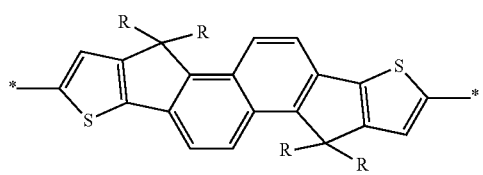

and organic field effect transistors comprising these polymers.

WO2015025981 describes as well compounds containing the unit of formula F1.

Ma et al., J. Mater. Chem. A, 2014, 2, 13905-13915 describe semiconducting polymers comprising the following units of formula F2

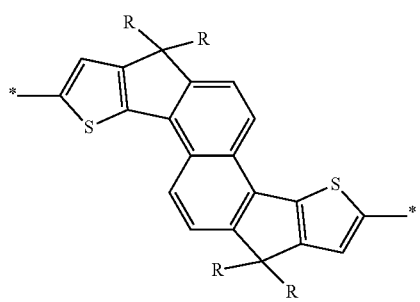

and organic field effect transistors comprising these polymers.

WO 2014086457 describes semiconducting polymers comprising the following generic units of formulae F3, F4 and F5

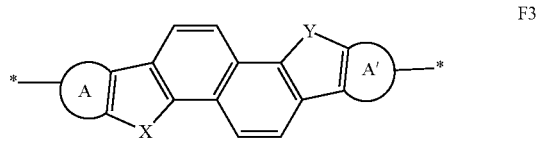

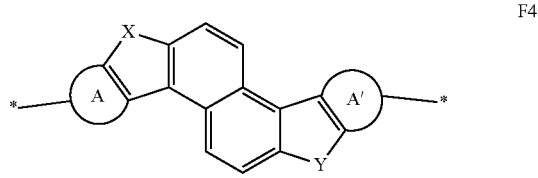

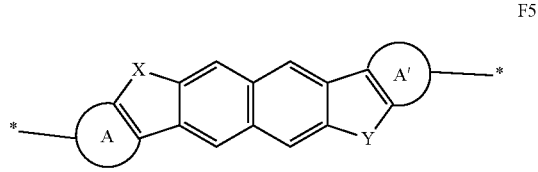

and organic field effect transistors comprising these polymers. Whereas some experimental data about compounds containing the generic formula F3 are given, only a prophetic synthesis route to the generic formula F5 is depicted, but no application results were described with compounds containing a unit of formula F5.

It was the object of the present invention to provide organic semiconducting materials. This object is solved by polymers of formula 1, compounds of formula 1', a process for the preparation of the polymers, intermediates for preparing the polymers, electronic devices comprising the polymers and the use of the polymers.

The polymers of the present invention comprise at least one unit of formula

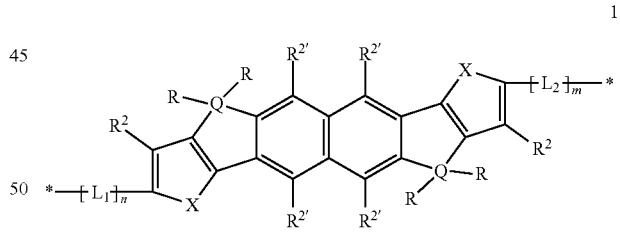

Also part of the invention are compounds of the formula 1'

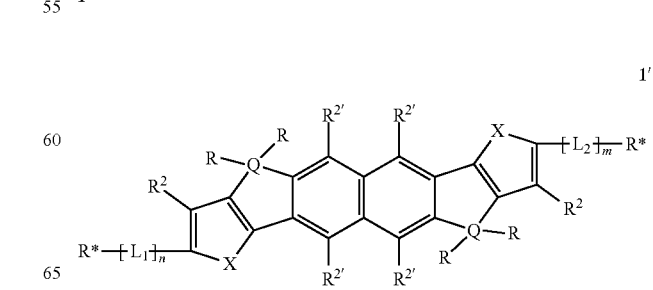

wherein, in formulae 1 and 1'
n is 0, 1, 2, 3 or 4
m is 0, 1, 2, 3 or 4
X is at each occurrence selected from the group consisting of O, S, Se or Te, preferably O, S or Se, more preferably S or Se, most preferably S;
Q is at each occurrence selected from the group consisting of C, Si or Ge, preferably C or Si, most preferably C;
R is at each occurrence selected from the group consisting of hydrogen, $C_{1-30}$-alkyl, $C_{2-30}$-alkenyl, $C_{2-30}$-alkynyl, $C_{5-12}$-cycloalkyl, $C_{6-18}$-aryl,
  wherein
    $C_{1-30}$-alkyl, $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^v$, $NR^vR^w$, $SR^v$ and halogen; and at least two $CH_2$-groups, but not adjacent $CH_2$-groups, of $C_{1-30}$-alkyl, $C_{2-30}$-alkenyl and $C_{2-30}$-alkynyl can be replaced by O or S,
    $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^v$, $NR^vR^w$, $SR^v$ and halogen; and one or two $CH_2$-groups, but not adjacent $CH_2$-groups, of $C_{5-12}$-cycloalkyl can be replaced by O, S, or $NR^e$,
    $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^v$, $NR^vR^w$, $NR^v$—$C(O)R^w$, $C(O)$—$NR^vR^w$, $SR^v$ and halogen,
    wherein
      $R^v$ and $R^w$ are independently selected from the group consisting of H, $C_{1-20}$-alkyl, $C_{2-20}$-alkenyl, $C_{2-20}$-alkynyl and $C_{5-8}$-cycloalkyl,
$R^2$, $R^{2'}$, $R^*$ are at each occurrence independently selected from the group consisting of hydrogen, $C_{1-30}$-alkyl, $C_{2-30}$-alkenyl, $C_{2-30}$-alkynyl, $C_{5-12}$-cycloalkyl, $C_{6-18}$-aryl, 5 to 20 membered heteroaryl, $OR^{21}$, $OC(O)$—$R^{21}$, $C(O)$—$OR^{21}$, $C(O)$—$R^{21}$, $NR^{21}R^{22}$, $NR^{21}$—$C(O)R^{22}$, $C(O)$—$NR^{21}R^{22}$, $N[C(O)R^{21}][C(O)R^{22}]$, $SR^{21}$, halogen, CN, $SiR^{Sis}R^{Sit}R^{Siu}$ and OH,
  wherein
    $R^{21}$ and $R^{22}$ and are independently selected from the group consisting of H, $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, and
    $C_{1-30}$-alkyl, $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^e$, $OC(O)$—$R^e$, $C(O)$—$OR^e$, $C(O)$—$R^e$, $NR^eR^f$, $NR^e$—$C(O)R^f$, $C(O)$—$NR^eR^f$, $N[C(O)R^e][C(O)R^f]$, $SR^e$, halogen, CN, $SiR^{Sis}R^{Sit}R^{Siu}$ and $NO_2$; and at least two $CH_2$-groups, but not adjacent $CH_2$-groups, of $C_{1-30}$-alkyl, $C_{2-30}$-alkenyl and $C_{2-30}$-alkynyl can be replaced by O or S,
    $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^e$, $OC(O)$—$R^e$, $C(O)$—$OR^e$, $C(O)$—$R^e$, $NR^eR^f$, $NR^e$—$C(O)R^f$, $C(O)$—$NR^eR^f$, $N[C(O)R^e][C(O)R^f]$, $SR^e$, halogen, CN, $SiR^{Sis}R^{Sit}R^{Siu}$ and $NO_2$; and
    one or two $CH_2$-groups, but not adjacent $CH_2$-groups, of $C_{5-12}$-cycloalkyl can be replaced by O, S, OC(O), CO, $NR^e$ or $NR^e$—CO,
    $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^e$, $OC(O)$—$R^e$, $C(O)$—$OR^e$, $C(O)$—$R^e$, $NR^eR^f$, $NR^e$—$C(O)R^f$, $C(O)$—$NR^eR^f$, $N[C(O)R^e][C(O)R^f]$, $SR^e$, halogen, CN, $SiR^{Sis}R^{Sit}R^{Siu}$ and $NO_2$,
    wherein
      $R^{Sis}$, $R^{Sit}$ and $R^{Siu}$ are independently from each other selected from the group consisting of H, $C_{1-20}$-alkyl, $C_{2-20}$-alkenyl, $C_{2-20}$-alkynyl, $C_{5-6}$-cycloalkyl, phenyl and O—$Si(CH_3)_3$,
      $R^e$ and $R^f$ are independently selected from the group consisting of H, $C_{1-20}$-alkyl, $C_{2-20}$-alkenyl, $C_{2-20}$-alkynyl, $C_{6-8}$-cycloalkyl, $C_{6-14}$-aryl, and 5 to 14 membered heteroaryl,
      wherein
        $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^g$—$C(O)R^h$, $C(O)$—$NR^gR^h$, $N[C(O)R^g][C(O)R^h]$, $SR^g$, halogen, CN, and $NO_2$;
        $C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^g$—$C(O)R^h$, $C(O)$—$NR^gR^h$, $N[C(O)R^g][C(O)R^h]$, $SR^g$, halogen, CN, and $NO_2$;
        $C_{6-14}$-aryl and 5 to 14 membered heteroaryl can be substituted with one to five substituents independently selected from the group consisting of $C_{1-10}$-alkyl, $C_{2-0}$-alkenyl, $C_{2-10}$-alkynyl, $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^g$—$C(O)R^h$, $C(O)$—$NR^gR^h$, $N[C(O)R^g][C(O)R^h]$, $SR^g$, halogen, CN, and $NO_2$;
        wherein
          $R^g$ and $R^h$ are independently selected from the group consisting of H, $C_{1-10}$-alkyl, $C_{2-10}$-alkenyl and $C_{2-10}$-alkynyl,
          wherein
            $C_{1-10}$-alkyl, $C_{2-10}$-alkenyl and $C_{2-10}$-alkynyl can be substituted with one to five substituents selected from the group consisting of halogen, CN and $NO_2$,
$L^1$ and $L^2$ are independently from each other and at each occurrence selected from the group consisting of $C_{6-30}$-arylene, 5 to 30 membered heteroarylene,

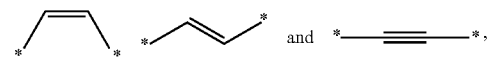

wherein
$C_{6-30}$-arylene and 5 to 30 membered heteroarylene can be substituted with one to six substituents $R^3$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)$—$R^{31}$, $C(O)$—$OR^{31}$, C(O)—R³¹, NR³¹R³², NR³¹—C(O)R³², C(O)—NR³¹R³², N[C(O)R³¹][C(O)R³²], SR³¹, halogen, CN, SiR^{Siv}R^{Siw}R^{Six} and OH, and
wherein

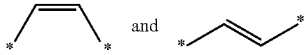

can be substituted with one or two substituents R⁴ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, C(O)—R⁴¹, C(O)—NR41R42, OR⁴¹ and CN,
  wherein
    R³¹, R³², R⁴¹ and R⁴² are independently from each other and at each occurrence selected from the group consisting of H, $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, and
  wherein
    $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, OR^i, OC(O)—R^j, C(O)—OR^i, C(O)—R^i, NR^iR^j, NR^i—C(O)R^j, C(O)—NR^iR^j, N[C(O)R^i][C(O)R^j], SR^i, halogen, CN, SiR^{Siv}R^{Siw}R^{Six} and NO₂; and at least two CH₂-groups, but not adjacent CH₂-groups of $C_{1-30}$-alkyl, $C_{2-30}$-alkenyl and $C_{2-30}$-alkynyl can be replaced by O or S,
    $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, OR^i, OC(O)—R^j, C(O)—OR^i, C(O)—R^i, NR^iR^j, NR¹—C(O)R^j, C(O)—NR^iR^j, N[C(O)R^i][C(O)R^j], SR^i, halogen, CN, SiR^{Siv}R^{Siw}R^{Six} and NO₂; and one or two CH₂-groups, but not adjacent CH₂-groups, of $C_{5-12}$-cycloalkyl can be replaced by O, S, OC(O), CO, NR^i or NR^i—CO,
    $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, OR^i, OC(O)—R^j, C(O)—OR^i, C(O)—R^i, NR^iR^j, NR^i—C(O)R^j, C(O)—NR^iR^j, N[C(O)R^i][C(O)R^j], SR^i, halogen, CN, SiR^{Siv}R^{Siw}R^{Six} and NO₂,
      wherein
        R^{Siv}, R^{Siw}, R^{Six} are independetly from each other selected from the group consisting of H, $C_{1-20}$-alkyl, $C_{2-20}$-alkynyl, $C_{5-6}$-cycloalkyl, phenyl and O—Si(CH₃)₃,
        R^i and R_j are independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl,
        wherein
          $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, OR^k, OC(O)—R^l, C(O)—OR^k, C(O)—R^k, NR^kR^l, NR^k—C(O)R^l, C(O)—NR^kR^l, N[C(O)R^k][C(O)R^l], SR^k, halogen, CN, and NO₂;
          $C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR^k, OC(O)—R^l, C(O)—OR^k, C(O)—R^k, NR^kR^l, NR^k—C(O)R^l, C(O)—NR^kR^l, N[C(O)R^k][C(O)R^l], SR^k, halogen, CN, and NO₂;
          $C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR^k, OC(O)—R^l, C(O)—OR^k, C(O)—R^k, NR^kR^l, NR^k—C(O)R^l, C(O)—NR^kR^l, N[C(O)R^k][C(O)R^l], SR^k, halogen, CN, and NO₂;
          wherein
            R^k and R^l are independently selected from the group consisting of H, $C_{1-10}$-alkyl, $C_{2-10}$-alkenyl and $C_{2-10}$-alkynyl,
            wherein
              $C_{2-10}$-alkenyl and $C_{2-10}$-alkynyl can be substituted with one to five substituents selected from the group consisting of halogen, CN and NO₂.

Halogen can be F, Cl, Br and I.
X are preferably at each occurrence the same.
Q are preferably at each occurrence the same.
R² are preferably at each occurrence the same.
R" are preferably at each occurrence the same.

$C_{1-4}$-alkyl, $C_{1-10}$-alkyl, $C_{1-20}$-alkyl, $C_{1-30}$-alkyl, $C_{1-36}$-alkyl, $C_{1-50}$-alkyl, $C_{1-60}$-alkyl and $C_{1-100}$-alkyl can be branched or unbranched. Examples of $C_{1-4}$-alkyl are methyl, ethyl, n-propyl, isopropyl, n-butyl, sec-butyl, isobutyl and tert-butyl. Examples of $C_{1-10}$-alkyl are $C_{1-4}$-alkyl, n-pentyl, neopentyl, isopentyl, n-(1-ethyl)propyl, n-hexyl, n-heptyl, n-octyl, n-(2-ethyl)hexyl, n-nonyl and n-decyl. Examples of $C_{1-20}$-alkyl are $C_{1-10}$-alkyl and n-undecyl, n-dodecyl, n-undecyl, n-dodecyl, n-tri-decyl, n-tetradecyl, n-pentadecyl, n-hexadecyl, n-heptadecyl, n-octadecyl, n-nonadecyl and n-icosyl ($C_{20}$). Examples of $C_{1-30}$-alkyl, $C_{1-36}$-alkyl, $C_{1-50}$-alkyl, $C_{1-60}$-alkyl and $C_{1-100}$-alkyl are $C_{1-20}$-alkyl and n-docosyl ($C_{22}$), n-tetracosyl ($C_{24}$), n-hexacosyl ($C_{26}$), n-octacosyl ($C_{28}$) and n-triacontyl ($C_{30}$).

$C_{2-10}$-alkenyl, $C_{2-20}$-alkenyl, $C_{2-30}$-alkenyl, $C_{2-60}$-alkenyl and $C_{2-100}$-alkenyl can be branched or unbranched. Examples of $C_{1-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl. Examples of $C_{2-20}$-alkenyl, $C_{2-60}$-alkenyl and $C_{2-100}$-alkenyl are $C_{2-10}$-alkenyl and linoleyl ($C_{18}$), linolenyl ($C_{18}$), oleyl ($C_{18}$), and arachidonyl ($C_{20}$). Examples of $C_{2-30}$-alkenyl are $C_{2-20}$-alkenyl and erucyl ($C_{22}$).

$C_{2-10}$-alkynyl, $C_{2-20}$-alkynyl, $C_{2-30}$-alkynyl, $C_{2-60}$-alkynyl and $C_{2-100}$-alkynyl can be branched or unbranched. Examples of $C_{2-10}$-alkynyl are ethynyl, 2-propynyl, 2-butynyl, 3-butynyl, pentynyl, hexynyl, heptynyl, octynyl, nonynyl and decynyl. Examples of $C_{2-20}$-alkynyl, $C_{2-30}$-alkenyl, $C_{2-60}$-alkynyl and $C_{2-100}$-alkynyl are undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{5-6}$-cycloalkyl are cyclopentyl and cyclohexyl. Examples of $C_{5-8}$-cycloalkyl are $C_{5-6}$-cycloalkyl and cycloheptyl and cyclooctyl. $C_{5-12}$-cycloalkyl are $C_{5-8}$-cycloalkyl and cyclononyl, cyclodecyl, cycloundecyl and cyclododecyl.

Examples of $C_{6-10}$-aryl are phenyl,

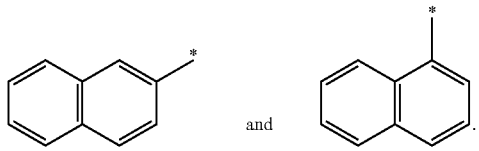

and

Examples of $C_{6-14}$-aryl are $C_{6-10}$-aryl and

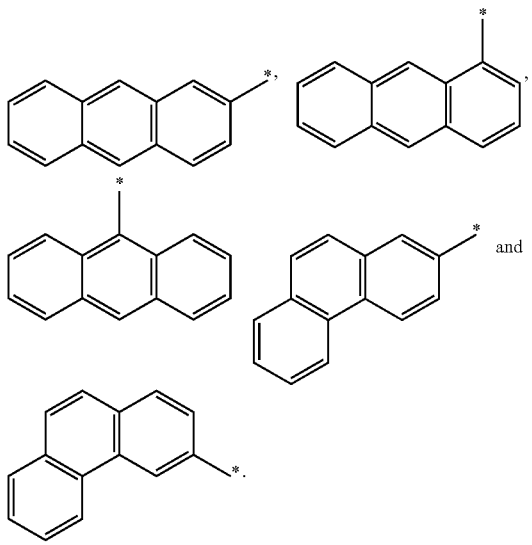

and

Examples of $C_{6-18}$-aryl are $C_{6-14}$-aryl and

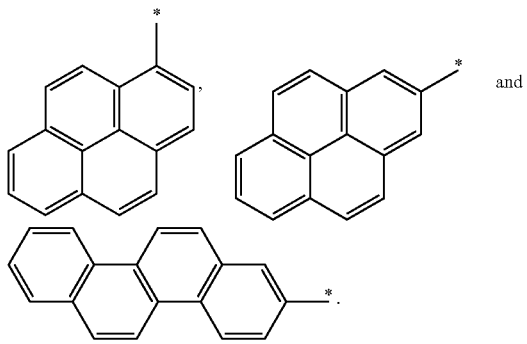

5 to 10 membered heteroaryl are 5 to 10 membered monocyclic or polycyclic, such as dicyclic, tricyclic or tetracyclic, ring systems, which comprise at least one heteroaromatic ring, and which may also comprise non-aromatic rings, which may be substituted by =O.

5 to 14 membered heteroaryl are 5 to 14 membered monocyclic or polycyclic, such as dicyclic, tricyclic or tetracyclic, ring systems, which comprise at least one heteroaromatic ring, and which may also comprise non-aromatic rings, which may be substituted by =O.

5 to 20 membered heteroaryl are 5 to 20 membered monocyclic or polycyclic, such as dicyclic, tricyclic or tetracyclic, ring systems, which comprise at least one heteroaromatic ring, and which may also comprise non-aromatic rings, which may be substituted by =O.

Examples of 5 to 10 membered heteroaryl are

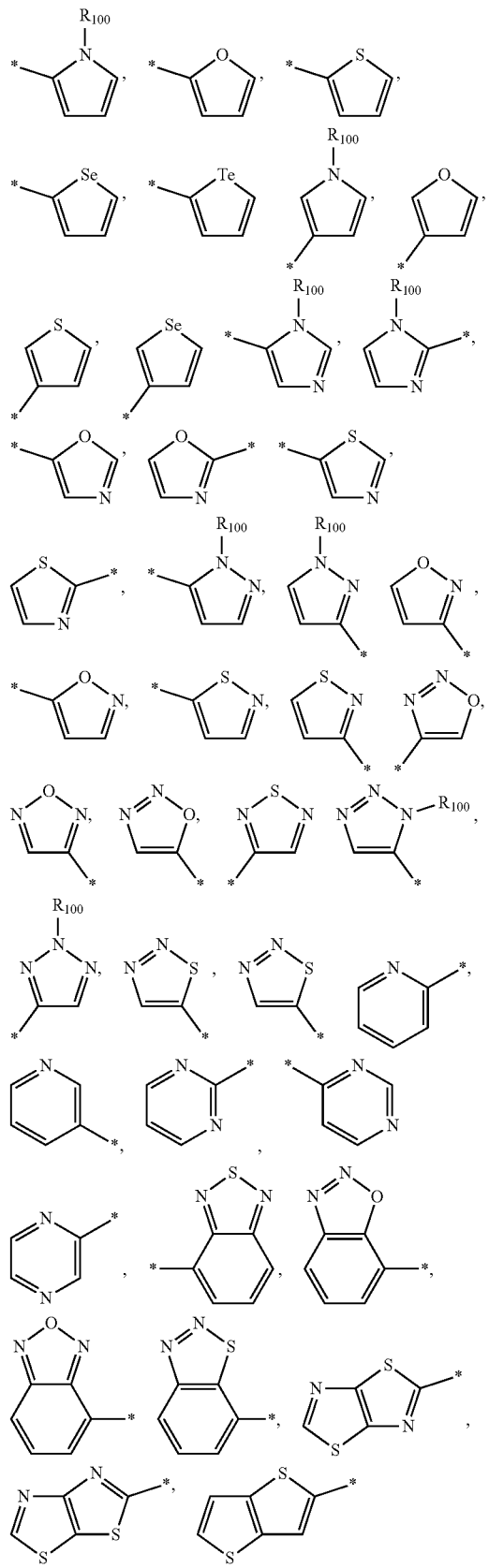

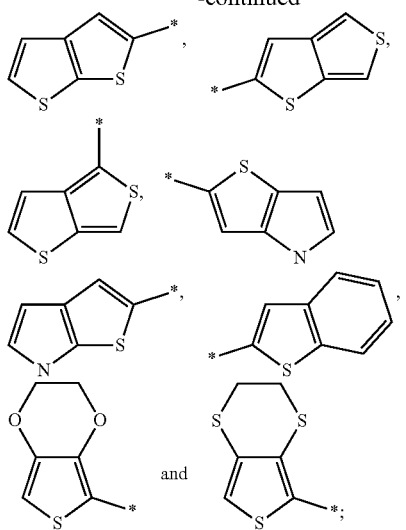
Examples of 5 to 14 membered heteroaryl are the examples given for the 5 to 10 membered heteroaryl and
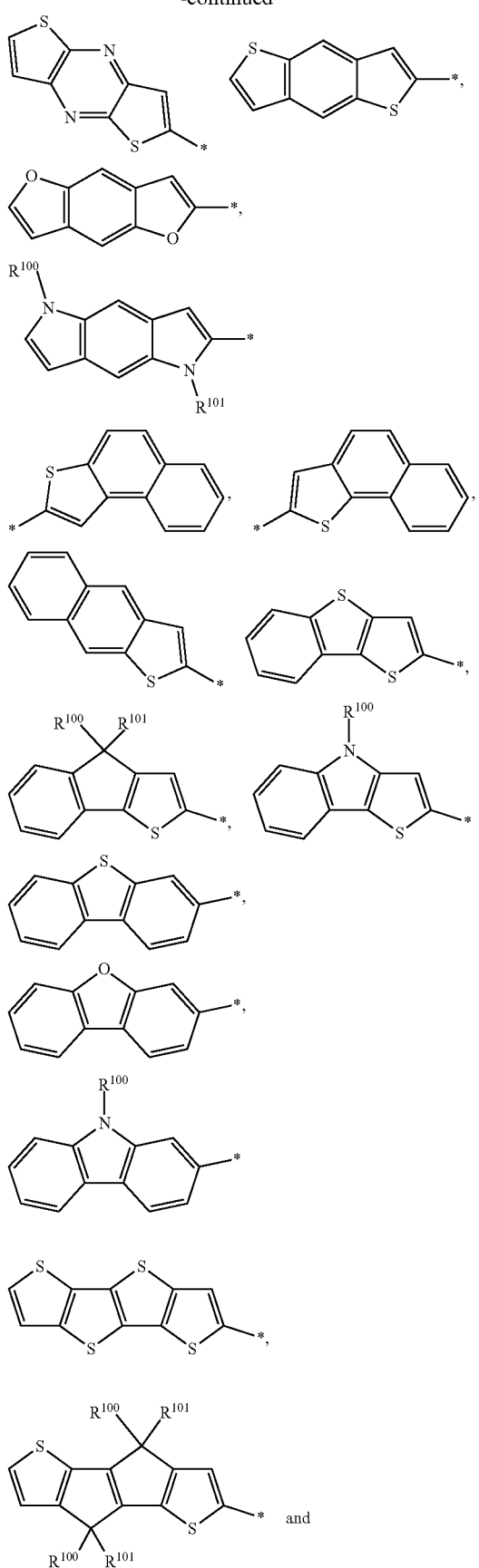

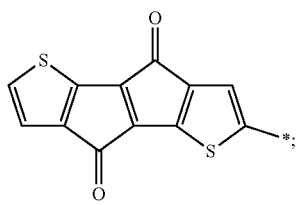

Examples of 5 to 20 membered heteroaryl are the examples given for the 5 to 14 membered heteroaryl and

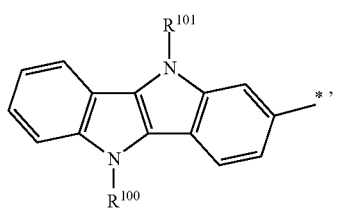

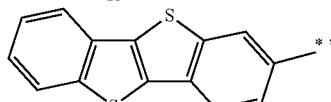

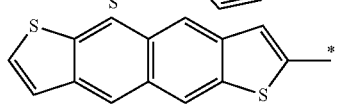

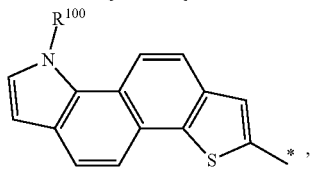

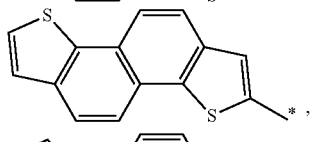

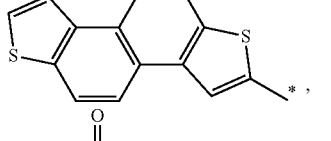

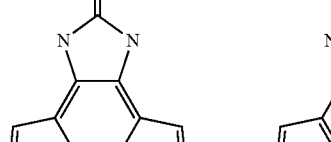

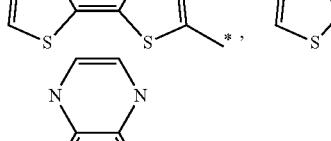

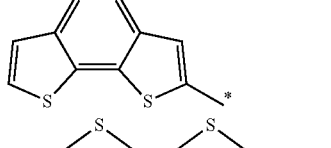

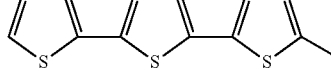

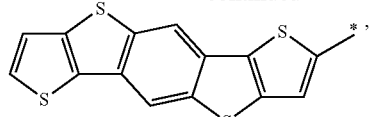

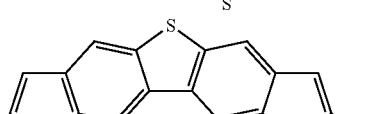

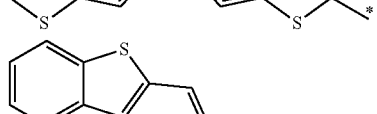

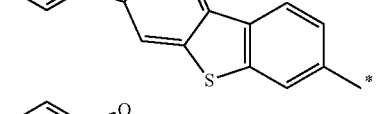

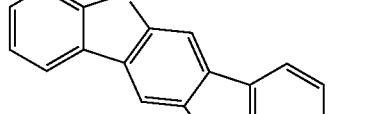

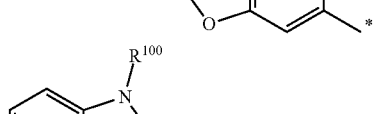

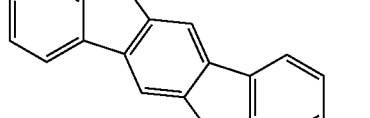

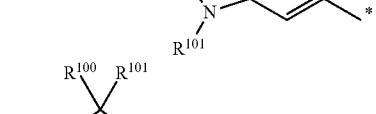

and

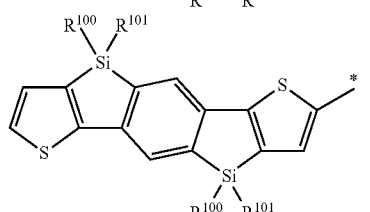

wherein
$R^{100}$ and $R^{101}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{100}$ and $R^{101}$, if attached to the same atom, together with the atom, to which they are attached, form a 5 to 12 membered ring system,
wherein
$C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^q$, $NR^qR^r$, $NR^q$—$C(O)R^r$, $C(O)$—$NR^qR^r$, $N[C(O)R^q][C(O)R^r]$, $SR^q$, halogen, CN, and $NO_2$;
$C_{5-8}$-cycloalkyl can be substituted with one to five substituents selected from the group consisting of $C_{1-10}$- alkyl, $C_{2-10}$-alkenyl, $C_{2-10}$-alkynyl, $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^q$, $NR^qR^r$, $NR^q$—$C(O)R^r$, $C(O)$—$NR^qR^r$, $N[C(O)R^q][C(O)R^r]$, $SR^q$, halogen, CN, and $NO_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^q$, $NR^qR^r$, $NR^q$—$C(O)R^r$, $C(O)$—$NR^qR^r$, $N[C(O)R^q][C(O)R^r]$, $SR^q$, halogen, CN, and $NO_2$;

5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^q$, $NR^qR^r$, $NR^q$—$C(O)R^r$, $C(O)$—$NR^qR^r$, $N[C(O)R^q][C(O)R^r]$, $SR^q$, halogen, CN, and $NO_2$;

wherein $R^q$ and $R^r$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

$C_{6-30}$-arylene is a 6 to 30 membered monocyclic or polycyclic, such as dicyclic, tricyclic, tetracyclic, pentacyclic or hexacyclic ring system, which comprises at least one C-aromatic ring, and which may also comprise non-aromatic rings or heteroaromatic rings, which may be substituted by =O.

Examples of $C_{6-30}$-arylene are

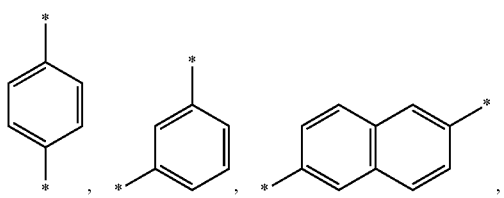

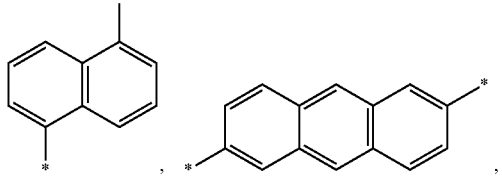

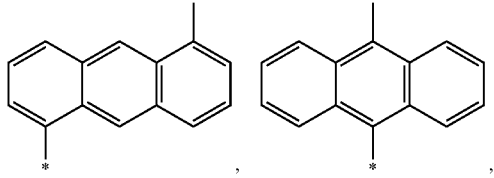

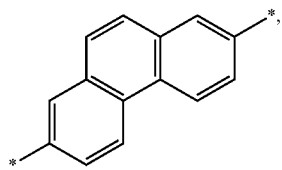

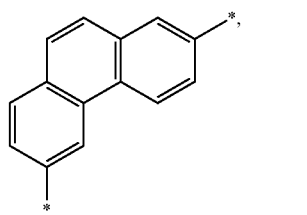

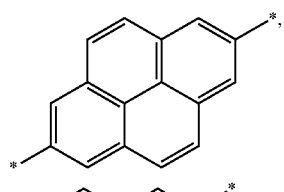

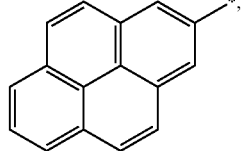

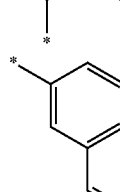

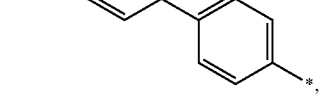

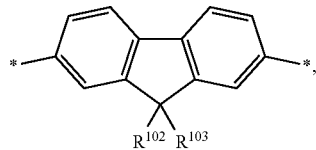

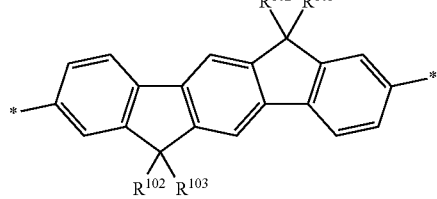

and

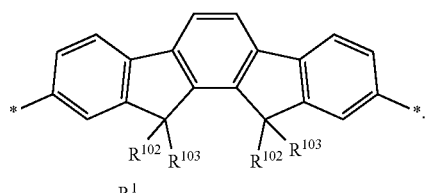

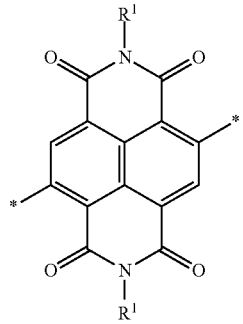

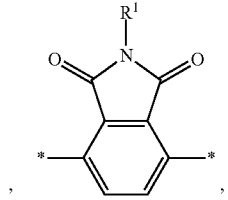

-continued

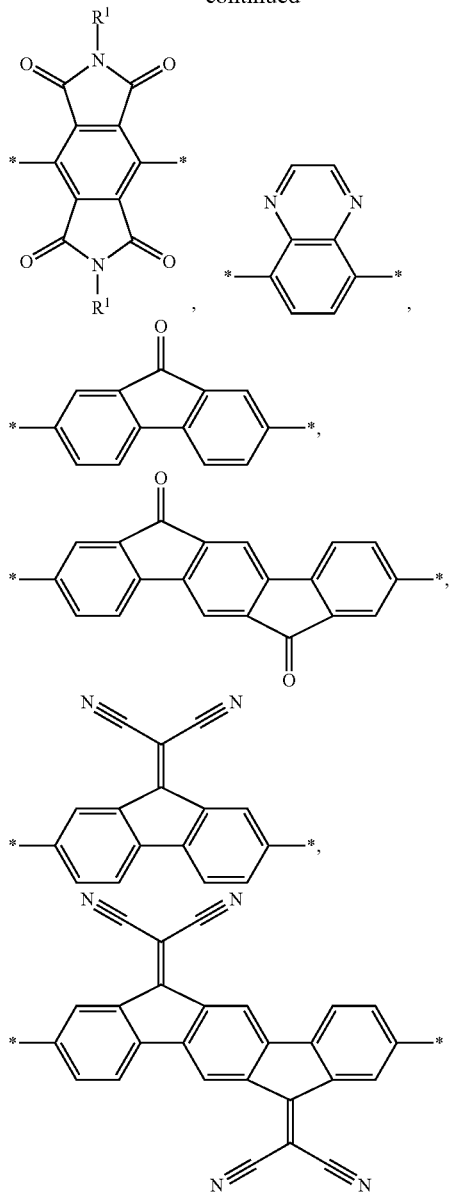

wherein
R¹ is at each occurrence selected from the group consisting of H, $C_{1-100}$-alkyl, $C_{2-100}$-alkenyl, $C_{2-100}$-alkynyl, $C_{5-12}$-cycloalkyl, $C_{6-18}$-aryl, a 5 to 20 membered heteroaryl, C(O)—$C_{1-100}$-alkyl, C(O)—$C_{5-12}$-cycloalkyl and C(O)—$OC_{1-100}$-alkyl,
  wherein
    $C_{1-100}$-alkyl, $C_{2-100}$-alkenyl and $C_{2-100}$-alkynyl can be substituted with one to fourty substituents independently selected from the group consisting of $C_{5-8}$-cycloalkyl, $C_{6-14}$-aryl, 5 to 14 membered heteroaryl, $OR^a$, $OC(O)—R^a$, $C(O)—OR^a$, $C(O)—R^a$, $NR^aR^b$, $NR^a—C(O)R^b$, $C(O)—NR^aR^b$, $N[C(O)R^a][C(O)R^b]$, $SR^a$, $Si(R^{Sia})(R^{Sib})(R^{Sic})$, —O—$Si(R^{Sia})(R^{Sib})(R^{Sic})$, halogen, CN, and $NO_2$; and at least two $CH_2$-groups, but not adjacent $CH_2$-groups, of $C_{1-100}$-alkyl, $C_{2-100}$-alkenyl and $C_{2-100}$-alkynyl can be replaced by O or S,
    $C_{5-12}$-cycloalkyl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)—R^a$, $C(O)—OR^a$, $C(O)—R^a$, $NR^aR^b$, $NR^a—C(O)R^b$, $C(O)—NR^aR^b$, $N[C(O)R^a][C(O)R^b]$, $SR^a$, $Si(R^{Sia})(R^{Sib})(R^{Sic})$, —O—$Si(R^{Sia})(R^{Sib})(R^{Sic})$, halogen, CN, and $NO_2$; and one or two $CH_2$-groups, but not adjacent $CH_2$-groups, of $C_{5-12}$-cycloalkyl can be replaced by O, S, OC(O), CO, $NR^a$ or $NR^a$—CO,
    $C_{6-18}$-aryl and 5 to 20 membered heteroaryl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)—R^a$, $C(O)—OR^a$, $C(O)—R^a$, $NR^aR^b$, $NR^a—C(O)R^b$, $C(O)—NR^aR^b$, $N[C(O)R^a][C(O)R^b]$, $SR^a$, $Si(R^{Sia})(R^{Sib})(R^{Sic})$, —O—$Si(R^{Sia})(R^{Sib}),(R^{Sic})$, halogen, CN, and $NO_2$,
  wherein
    $R^a$ and $R^b$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl and 5 to 14 membered heteroaryl,
    $R^{Sia}$, $R^{Sib}$ and $R^{Sic}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, O—$C_{1-60}$-alkyl, O—$C_{2-60}$-alkenyl, O—$C_{2-60}$-alkynyl, O—$C_{5-8}$-cycloalkyl, O—$C_{6-14}$-aryl, O-5 to 14 membered heteroaryl, —$[O—SiR^{Sid}R^{Sie}]_o—R^{Sif}$, $NR^5R^6$, halogen and O—C(O)—$R^5$,
    wherein
    o is an integer from 1 to 50,
    $R^{Sid}$, $R^{Sie}$, $R^{Sif}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, O—$C_{1-60}$-alkyl, O—$C_{2-60}$-alkenyl, O—$C_{2-60}$-alkynyl, O—$C_{5-8}$-cycloalkyl, O—$C_{6-4}$-aryl, O-5 to 14 membered heteroaryl, —$[O—SiR^{Sig}R^{Sih}]_p—R^{Sii}$, $NR^{50}R^{60}$, halogen and —C(O)—$R^{50}$;
    wherein
    p is an integer from 1 to 50,
    $R^{Sig}$ $R^{Sih}$, $R^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, O—$Si(CH_3)_3$, $NR^{500}R^{600}$, halogen and O—C(O)—$R^{500}$,
    $R^5$, $R^6$, $R^{50}$, $R^{60}$, $R^{500}$ and $R^{600}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, and 5 to 14 membered heteroaryl,
    $C_{2-60}$-alkenyl and $C_{2-60}$-alkynyl can be substituted with one to twenty substituents selected from the group consisting of $C_{5-6}$-cycloalkyl, $C_{6-10}$-aryl, $OR^c$, $OC(O)—R^c$, $C(O)—OR^c$, $C(O)—R^c$, $NR^cR^d$, $NR^c—C(O)R^d$, $C(O)$-$NR^cR^d$, $N[C(O)R^c][C(O)R^d]$, $SR^c$, $Si(R^{Sij})(R^{Sik})(R^{Sil})$, —O—$Si(R^{Sij})(R^{Sik})(R^{Sil})$, halogen, CN, and $NO_2$; and at least two $CH_2$-groups, but not adjacent $CH_2$-groups, of $C_{1-60}$-alkyl, $C_{2-60}$-alkenyl and $C_{2-60}$-alkynyl can be replaced by O or S, $C_{5-8}$-cycloalkyl can be substituted with one to five substituents selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$R$^d$, NR$^c$—C(O)R$^d$, C(O)—NR$^c$R$^d$, N[C(O)R$^c$][C(O)R$^d$], SR$^c$, Si(R$^{Sij}$)(R$^{Sik}$)(R$^{Sil}$), —O—Si(R$^{Sij}$)(R$^{Sik}$)(R$^{Sil}$), halogen, CN, and NO$_2$; and one or two CH$_2$-groups, but not adjacent CH$_2$-groups, of $C_{5-8}$-cycloalkyl can be replaced by O, S, OC(O), CO, NR$^c$ or NR$^c$—CO, $C_{6-14}$-aryl and 5 to 14 membered heteroaryl can be substituted with one to five substituents independently selected from the group consisting of $C_{1-30}$-alkyl, $C_{02-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$R$^d$, NR$^c$—C(O)R$^d$, C(O)—NR$^c$R$^d$, N[C(O)R$^c$][C(O)R$^d$], SR$^c$, Si(R$^{Sij}$)(R$^{Sik}$)(R$^{Sil}$), —O—Si(R$^{Sij}$)(R$^{Sik}$)(R$^{Sil}$), halogen, CN and NO$_2$;

wherein

R$^c$ and R$^d$ are independently selected from the group consisting of H, $C_{1-30}$-alkyl, $C_{2-30}$-alkenyl and $C_{2-30}$-alkynyl, R$^{Sij}$, R$^{Sik}$, and R$^{Sil}$ are independently selected from the group consisting of H, $C_{1-30}$-alkenyl, $C_{2-30}$-alkynyl, $C_{2-30}$-alkynyl, $C_{5-6}$-cycloalkyl, $C_{6-10}$-aryl, 5 to 10 membered heteroaryl, O—$C_{1-30}$-alkenyl, O—$C_{2-30}$-alkynyl, O—$C_{5-6}$-cycloalkyl, O—$C_{6-10}$-aryl, O-5 to 10 membered heteroaryl, —[O—SiR$^{Sim}$R$^{Sin}$]$_q$—R$^{Sio}$, NR$^7$R$^8$, halogen, and O—C(O)—R$^7$, wherein q is an integer from 1 to 50, R$^{Sim}$, R$^{Sin}$, R$^{Sio}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, —[O—SiR$^{Sip}$R$^{Siq}$]$_r$—R$^{Sir}$, NR$^{70}$R$^{80}$, halogen, and O—C(O)—R$^{70}$;

wherein r is an integer from 1 to 50,

R$^{Sip}$, R$^{Siq}$, R$^{Sir}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynl, O—$C_{5-6}$-cycloalkyl, O—$C_{6-10}$-aryl, O-5 to 10 membered heteroaryl, O—Si(CH$_3$)$_3$, NR$^{700}$R$^{800}$, halogen and O—C(O)—R$^{700}$, R$^7$, R$^8$, R$^{70}$, R$^{80}$, R$^{700}$ and R$^{800}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, and 5 to 10 membered heteroaryl, $C_{1-30}$-alkyl, $C_{2-30}$-alkenyl and $C_{2-30}$-alkynyl can be substituted with one to ten substituents selected from the group consisting of halogen, CN and NO$_2$, R$^{102}$ and R$^{103}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or R$^{102}$ and R$^{103}$, if attached to the same atom, together with the atom, to which they are attached, form a 5 to 12 membered ring system, wherein $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;

5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;

wherein

R$^s$ and R$^t$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and NO$_2$.

5 to 30 membered heteroarylene is a 5 to 30 membered monocyclic or polycyclic, such as dicyclic, tricyclic, tetracyclic, pentacyclic or hexacyclic ring system, which comprises at least one heteroaromatic ring, and which may also comprise aromatic rings or non-aromatic rings, which may be substituted by =O.

Examples of 5 to 30 membered heteroarylene are

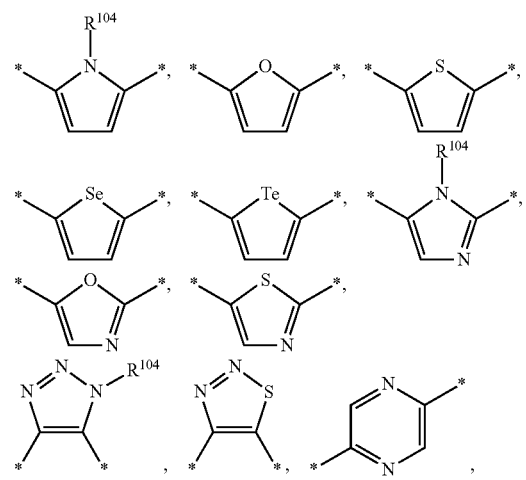

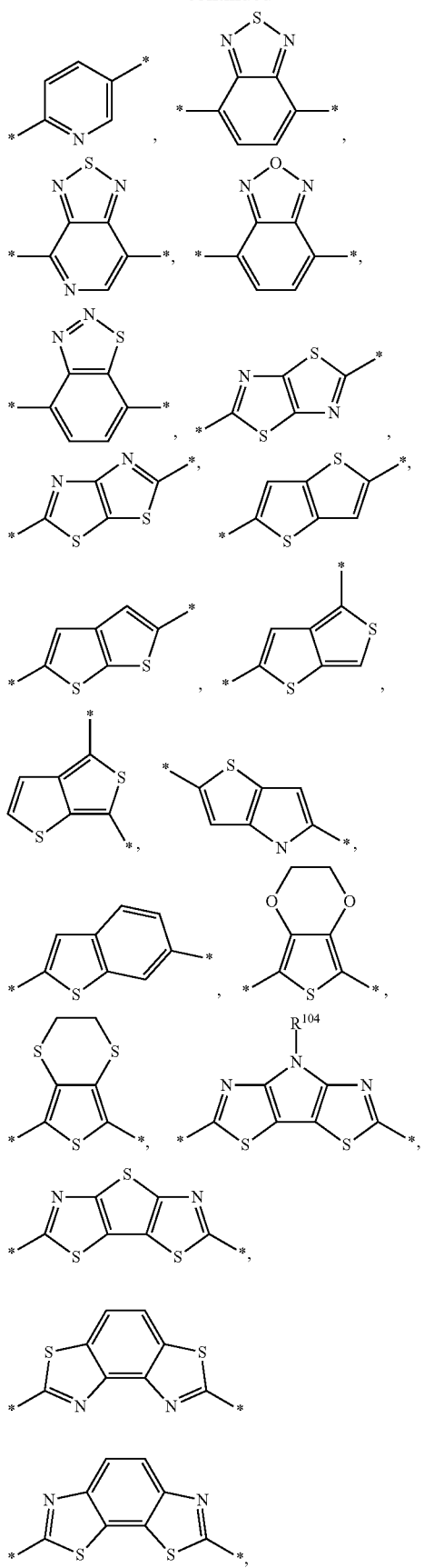
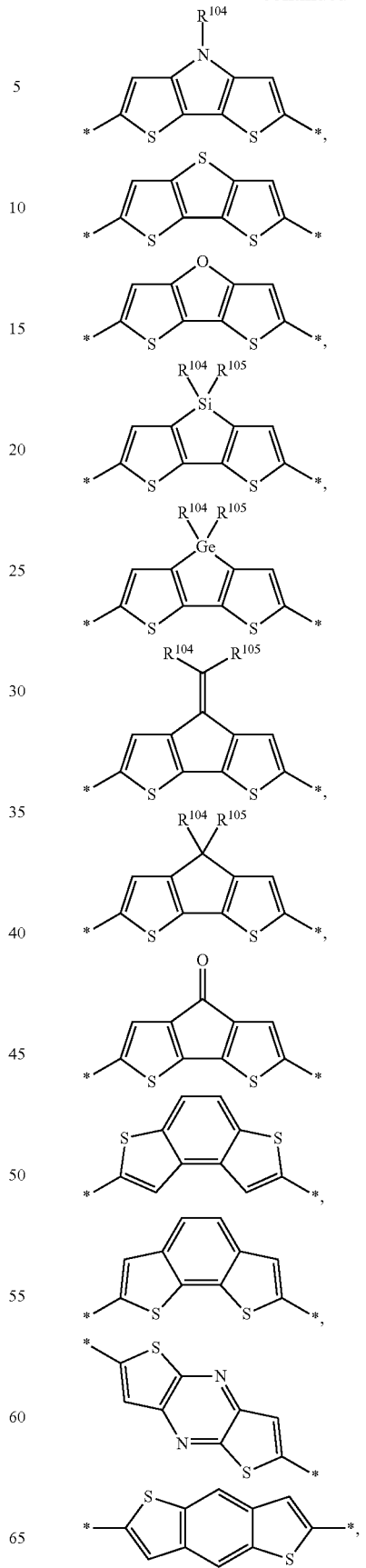

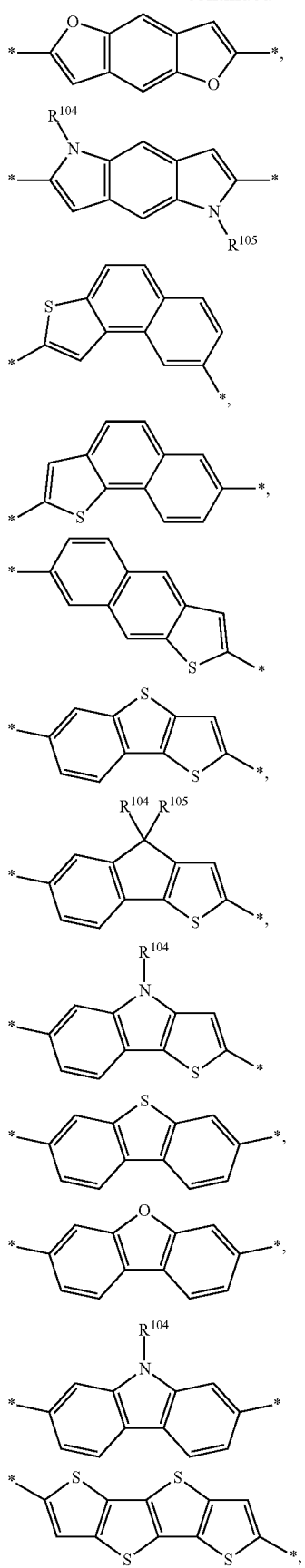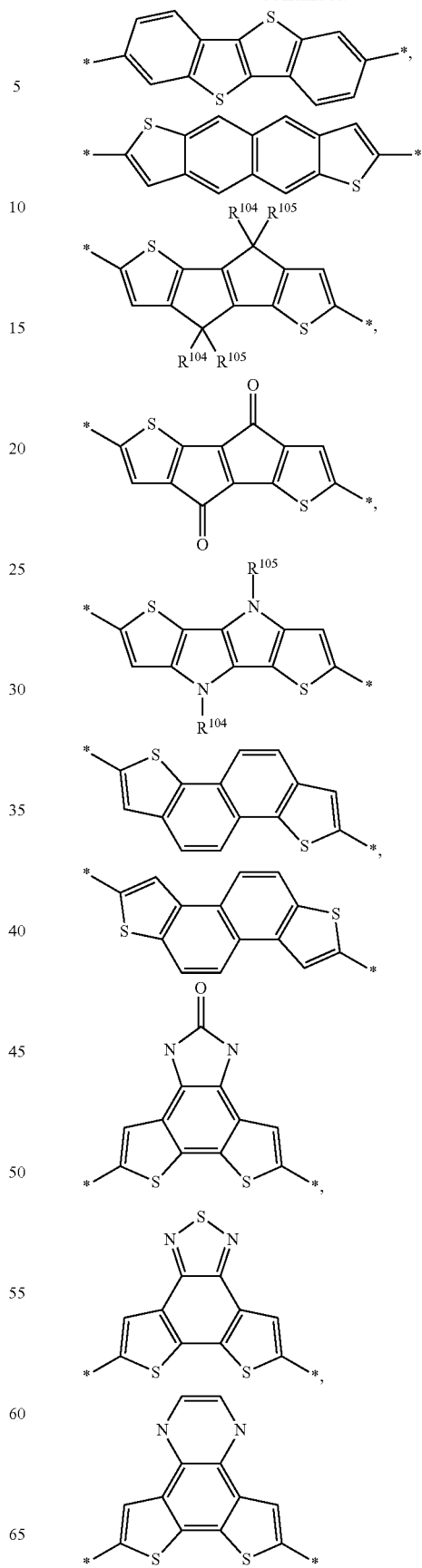

-continued
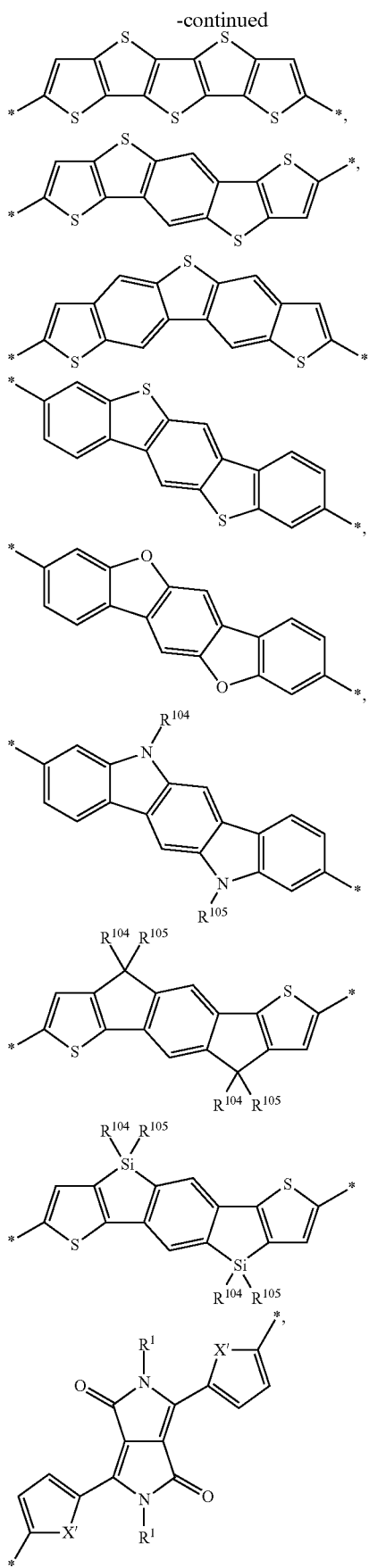
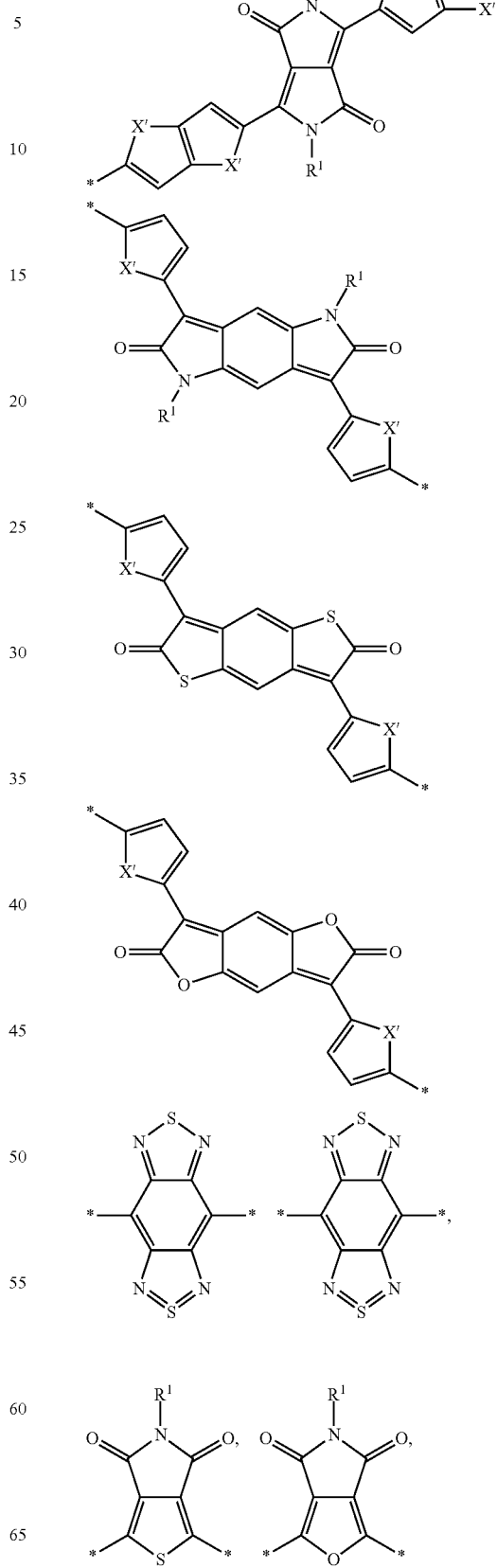
and

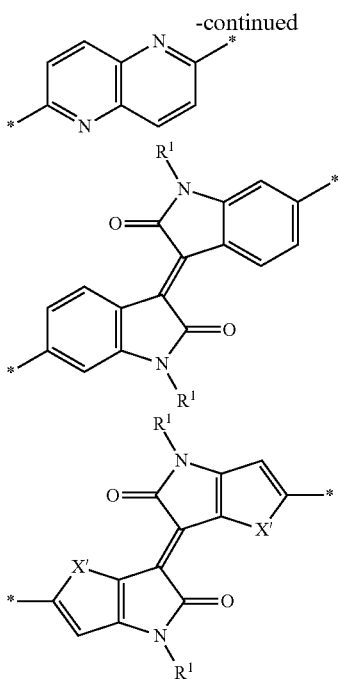

wherein

R¹ is defined as above

X' is at each occurrence selected from the group consisting of O, S, Se or Te, preferably O, S or Se, more preferably S or Se, most preferably S;

$R^{104}$ and $R^{105}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{104}$ and $R^{105}$, if attached to the same atom, together with the atom, to which they are attached, form a 5 to 12 membered ring system, wherein $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;

5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;

wherein $R^s$ and $R^t$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

The 5 to 12 membered ring system can contain, in addition to the atom, to which $R^{100}$ and $R^{101}$, respectively $R^{102}$ and $R^{103}$, respectively $R^{104}$ and $R^{105}$, are attached, ring members selected from the group consisting of $CH_2$, O, S and $NR^u$, werein $R^u$ is at each occurrence selected from the group consisting of H, $C_{1-10}$-alkyl, $C_{2-10}$-alkenyl and $C_{2-10}$-alkynyl.

Preferably, the polymers of the present invention comprise at least 60% by weight of units of formula (1) based on the weight of the polymer.

More preferably, the polymers of the present invention comprise at least 80% by weight of units of formula (1) based on the weight of the polymer.

Most preferably, the polymers of the present invention essentially consist of units of formula (1).

Preferably, $R^1$ is at each occurrence selected from the group consisting of H, $C_{1-100}$-alkyl, $C_{2-100}$-alkenyl, $C_{2-100}$-alkynyl, $C_{5-12}$-cycloalkyl, $C_{6-18}$-aryl, and a 5 to 20 membered heteroaryl, wherein $C_{1-100}$-alkyl, $C_{2-100}$-alkenyl and $C_{2-100}$-alkynyl can be substituted with one to fourty substituents independently selected from the group consisting of $C_{5-8}$-cycloalkyl, $C_{6-14}$-aryl, 5 to 14 membered heteroaryl, $OR^a$, $OC(O)$—$R^a$, $C(O)$—$OR^a$, $C(O)$—$R^a$, $NR^a$—$C(O)R^b$, $C(O)$—$NR^aR^b$, $SR^a$, $Si(R^{Sia})(R^{Sib})(R^{Sio})$, —O—$Si(R^{Sia})(R^{Sib})(R^{Sio})$, halogen and CN; and at least two $CH_2$-groups, but not adjacent $CH_2$-groups, of $C_{1-100}$-alkyl, $C_{2-100}$-alkenyl and $C_{2-100}$-alkynyl can be replaced by O or S, $C_{5-12}$-cycloalkyl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)$—$R^a$, $C(O)$—$OR^a$, $C(O)$—$R^a$, $NR^a$—$C(O)R^b$, $C(O)$—$NR^aR^b$, $SR^a$, $Si(R^{Sia})(R^{Sib})(R^{Sic})$, —O—$Si(R^{Sia})(R^{Sib})(R^{Sic})$, halogen, and CN; and one or two $CH_2$-groups, but not adjacent $CH_2$-groups, of $C_{5-12}$-cycloalkyl can be replaced by O, S, OC(O), CO, $NR^a$ or $NR^a$—CO, $C_{6-18}$-aryl and 5 to 20 membered heteroaryl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)$—$R^a$, $C(O)$—$OR^a$, $C(O)$—$R^a$, $NR^a$—$C(O)R^b$, $C(O)$—$NR^aR^b$, $SR^a$, $Si(R^{Sia})(R^{Sib})(R^{Sic})$, —O—$Si(R^{Sia})(R^{Sib})(R^{Sic})$, halogen, and CN, wherein $R^a$ and $R^b$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl and 5 to 14 membered heteroaryl, $R^{Sia}$, $R^{Sib}$ and $R^{Sic}$ are independently selected from the group consisting of H, $C_{1-60}$-alkyl, $C_{2-60}$-alkenyl, $C_{2-60}$-alkynyl, $C_{6-8}$-cycloalkyl, $C_{6-14}$-aryl, 5 to 14 membered heteroaryl, O—$C_{1-60}$-alkyl, O—$C_{2-60}$-alkenyl, O—$C_{2-60}$-alkynyl, O—$C_{6-8}$-cycloalkyl, —[O—$SiR^{Sid}R^{Sie}]_o$—$R^{Sif}$, wherein o is an integer from 1 to 50, $R^{Sid}$, $R^{Sie}$ and $R^{Sif}$ are independently selected from the group consisting of H, $C_{1-60}$-alkyl, $C_{2-60}$-alkenyl, $C_{2-60}$-alkynyl, $C_{6-8}$-cycloalkyl, $C_{6-14}$-aryl, —[O—SiR$^{Sig}$R$^{Sih}$]$_p$—R$^{Sii}$, wherein p is an integer from 1 to 50, $R^{Sig}$ $R^{Sih}$ and $R^{Sii}$ are independently selected from the group consisting of H, $C_{1-30}$-alkyl, $C_{2-30}$-alkenyl, $C_{2-30}$-alkynyl, $C_{56-6}$-cycloalkyl, $C_{6-10}$-aryl, O—Si(CH$_3$)$_3$, $C_{2-60}$-alkenyl and $C_{2-60}$-alkynyl can be substituted with one to twenty substituents selected from the group consisting of $C_{5-6}$-cycloalkyl, $C_{6-0}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, —O—Si(R$^{Sij}$)(R$^{Sik}$)(R$^{Sil}$), halogen, and CN; and at least two CH$_2$-groups, but not adjacent CH$_2$-groups, of $C_{1-60}$-alkyl, $C_{2-60}$-alkenyl and $C_{2-60}$-alkynyl can be replaced by O or S, $C_{5-8}$-cycloalkyl can be substituted with one to five substituents selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, Si(R$^{Sij}$)(R$^{Sik}$)(R$^{Sil}$), —O—Si(R$^{Sij}$)(R$^{Sik}$)(R$^{Sil}$), halogen, and CN; and one or two CH$_2$-groups, but not adjacent CH$_2$-groups, of $C_{6-8}$-cycloalkyl can be replaced by O, S, OC(O), CO, NR$^c$ or NR$^c$—CO, $C_{6-14}$-aryl and 5 to 14 membered heteroaryl can be substituted with one to five substituents independently selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, Si(R$^{Sij}$)(R$^{Sik}$)(R$^{Sil}$), —O—Si(R$^{Sij}$)(R$^{Sik}$)(R$^{Sil}$) halogen and CN;

wherein

R$^c$ and R$^d$ are independently selected from the group consisting of H, $C_{1-30}$-alkyl, $C_{2-30}$-alkenyl and $C_{2-30}$-alkynyl, $R^{Sij}$, $R^{Sik}$ and $R^{Sil}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—SiR$^{Sim}$R$^{Sin}$]$_q$—R$^{Sio}$, wherein q is an integer from 1 to 50, $R^{Sim}$, $R^{Si}$, $R^{Sio}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, —[O—SiR$^{Sip}$R$^{Siq}$]$_r$—R$^{Sir}$, NR$^{70}$R$^{80}$, halogen, and O—C(O)—R$^{70}$;

wherein r is an integer from 1 to 50, $R^{Sip}$, $R^{Siq}$, $R^{Sir}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, O—Si(CH$_3$)$_3$, NR$^{700}$R$^{800}$, halogen and O—C(O)—R$^{700}$, R$^{70}$, R$^{80}$, R$^{700}$ and R$^{800}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, and 5 to 10 membered heteroaryl, $C_{1-30}$-alkyl, $C_{2-30}$-alkenyl and $C_{2-30}$-alkynyl can be substituted with one to ten substituents selected from the group consisting of halogen and CN.

More preferably, R$^1$ is at each occurrence selected from the group consisting of $C_{1-100}$-alkyl, $C_{2-100}$-alkenyl and $C_{2-100}$-alkynyl, wherein $C_{1-100}$-alkyl, $C_{2-100}$-alkenyl and $C_{2-100}$-alkynyl can be substituted with one to fourty substituents independently selected from the group consisting of $C_{5-8}$-cycloalkyl, $C_{6-14}$-aryl, 5 to 14 membered heteroaryl, OR$^a$, OC(O)—R$^a$, C(O)—OR$^a$, C(O)—R$^a$, NR$^a$—C(O)R$^b$, C(O)—NR$^a$R$^b$, SR$^a$, Si(R$^{Sia}$)(R$^{Sib}$)(R$^{Sic}$), —O—Si(R$^{Sia}$)(R$^{Sib}$)(R$^{Sic}$), halogen, and CN; and at least two CH$_2$-groups, but not adjacent CH$_2$-groups, of $C_{1-100}$-alkyl, $C_{2-100}$-alkenyl and $C_{2-100}$-alkynyl can be replaced by O or S, wherein R$^a$ and R$^b$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl and 5 to 14 membered heteroaryl, $R^{Sia}$, $R^{Sib}$ and $R^{Sic}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, —[O—SiR$^{Sid}$R$^{Sie}$]$_o$—R$^{Sif}$, wherein o is an integer from 1 to 50, $R^{SId}$, $R^{Sie}$ and $R^{Sif}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, [O—SiR$^{Sig}$R$^{Sih}$]$_p$—R$^{Sii}$, wherein p is an integer from 1 to 50, $R^{Sig}$ $R^{Sih}$, $R^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, O—Si(CH$_3$)$_3$, $C_{1-60}$-alkyl, $C_{2-60}$-alkenyl and $C_{2-60}$-alkynyl can be substituted with one to twenty substituents selected from the group consisting of $C_{5-6}$-cycloalkyl, $C_{6-10}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, Si(R$^{Sij}$)(R$^{Sik}$)(R$^{Sil}$), —O—Si(R$^{Sij}$)(R$^{Sik}$)(R$^{Sil}$), halogen, and CN; and at least two CH$_2$-groups, but not adjacent CH$_2$-groups, of $C_{1-60}$-alkyl, $C_{2-60}$-alkenyl and $C_{2-60}$-alkynyl can be replaced by O or S, $C_{5-8}$-cycloalkyl can be substituted with one to five substituents selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, Si(R$^{Sij}$)(R$^{Sik}$)(R$^{Sil}$), O—Si(R$^{Sij}$)(R$^{Sik}$)(R$^{Sil}$), halogen, and CN; and one or two CH$_2$-groups, but not adjacent CH$_2$-groups, of $C_{5-8}$-cycloalkyl can be replaced by O, S, OC(O), CO, NR$^c$ or NR$^c$—CO, $C_{6-14}$-aryl and 5 to 14 membered heteroaryl can be substituted with one to five substituents independently selected from the group consisting of $C_{1-30}$- alkyl, $C_{2-30}$-alkenyl, $C_{2-30}$-alkynyl, $C_{5-6}$-cycloalkyl, $C_{6-10}$-aryl, $OR^c$, $OC(O)$—$R^c$, $C(O)$—$OR^c$, $C(O)$—$R^c$, $NR^c$—$C(O)R^d$, $C(O)$—$NR^cR^d$, $SR^c$, $Si(R^{Sij})(R^{Sik})(R^{Sil})$, $O$—$Si(R^{Sij}(R^{Sik})(R^{Sil})$, halogen, and CN;

wherein $R^c$ and $R^d$ are independently selected from the group consisting of H, $C_{1-30}$-alkyl, $C_{2-30}$-alkenyl and $C_{2-30}$-alkynyl, $R^{Sij}$, $R^{Sik}$ and $R^{Sil}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—$SiR^{Sim}R^{Sin}]_q$—$R^{Sio}$, wherein q is an integer from 1 to 50, $R^{Sim}$, $R^{Sin}$, $R^{Sio}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—$SiR^{Sip}R^{Siq}]_r$—$R^{Sir}$, wherein r is an integer from 1 to 50, $R^{Sip}$, $R^{Siq}$, $R^{Sir}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, O—$Si(CH_3)_3$, $C_{1-30}$-alkyl, $C_{2-30}$-alkenyl and $C_{2-30}$-alkynyl can be substituted with one to ten substituents selected from the group consisting of halogen and CN.

Even more preferably, $R^1$ is at each occurrence selected from the group consisting of $C_{1-50}$-alkyl, $C_{2-50}$-alkenyl and $C_{2-50}$-alkynyl, wherein $C_{1-50}$-alkyl, $C_{2-50}$-alkenyl and $C_{2-50}$-alkynyl can be substituted with one to twenty substituents independently selected from the group consisting of $C_{5-6}$-cycloalkyl, $C_{6-10}$-aryl, 5 to 10 membered heteroaryl, $OR^a$, $SR^a$, $Si(R^{Sia})(R^{Sib})(R^{Sic})$, —O—$Si(R^{Sia})(R^{Sib})(R^{Sic})$, halogen, and CN; and at least two $CH_2$-groups, but not adjacent $CH_2$-groups, of $C_{1-50}$-alkyl, $C_{2-50}$-alkenyl and $C_{2-50}$-alkynyl can be replaced by O or S, wherein $R^a$ is independently selected from the group consisting of H, $C_{1-30}$-alkyl, $C_{2-30}$-alkenyl, $C_{2-30}$-alkynyl, $C_{5-6}$-cycloalkyl and $C_{6-10}$-aryl, $R^{Sia}$, $R^{Sib}$ and $R^{Sic}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—$SiR^{Sid}(R^{Sie}]_o$—$R^{Sif}$, wherein o is an integer from 1 to 50, $R^{Sid}$, $R^{Sie}$, $R^{Sif}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—$SiR^{Sig}R^{Sih}]_p$—$R^{Sii}$, wherein p is an integer from 1 to 50, $R^{Sig}$ $R^{Sih}$, $R^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, O—$Si(CH_3)_3$, $C_{1-30}$-alkyl, $C_{2-30}$-alkenyl and $C_{2-30}$-alkynyl can be substituted with one to ten substituents selected from the group consisting of halogen and CN.

Most preferably, $R^1$ is at each occurrence selected from the group consisting of $C_{1-36}$-alkyl, $C_{3-36}$-alkenyl and $C_{3-36}$-alkynyl, wherein $C_{1-36}$-alkyl, $C_{3-36}$-alkenyl and $C_{3-36}$-alkynyl can be substituted with one to twenty substituents independently selected from the group consisting of $C_{5-6}$-cycloalkyl, $C_{6-10}$-aryl, 5 to 10 membered heteroaryl, $OR^a$, $SR^a$, $Si(R^{Sia})(R^{Sib})(R^{Sic})$, —O—$Si(R^{Sia})(R^{Sib})*R^{Sic})$, halogen, and CN; and at least two $CH_2$-groups, but not adjacent $CH_2$-groups, of $C_{1-36}$-alkyl, $C_{2-36}$-alkenyl and $C_{2-36}$-alkynyl can be replaced by O or S, wherein $R^a$ is independently selected from the group consisting of H, $C_{1-20}$-alkyl, $C_{3-20}$-alkenyl, $C_{3-20}$-alkynyl, $C_{5-6}$-cycloalkyl and $C_{6-10}$-aryl $R^{Sia}$, $R^{Sib}$ and $R^{Sic}$ are independently selected from the group consisting of H, $C_{1-20}$-alkyl, $C_{2-20}$-alkenyl, $C_{2-20}$-alkynyl, $C_{5-6}$-cycloalkyl, $C_{6-10}$-aryl, —[O—$SiR^{Sid}R^{Sie}]_o$—$R^{Sif}$ wherein o is an integer from 1 to 50, $R^{Sid}$, $R^{Sie}$, $R^{Sif}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, —[O—$SiR^{Sig}R^{Sih}]_p$—$R^{Sii}$, wherein p is an integer from 1 to 50, $R^{Sig}$ $R^{Sih}$, $R^{Sii}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, O—Si$(CH_3)_3$, $C_{1-20}$-alkyl, $C_{2-20}$-alkenyl and $C_{2-20}$-alkynyl can be substituted with one to ten substituents selected from the group consisting of halogen and CN.

In particular, $R^1$ is at each occurrence unsubstituted $C_{1-36}$-alkyl.

Preferably, $R^2$, $R^{2'}$ and $R^*$ are at each occurrence selected from the group consisting of hydrogen, $C_{1-30}$-alkyl, and halogen, wherein $C_{1-30}$-alkyl can be substituted with one to ten substituents independently selected from the group consisting of $C_{5-8}$-cycloalkyl, $C_{6-14}$-aryl, 5 to 14 membered heteroaryl, $OR^e$, $OC(O)$—$R^e$, $C(O)$—$OR^e$, $C(O)$—$R^e$, $NR^eR^f$, $NR^e$—$C(O)R^f$, $C(O)$—$NR^eR^f$, $N[C(O)R^e][C(O)R^f]$, $SR^e$, halogen, CN, $SiR^{Sis}R^{Sit}R^{Siu}$ and $NO_2$; and at least two $CH_2$-groups, but not adjacent $CH_2$-groups, of $C_{1-30}$-alkyl can be replaced by O or S, wherein $R^{Sis}$, $R^{Sit}$ and $R^{siu}$ are independently from each other selected from the group consisting of H, $C_{1-20}$-alkyl, $C_{2-20}$-alkenyl, $C_{2-20}$-alkynyl, $C_{5-6}$-cycloalkyl, phenyl and O—$Si(CH_3)_3$, $R^e$ and $R^f$ are independently selected from the group consisting of H, $C_{1-20}$-alkyl, $C_{3-20}$-alkenyl, $C_{3-20}$-alkynyl, $C_{5-8}$-cycloalkyl, $C_{6-14}$-aryl, and 5 to 14 membered heteroaryl, wherein $C_{1-20}$-alkyl, $C_{3-20}$-alkenyl and $C_{3-20}$-alkynyl can be substituted with one to five substituents selected from the group consisting of $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^g$—$C(O)R^h$, $C(O)$—$NR^gR^h$, $N[C(O)R^g][C(O)R^h]$, $SR^g$, halogen, CN, and $NO_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^g$—C(O)$R^h$, C(O)—$NR^gR^h$, N[C(O)$R^g$][C(O)$R^h$], $SR^g$, halogen, CN, and $NO_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^g$, OC(O)—$R^g$, C(O)—$OR^g$, C(O)—$R^g$, $NR^gR^h$, $NR^g$—C(O)$R^h$, C(O)—$NR^gR^h$, N[C(O)$R^g$][C(O)$R^h$], $SR^g$, halogen, CN, and $NO_2$;

wherein
$R^g$ and $R^h$ are independently selected from the group consisting of H, $C_{1-10}$-alkyl, $C_{3-10}$-alkenyl and $C_{3-10}$-alkynyl,
wherein
$C_{1-10}$-alkyl, $C_{3-10}$-alkenyl and $C_{3-10}$-alkynyl can be substituted with one to five substituents selected from the group consisting of halogen, CN and $NO_2$.

More preferably, $R^2$, $R^{2'}$ and $R^*$ are at each occurrence selected from the group consisting of hydrogen, unsubstituted $C_{1-30}$-alkyl and halogen.

In particular, $R^2$, $R^{2'}$ and $R^*$ are in each occurrence hydrogen.

Preferably, n is 0, 1 or 2. More preferably, n is 0 or 1. Most preferably, n is 0.

Preferably, m is 0, 1 or 2.

In one embodiment, $L^1$ and $L^2$ are independently from each other and at each occurrence preferably selected from the group consisting of $C_{6-30}$-arylene, 5 to 30 membered heteroarylene, and

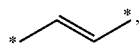

wherein
$C_{6-30}$-arylene and 5 to 30 membered heteroarylene can be substituted with one to six substituents $R^3$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, OC(O)—$R^{31}$, C(O)—$OR^{31}$, C(O)—$R^{31}$, $NR^{31}R^{32}$, $NR^{31}$—C(O)$R^{32}$, C(O)—$NR^{31}R^{32}$, $SR^{31}$, halogen, CN, $SiR^{Siv}R^{Siw}R^{Six}$ and OH, and
wherein

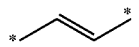

can be substituted with one or two substituents $R^4$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, C(O)—$R^{41}$, C(O)—$NR^{41}R^{42}$, C(O)—$OR^{41}$ and CN,
wherein
$R^{31}$, $R^{32}$, $R^{41}$ and $R^{42}$ are independently from each other and at each occurrence selected from the group consisting of H, $C_{2-30}$-alkenyl, $C_{2-30}$-alkynyl, $C_{5-12}$-cycloalkyl, $C_{6-18}$-aryl and 5 to 20 membered heteroaryl, and
wherein
$C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^i$, OC(O)—$R^j$, C(O)—$OR^i$, C(O)—$R^i$, $NR^iR^j$, $NR^i$—C(O)$R^j$, C(O)—$NR^iR^j$, N[C(O)$R^i$][C(O)$R^j$], $SR^i$, halogen, CN, $SiR^{Siv}R^{Siw}R^{Six}$ and $NO_2$; and at least two $CH_2$-groups, but not adjacent $CH_2$-groups of $C_{1-30}$-alkyl, $C_{2-30}$-alkenyl and $C_{2-30}$-alkynyl can be replaced by O or S, $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, OC(O)—$R^j$, C(O)—$OR^i$, C(O)—$R^i$, $NR^iR^j$, $NR^i$—C(O)$R^j$, C(O)—$NR^iR^j$, N[C(O)$R^i$][C(O)$R^j$], $SR^i$, halogen, CN, $SiR^{Siv}R^{Siw}R^{Six}$ an $NO_2$; and one or two $CH_2$-groups, but not adjacent $CH_2$-groups, of $C_{5-12}$-cycloalkyl can be replaced by O, S, OC(O), CO, $NR^i$ or $NR^i$—CO, $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, OC(O)—$R^j$, C(O)—$OR^i$, C(O)—$R^i$, $NR^iR^j$, $NR^i$—C(O)$R^j$, C(O)—$NR^iR^j$, N[C(O)$R^i$][C(O)$R^j$], $SR^i$, halogen, CN, $SiR^{Siv}R^{Siw}R^{Six}$ and $NO_2$,
wherein
$R^{Siv}$, $R^{Siw}$, $R^{Six}$ are independently from each other selected from the group consisting of H, $C_{2-20}$-alkenyl, $C_{2-20}$-alkynyl, $C_{5-6}$-cycloalkyl, phenyl and O—Si(CH_3)_3$, $R^i$ and $R^j$ are independently selected from the group consisting of H, $C_{3-20}$-alkenyl, $C_{3-20}$-alkynyl, $C_{5-8}$-cycloalkyl, $C_{6-14}$-aryl, and 5 to 14 membered heteroaryl,
wherein
$C_{1-20}$-alkyl, $C_{3-20}$-alkenyl and $C_{3-20}$-alkynyl can be substituted with one to five substituents selected from the group consisting of $C_{5-6}$-cycloalkyl, $C_{6-10}$-aryl, 5 to 10 membered heteroaryl, $OR^k$, OC(O)—$R^l$, C(O)—$OR^k$, C(O)—$R^k$, $NR^kR^l$, $NR^k$—C(O)$R^l$, C(O)—$NR^kR^l$, N[C(O)$R^k$][C(O)$R^l$], $SR^k$, halogen, CN, and $NO_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, OC(O)—$R^l$, C(O)—$OR^k$, C(O)—$R^k$, $NR^kR^l$, $NR^k$—C(O)$R^l$, C(O)—$NR^kR^l$, N[C(O)$R^k$][C(O)$R^l$], $SR^k$, halogen, CN, and $NO_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, OC(O)—$R^l$, C(O)—$OR^k$, C(O)—$R^k$, $NR^kR^l$, $NR^k$—C(O)$R^l$, C(O)—$NR^kR^l$, N[C(O)$R^k$][C(O)$R^l$], $SR^k$, halogen, CN, and $NO_2$;
wherein
$R^k$ and $R^l$ are independently selected from the group consisting of H, $C_{1-10}$-alkyl, $C_{3-10}$-alkenyl and $C_{3-10}$-alkynyl,
wherein
$C_{1-10}$-alkyl, $C_{3-10}$-alkenyl and $C_{3-10}$-alkynyl can be substituted with one to five substituents selected from the group consisting of halogen, CN and $NO_2$.

Even more preferably, $L^1$ and $L^2$ are independently from each other and at each occurrence selected from the group consisting of $C_{6-30}$-arylene and 5 to 30 membered heteroarylene,
and
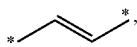
wherein $C_{6-30}$-arylene and 5 to 30 membered heteroarylene is selected from the group consisting of
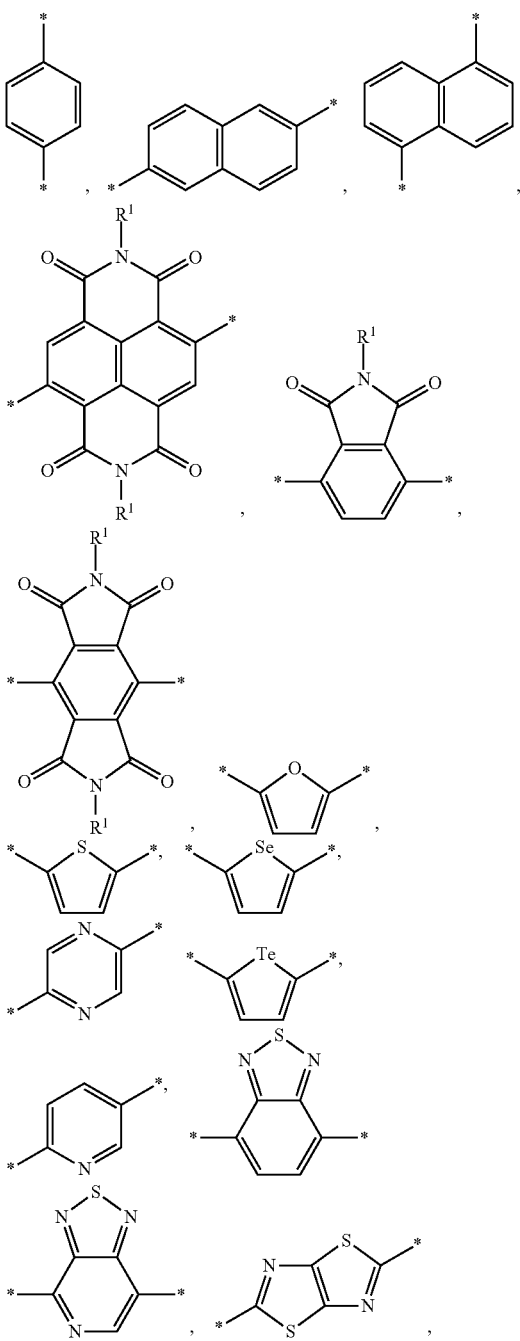
-continued
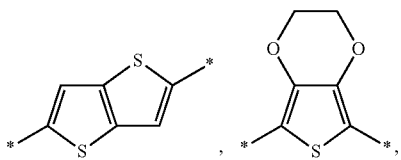
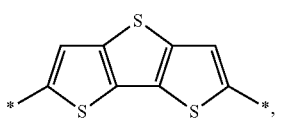
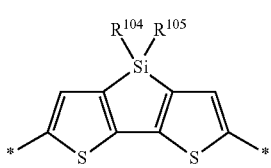
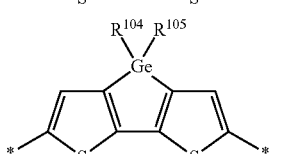
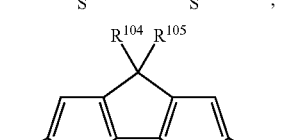
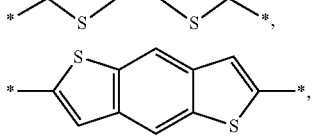
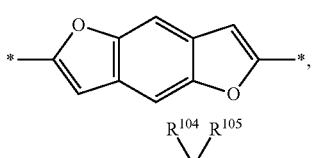
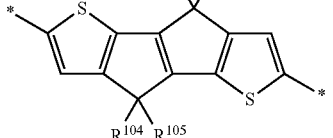
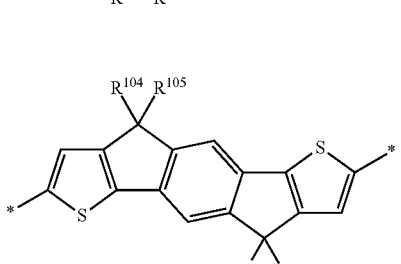
and
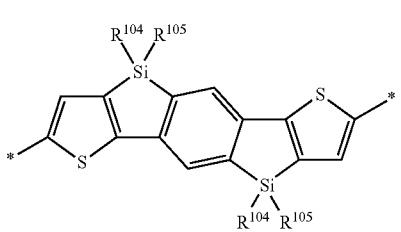

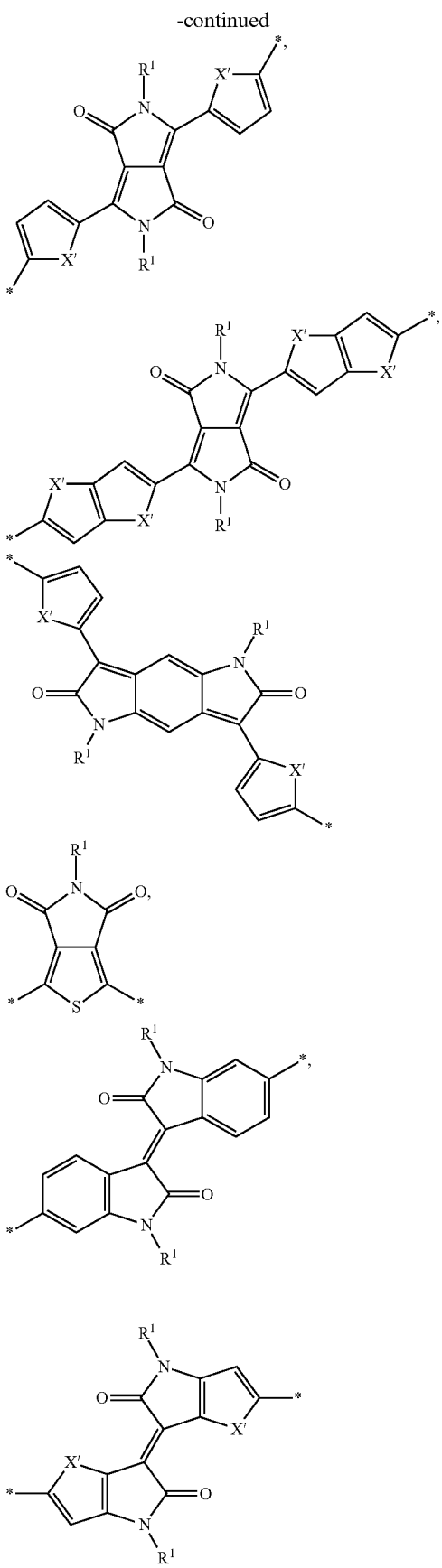

wherein
R$^{104}$ and R$^{105}$ are independently and at each occurrence selected from the group consisting of H, or C$_{1-20}$-alkyl and C$_{6-14}$-aryl,
wherein
C$_{1-20}$-alkyl can be substituted with one to five substituents selected from the group consisting of OR$^s$ and halogen;
C$_{6-14}$-aryl can be substituted with one to five substituents independently selected from the group consisting of C$_{1-10}$-alkyl, OR$^s$ and halogen;
wherein
R$^s$ is independently selected from the group consisting of H and C$_{1-10}$-alkyl,
R$^1$ is at each occurrence selected from the group consisting of C$_{1-36}$-alkyl, C$_{3-36}$-alkenyl and C$_{3-36}$-alkynyl,
wherein
C$_{1-36}$-alkyl, C$_{3-36}$-alkenyl and C$_{3-36}$-alkynyl can be substituted with one to twenty substituents independently selected from the group consisting of C$_{5-6}$-cycloalkyl, C$_{6-10}$-aryl, 5 to 10 membered heteroaryl, OR$^a$, SR$^a$, Si(R$^{Sia}$)(R$^{Sib}$)(R$^{Sic}$), —O—Si(R$^{Sia}$)(R$^{Sib}$)(R$^{Sic}$), halogen, and CN; and at least two CH$_2$-groups, but not adjacent CH$_2$-groups, of C$_{1-36}$-alkyl, C$_{2-36}$-alkenyl and C$_{2-36}$-alkynyl can be replaced by O or S,
wherein
R$^a$ is independently selected from the group consisting of H, C$_{1-20}$-alkyl, C$_{3-20}$-alkenyl, C$_{3-20}$-alkynyl, C$_{5-6}$-cycloalkyl and C$_{6-10}$-aryl
R$^{Sia}$, R$^{Sib}$ and R$^{Sic}$ are independently selected from the group consisting of H, C$_{1-20}$-alkyl, C$_{2-20}$-alkenyl, C$_{2-20}$-alkynyl, C$_{5-6}$-cycloalkyl, C$_{6-10}$-aryl, —[O—SiR$^{Sid}$R$^{Sie}$]$_o$—R$^{Sif}$
wherein
o is an integer from 1 to 50,
R$^{Sid}$, R$^{Sie}$, R$^{Sif}$ are independetly selected from the group consisting of H, C$_{1-30}$-alkyl, C$_{2-20}$-alkenyl, C$_{2-20}$-alkynyl, C$_{5-6}$-cycloalkyl, C$_{6-10}$-aryl, —[O—SiR$^{Sig}$R$^{Sih}$]$_p$—R$^{Sii}$,
wherein
p is an integer from 1 to 50,
R$^{Sig}$, R$^{Sih}$, R$^{Sii}$ are independently selected from the group consisting of H, C$_{1-30}$-alkyl, C$_{2-20}$-alkenyl, C$_{2-20}$-alkynyl, C$_{5-6}$-cycloalkyl, C$_{6-10}$-aryl, O—Si(CH$_3$)$_3$,
C$_{1-20}$-alkyl, C$_{2-20}$-alkenyl and C$_{2-20}$-alkynyl can be substituted with one to ten substituents selected from the group consisting of halogen and CN.
wherein
C$_{6-30}$-arylene and 5 to 30 membered heteroarylene can be substituted with one to six substituents R$^3$ at each occurrence selected from the group consisting of C$_{1-30}$-alkyl, C$_{1-30}$-alkoxy, CN and halogen, and
wherein

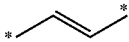

can be substituted with one or two substituents R$^4$ at each occurrence selected from the group consisting of C$_{1-30}$-alkyl, C(O)—R$^{41}$, C(O)—OR$^{41}$ and CN,
wherein
R$^{41}$ is at each occurrence C$_{1-30}$-alkyl.
Most preferably, L$^1$ and L$^2$ are independently from each other and at each occurrence C$_{6-30}$-arylene and 5 to 30 membered heteroarylene and
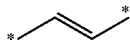
wherein $C_{6-30}$-arylene and 5 to 30 membered heteroarylene is selected from the group consisting of
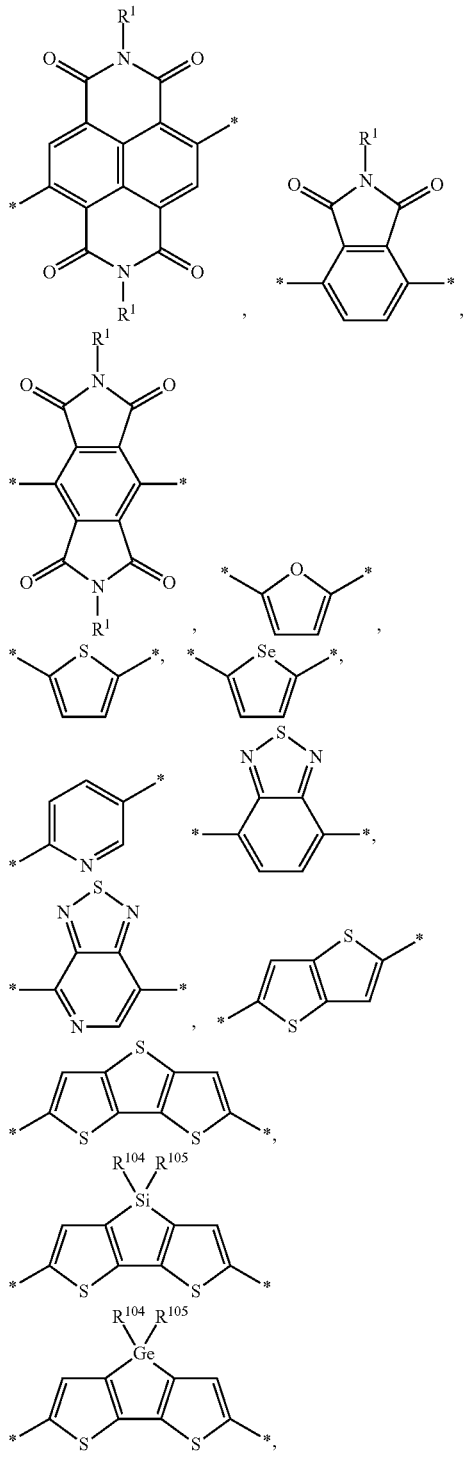
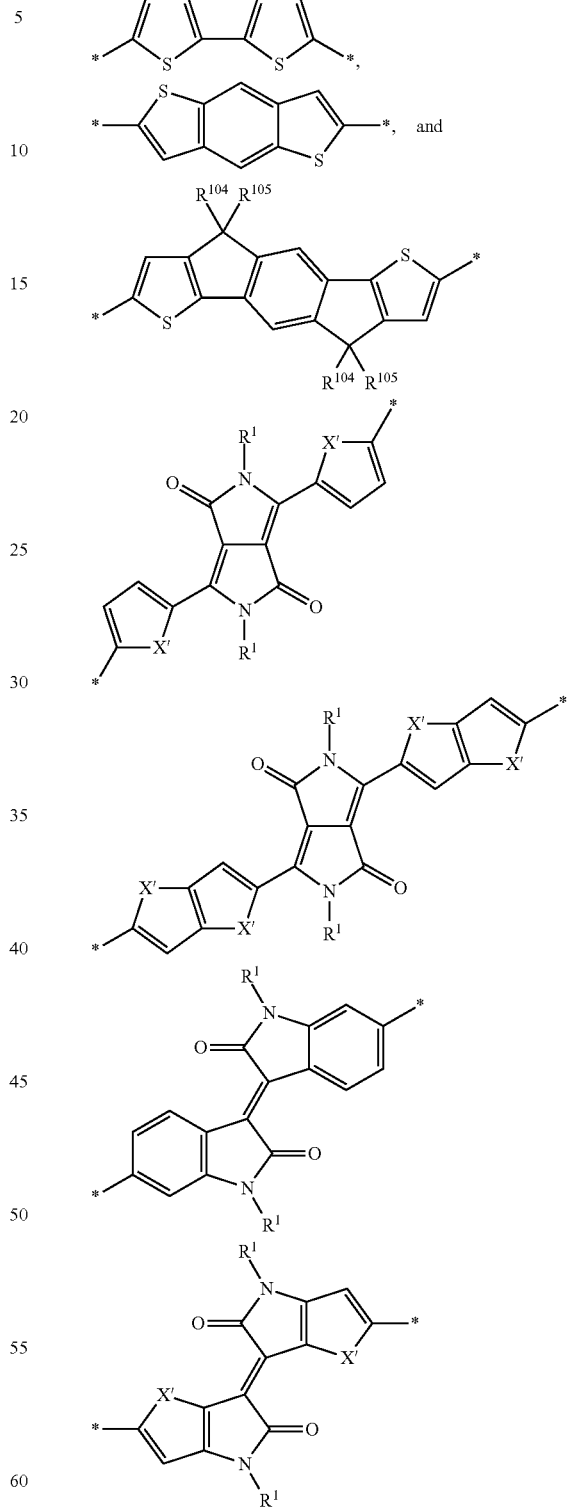
wherein
  $R^{104}$ and $R^{105}$ are independently and at each occurrence selected from the group consisting of H and $C_{1-20}$-alkyl, X' is O, S, or Se, R¹ are independently and at each occurrence a group $C_{1-36}$-alkyl, wherein 5 to 30 membered heteroarylene can be substituted with one to six substituents R³ at each occurrence selected from the group consisting of $C_{1-30}$-alkyl, $C_{1-30}$-alkoxy, CN and halogen.

wherein

[structure: *—CH=CH—*]

is unsubtituted.

In particular, L¹ and L² are independently from each other and at each occurrence $C_{6-30}$-arylene and 5 to 30 membered heteroarylene and

[structure: *—CH=CH—*]

wherein $C_{6-30}$-arylene and 5 to 30 membered heteroarylene is selected from the group consisting of

[structures: naphthalene diimide with R¹ groups; thiophene; selenophene; benzothiadiazole; dithienothiophene; benzothiadiazole; DPP (diketopyrrolopyrrole) with X' and R¹ groups]

-continued

[structures: isoindigo with R¹ groups; bis-pyrrolinone with X' and R¹ groups]

wherein
5 to 30 membered heteroarylene is unsubstituted,
X' is O, S, or Se,
R¹ are independently and at each occurrence a group $C_{1-36}$-alkyl, In preferred polymers comprising at least one unit of formula (1)
wherein
n is 0, 1, 2 or 3,
m is 0, 1, 2 or 3, and
L¹ and L² are independently from each other and at each occurrence selected from the group consisting of $C_{6-18}$-arylene, 5 to 30 membered heteroarylene,
and

[structure: *—CH=CH—*]

wherein
$C_{6-30}$-arylene and 5 to 30 membered heteroarylene can be substituted with one to six substituents R³ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)-R^{31}$, $C(O)-OR^{31}$, $C(O)-R^{31}$, $NR^{31}R^{32}$, $NR^{31}-C(O)R^{32}$, $C(O)-NR^{31}R^{32}$, $SR^{31}$, halogen, CN, $SiR^{Siv}R^{Siw}R^{Six}$ and OH, and wherein

[structure: *—CH=CH—*]

ccan be substituted with one or two substituents R⁴ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)-R^{41}$, $C(O)-NR^{41}R^{42}$, $OR^{41}$ and CN, wherein
$R^{31}$, $R^{32}$, $R^{41}$ and $R^{42}$ are independently from each other and at each occurrence selected from the group consisting of H, $C_{2-30}$-alkenyl, $C_{2-30}$-alkynyl, $C_{5-12}$-cycloalkyl, $C_{6-18}$-aryl and 5 to 20 membered heteroaryl, and wherein $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^j$, $C(O)-NR^iR^j$, $N[C(O)R^i][C(O)R^j]$, $SR^i$, halogen, CN, $SiR^{Siv}R^{Siw}R^{Six}$ and $NO_2$; and at least two $CH_2$-groups, but not adjacent $CH_2$-groups of $C_{1-30}$-alkyl, $C_{2-30}$-alkenyl and $C_{2-30}$-alkynyl can be replaced by O or S, $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, $OC(O)-R^j$, $C(O)-ORi \cdot C(O)-R^j$, $NR^iR^j$, $NR^i-C(O)R^j$, $C(O)-NR^iR^j$, $N[C(O)R^i][C(O)R^j]$, $SR^i$, halogen, CN, $SiR^{Siv}R^{Siw}R^{Six}$ and $NO_2$; and one or two $CH_2$-groups, but not adjacent $CH_2$-groups, of $C_{5-12}$-cycloalkyl can be replaced by O, S, CO(O), CO, $NR^i$ or $NR^i-CO$, $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^j$, $C(O)-NR^iR^j$, $N[C(O)R^i][C(O)R^j]$, $SR^i$, halogen, CN, $SiR^{Siv}R^{Siw}R^{Six}$ and $NO_2$, wherein $R^{Siv}$, $R^{Siw}$, $R^{Six}$ are independently from each other selected from the group consisting of H, $C_{2-20}$-alkenyl, $C_{2-20}$-alkynyl, $C_{5-6}$-cycloalkyl, phenyl and $O-Si(CH_3)_3$, $R^i$ and $R^j$ are independently selected from the group consisting of H, $C_{1-20}$-alkyl, $C_{2-20}$-alkenyl, $C_{2-20}$-alkynyl, $C_{6-8}$-cycloalkyl, $C_{6-14}$-aryl, and 5 to 14 membered heteroaryl, wherein $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^k$, $OC(O)-R^l$, $C(O)-OR^k$, $C(O)-R^k$, $NR^kR^l$, $NR^k-C(O)R^l$, $C(O)-NR^kR^l$, $N[C(O)R^k][C(O)R^l]$, $SR^k$, halogen, CN, and $NO_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)-R^l$, $C(O)-OR^k$, $C(O)-R^k$, $NR^kR^l$, $NR^k-C(O)R^l$, $C(O)-NR^kR^l$, $N[C(O)R^k][C(O)R^l]$, $SR^k$, halogen, CN, and $NO_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)-R^l$, $C(O)-OR^k$, $C(O)-R^k$, $NR^kR^l$, $NR^k-C(O)R^l$, $C(O)-NR^kR^l$, $N[C(O)R^k][C(O)R^l]$, $SR^k$, halogen, CN, and $NO_2$;

wherein $R^k$ and $R^l$ are independently selected from the group consisting of H, $C_{1-10}$-alkyl, $C_{2-10}$-alkenyl and $C_{2-10}$-alkynyl, wherein $C_{1-10}$-alkenyl and $C_{2-10}$-alkynyl can be substituted with one to five substituents selected from the group consisting of halogen, CN and $NO_2$.

$R^2$ is at each occurrence selected from the group consisting of hydrogen, unsubstituted $C_{1-30}$-alkyl and halogen, $L^1$ and $L^2$ are independently from each other and at each occurrence selected from the group consisting of 5 to 30 membered heteroarylene, and

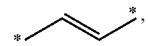

wherein 5 to 30 membered heteroarylene can be substituted with one to six substituents $R^3$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)-R^{31}$, $C(O)-OR^{31}$, $C(O)-R^{31}$, $NR^{31}R^{32}$, $NR^{31}-C(O)R^{32}$, $C(O)-NR^{31}R^{32}$, $SR^{31}$ halogen, CN, $SiR^{Siv}R^{Siw}R^{Six}$ and OH, and wherein

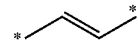

can be substituted with one or two substituents $R^4$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)-R^{41}$, $C(O)-NR^{41}R^{42}$, $OR^{41}$ and CN, wherein $R^{31}$, $R^{32}$, $R^{41}$ and $R^{42}$ are independently from each other and at each occurrence selected from the group consisting of H, $C_{2-30}$-alkenyl, $C_{2-30}$-alkynyl, $C_{5-12}$-cycloalkyl, $C_{6-18}$-aryl and 5 to 20 membered heteroaryl, and wherein $C_{1-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^{ij}C(O)-NR^iR^j$, $N[C(O)R^i][C(O)R^j]$, $SR^i$, halogen, CN, $SiR^{Siv}R^{Siw}R^{Six}$ and $NO_2$; and at least two $CH_2$-groups, but not adjacent $CH_2$-groups of $C_{1-30}$-alkyl, $C_{2-30}$-alkenyl and $C_{2-30}$-alkynyl can be replaced by O or S, $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^j$, $C(O)-NR^iR^j$, $N[C(O)R^i][C(O)R^j]$, $SR^i$, halogen, CN, $SiR^{Siv}R^{Siw}R^{Six}$ and $NO_2$; and one or two $CH_2$-groups, but not adjacent $CH_2$-groups, of $C_{5-12}$-cycloalkyl can be replaced by O, S, OC(O), CO, $NR^i$ or $NR^i-CO$, In even more preferred polymers comprising at least one unit of formula (1)

$R^1$ is at each occurrence selected from the group consisting of $C_{1-36}$-alkyl, $C_{2-36}$-alkenyl and $C_{2-6}$-alkynyl, wherein C$_{1-36}$-alkyl, C$_{2-36}$-alkenyl and C$_{2-36}$-alkynyl can be substituted with one to twenty substituents independently selected from the group consisting of C$_{5-6}$-cycloalkyl, C$_{6-10}$-aryl, 5 to 10 membered heteroaryl, OR$^a$, SR$^a$, Si(R$^{Sia}$)(R$^{Sib}$)(R$^{Sic}$), —O—Si(R$^{Sia}$)(R$^{Sib}$)(R$^{Sic}$), halogen, and CN; and at least two CH$_2$-groups, but not adjacent CH$_2$-groups, of C$_{1-36}$-alkyl, C$_{2-36}$-alkenyl and C$_{2-6}$-alkynyl can be replaced by O or S, wherein R$^a$ and Rb are independently selected from the group consisting of H, C$_{1-20}$-alkyl, C$_{2-20}$-alkenyl, C$_{2-20}$-alkynyl, C$_{5-6}$-cycloalkyl and C$_{6-10}$-aryl R$^{Siad}$, R$^{Sib}$ and R$^{Sic}$ are independently selected from the group consisting of H, C$_{1-20}$-alkyl, C$_{2-20}$-alkenyl, C$_{2-20}$-alkynyl, C$_{5-6}$-cycloalkyl, C$_{6-10}$-aryl, —[O—SiR$^{Sid}$R$^{Sie}$]$_o$—R$^{Sif}$ wherein o is an integer from 1 to 50, R$^{Sid}$, R$^{Sie}$, R$^{Sif}$ are independently selected from the group consisting of H, C$_{1-30}$-alkyl, C$_{2-20}$-alkenyl, C$_{2-20}$-alkynyl, C$_{5-6}$-cycloalkyl, C$_{6-10}$-aryl, —[O—SiR$^{Sig}$R$^{Sih}$]$_p$—R$^{Sii}$, wherein p is an integer from 1 to 50, R$^{Sig}$ R$^{Sih}$, R$^{Sii}$ are independently selected from the group consisting of H, C$_{1-30}$-alkyl, C$_{2-20}$-alkenyl, C$_{2-20}$-alkynyl, C$_{5-6}$-cycloalkyl, C$_{6-10}$-aryl, O—Si(CH$_3$)$_3$, C$_{1-20}$-alkyl, C$_{2-20}$-alkenyl and C$_{2-20}$-alkynyl can be substituted with one to ten substituents selected from the group consisting of halogen and CN, R$^2$ is at each occurrence selected from the group consisting of unsubstituted hydrogen, C$_{1-30}$-alkyl and halogen, n is 0 or 1, m is 0, 1 or 2, and L$^1$ and L$^2$ are independently from each other and at each occurrence selected from the group consisting of 5 to 30 membered heteroarylene, and

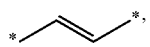

wherein 5 to 30 membered heteroarylene is selected from the group consisting of

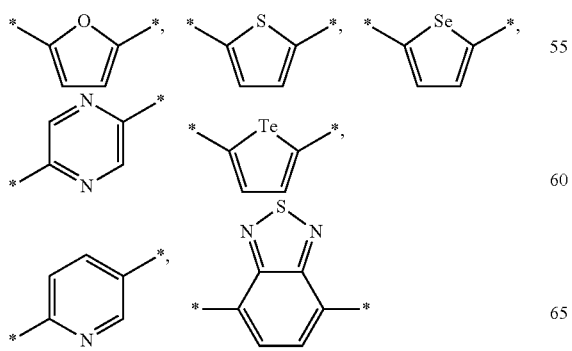

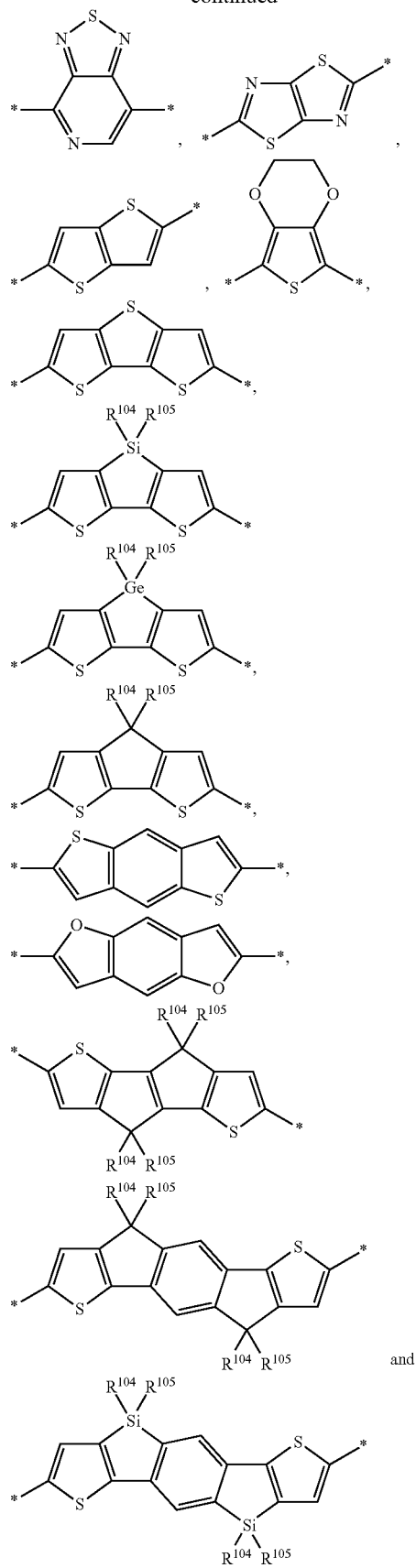

and wherein
- R[104] and R[105] are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or R[104] and R[105], if attached to the same atom, together with the atom, to which they are attached, form a 5 to 12 membered ring system, wherein
- $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
- $C_{5-8}l$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
- $C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$-$NR^sR^t$, $N[C(O)R^s][C(O)R^t]$, $SR^s$, halogen, CN, and $NO_2$;
- 5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;

wherein
- $R^s$ and $R^t$ are independently selected from the group consisting of H, $C_{1-10}$-alkyl, $C_{2-10}$-alkenyl and $C_{2-10}$-alkynyl, wherein
- $C_{1-10}$-alkyl, $C_{2-10}$-alkenyl and $C_{2-10}$-alkynyl can be substituted with one to five substituents selected from the group consisting of halogen, CN and $NO_2$, wherein
- 5 to 30 membered heteroarylene can be substituted with one to six substituents $R^3$ at each occurrence selected from the group consisting of $C_{1-30}$-alkyl and halogen, and wherein

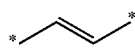

can be substituted with one or two substituents $R^4$ at each occurrence selected from the group consisting of $C_{1-30}$-alkyl, $C(O)$—$R^{41}$, $C(O)$—$OR^{41}$ and CN, wherein
- $R^{41}$ is at each occurrence $C_{1-30}$-alkyl.

In most preferred polymers comprising at least one unit of formula (1)
- $R^1$ is at each occurrence unsubstituted $C_{1-36}$-alkyl,
- $R^2$ is hydrogen,
- n is 0,
- m is 0, 1 or 2, and
- $L^1$ and $L^2$ are independently from each other and at each occurrence 5 to 30 membered heteroarylene, wherein 5 to 30 membered heteroarylene is selected from the group consisting of

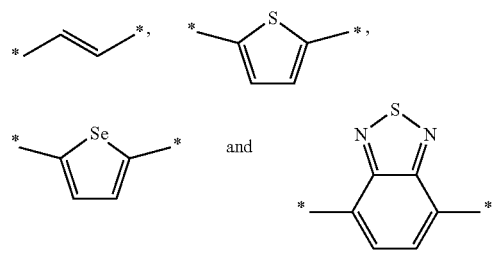

wherein
5 to 30 membered heteroarylene is unsubstituted.

In another preferred embodiment $L_1$ and $L_2$ are selected from

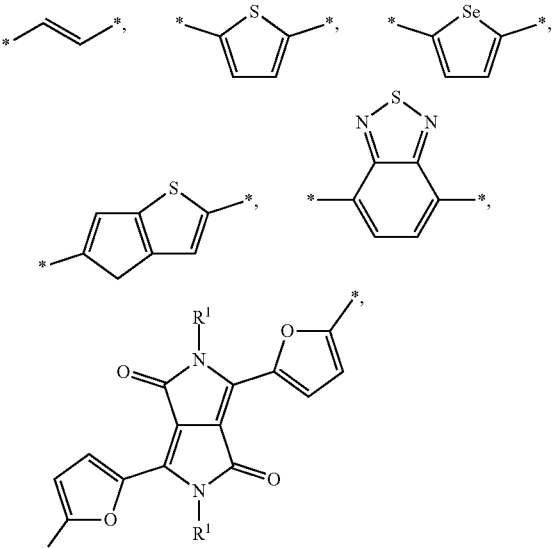

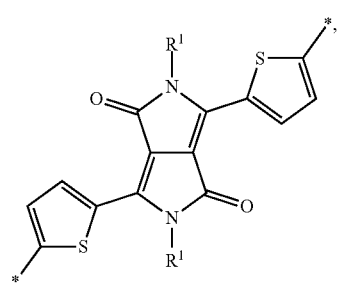

47
-continued
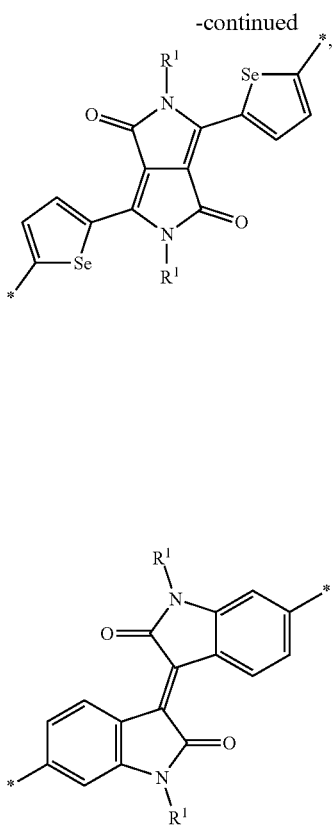
48
-continued
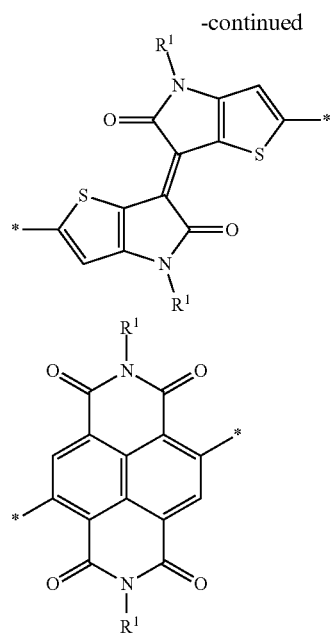
and
wherein
R¹ is at each occurrence unsubstituted $C_{1-36}$-alkyl,
R³ and R⁴ is hydrogen,
n is 0, 1 or 2
m is 0, 1 or 2
Particular preferred polymers of the present invention comprise at least one unit of formula
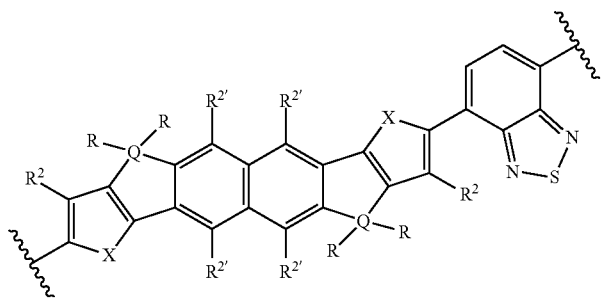
(1a)
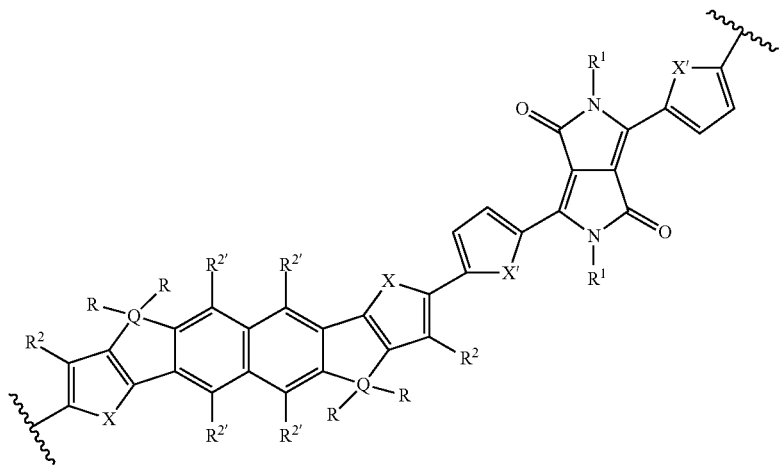
(1b)

-continued

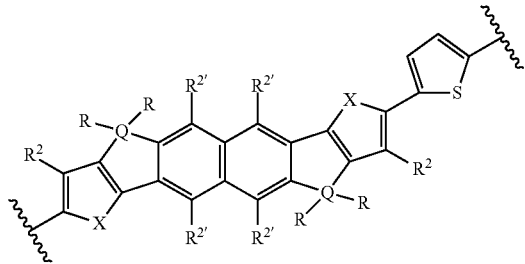 (1c)

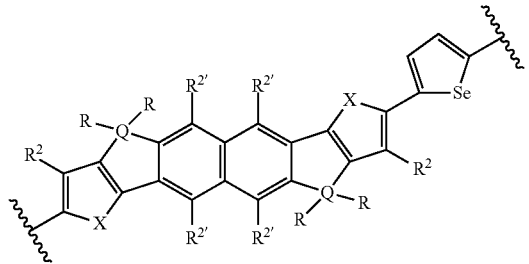 (1d)

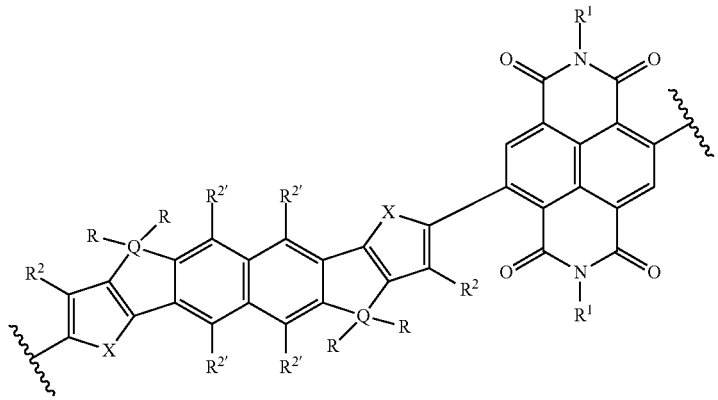 (1e)

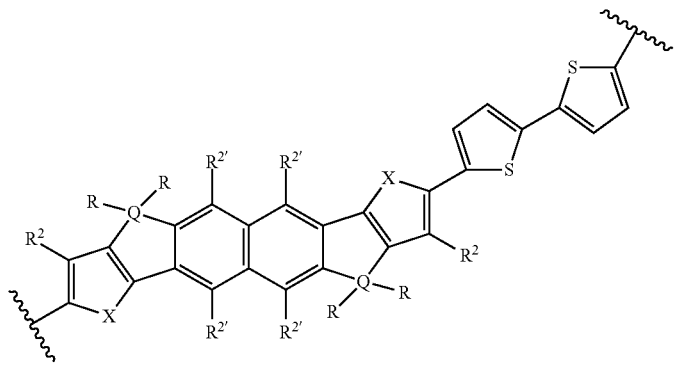 (1f)

or

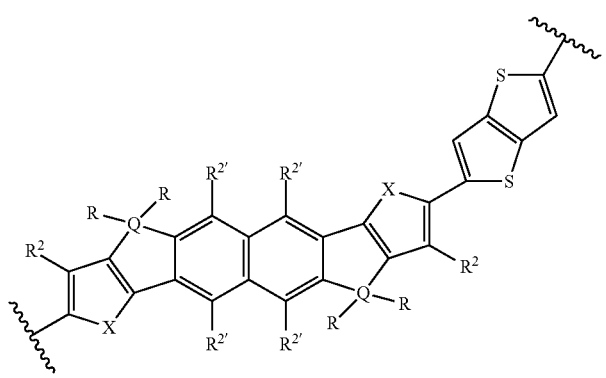 (1g)

wherein Q, R, R¹, R² and R²' are defined as above,

R is preferably at each occurrence $C_{1-30}$-alkyl, especially $C_{1-12}$-alkyl, R² and R²' are at each occurrence preferably hydrogen, Q is preferably at each occurrence carbon, X is preferably at each occurrence S, X' is preferably at each occurrence S or Se, especially S, R¹ is preferably at each occurrence unsubstituted $C_{1-36}$-alkyl.

The polymers of the present invention have preferably a weight average molecular weight ($M_w$) of 1 to 10000 kDa and a number average molecular weight ($M_n$) of 1 to 10000 kDa. The polymers of the present invention have more preferably a weight average molecular weight ($M_w$) of 1 to 1000 kDa and a number average molecular weight ($M_n$) of 1 to 100 kDa. The polymers of the present invention have most preferably a weight average molecular weight ($M_w$) of 10 to 100 kDa and a number average molecular weight ($M_n$) of 5 to 60 kDa. The weight average molecular weight ($M_w$) and the number average molecular weight ($M_n$) can be determined by gel permeation chromatography (GPC) e.g. at 80° C. using chlorobenzene or preferably at 150° C. using trichlorobenzene as eluent and a polystyrene as standard.

The polymers of the present invention can be prepared by methods known in the art.

For examples, polymers of the present invention comprising at least one unit of formula (1), wherein n is 0 and which are of formula (1-I)

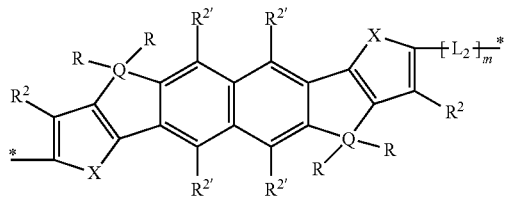
(1-I)

wherein
R, $R^2$, $R^{2'}$, $R^3$, $R^4$ and $L^2$ are as defined above,
m is 0, 1, 2, 3 or 4,
can be prepared by reacting a compound of formula (2)

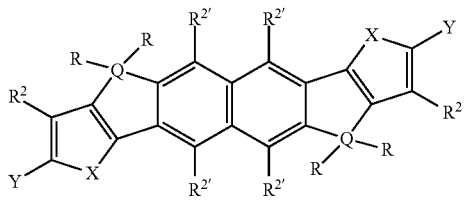
(2)

wherein Y is at each occurrence I, Br, Cl or O—S(O)$_2$CF$_3$, and R, $R^2$ and $R^{2'}$ are as defined above,
with one mol equivalents of a compound of formula (3)

$$Z^a\text{+}L_2\text{+}_m Z^b \quad (3)$$

wherein
$L^2$ is as defined for the compound of formula (1-I), and
$Z^a$ and $Z^b$ are independently selected from the group consisting of B(O$Z^1$)(O$Z^2$), SnZ$^1$Z$^2$Z$^3$,

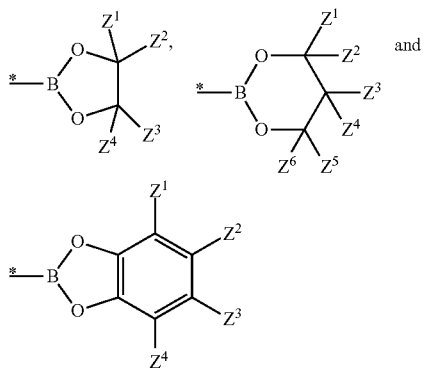
and wherein $Z^1$, $Z^2$, $Z^3$, $Z^4$, $Z^5$ and $Z^6$ are independently from each other and at each occurrence H or C$_{1-4}$-alkyl.

The polymer comprising a compound of formula (1-I) can also be obtained in analogy from compounds (2') and (3'), where the meaning of R, $R^2$, $R^{2'}$, Q, X, $L^2$, Y, $Z^a$ and $Z^b$ is defined above:

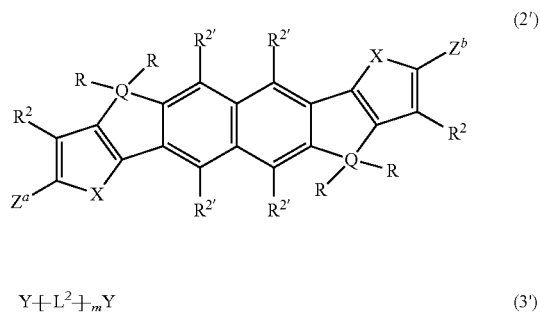
(2')

$$Y\text{+}L^2\text{+}_m Y \quad (3')$$

For example, polymers of the present invention comprising at least one unit of formula (1), wherein n and m are 0 and which are of formula (1-II)

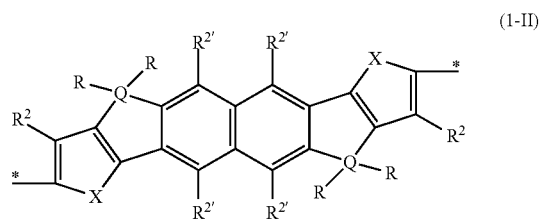
(1-II)

wherein
R, $R^2$ and $R^{2'}$ are as defined above
can be prepared by reacting a compound of formula (2)

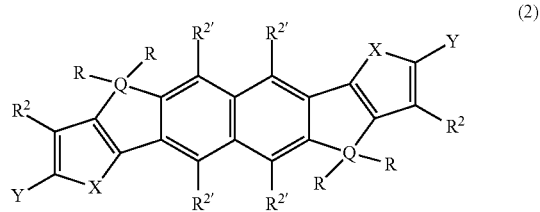
(2)

wherein Y is at each occurrence I, Br, Cl or O—S(O)$_2$CF$_3$, and R, $R^2$ and $R^{2'}$ are as defined above,
with a compound of formula (2')

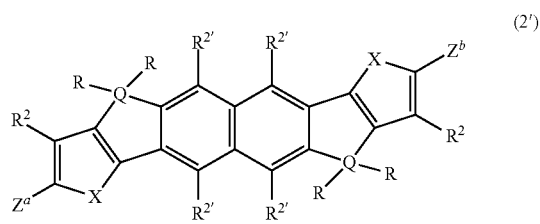
(2')

wherein
R, $R^2$ and $R^{2'}$ are as defined for the compound of formula (1-II), and $Z^a$ and $Z^b$ are independently selected from the group consisting of $B(OZ^1)(OZ^2)$, $SnZ^1Z^2Z^3$,

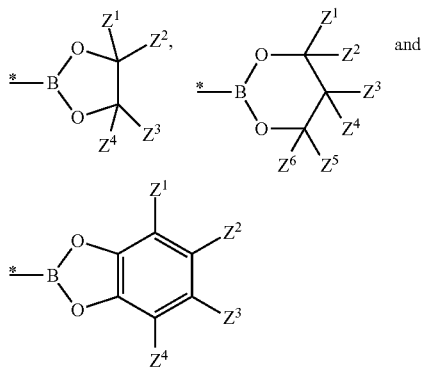

wherein $Z^1$, $Z^2$, $Z^3$, $Z^4$, $Z^5$ and $Z^6$ are independently from each other and at each occurence H or $C_{1-4}$-alkyl.

When $Z^a$ and $Z^b$ are independently selected from the group consisting of $B(OZ^1)(OZ^2)$,

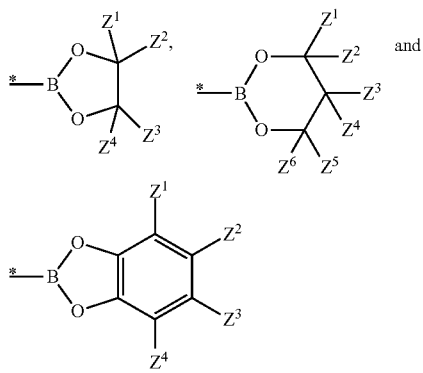

wherein $Z^1$, $Z^2$, $Z^3$, $Z^4$, $Z^5$ and $Z^6$ are independently from each other and at each occurrence H or $C_{1-4}$-alkyl, the reaction is usually performed in the presence of a catalyst, preferably a Pd catalyst such as $Pd(P(Ph)_3)_4$, $Pd(OAc)_2$ and $Pd_2(dba)_3$, and a base such as $K_3PO_4$, $Na_2CO_3$, $K_2O_3$, LiOH and NaOMe. Depending on the Pd catalyst, the reaction may also require the presence of a phosphine ligand such as $P(Ph)_3$, $P(o\text{-tolyl})_3$ and $P(tert\text{-Bu})_3$. The reaction is also usually performed at elevated temperatures, such as at temperatures in the range of 40 to 250° C., preferably 60 to 200° C. The reaction can be performed in the presence of a suitable solvent such as tetrahydrofuran, toluene or chlorobenzene. The reaction is usually performed under inert gas.

When $Z^a$ and $Z^b$ are independently $SnZ^1Z^2Z^3$, wherein $Z^1$, $Z^2$ and $Z^3$ are independently from each other $C_{1-4}$-alkyl, the reaction is usually performed in the presence of a catalyst, preferably a Pd catalyst such as $Pd(P(Ph)_3)_4$ and $Pd_2(dba)_3$. Depending on the Pd catalyst, the reaction may also require the presence of a phosphine ligand such as $P(Ph)_3$, $P(o\text{-tolyl})_3$ and $P(tert\text{-Bu})_3$. The reaction is also usually performed at elevated temperatures, such as at temperatures in the range of 40 to 250° C., preferably 60 to 200° C. The reaction can be performed in the presence of a suitable solvent such as toluene or chlorobenzene. The reaction is usually performed under inert gas.

The compound of formula (2) can be prepared by methods known in the art from a compound of formula (4).

For examples, compounds of formula (2),

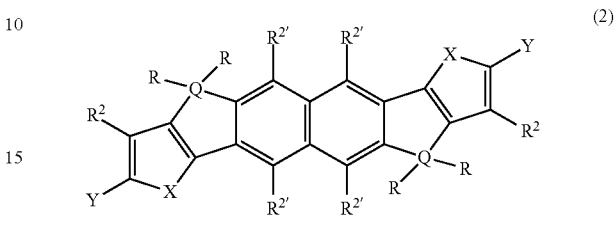

wherein Y is I, Br, Cl or O-triflate, R is at each occurrence $C_{1-30}$-alkyl, and $R^2$ and $R^{2'}$ are hydrogen, can be prepared by treating a compound of formula (4)

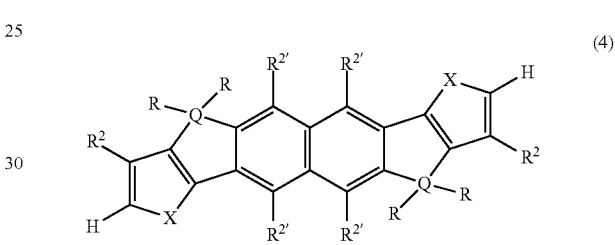

wherein R is at each occurrence $C_{1-30}$-alkyl, $R^2$ and $R^{2'}$ are hydrogen with an Y-donor.

For example, when Y is Br, the Y-donor can be N-bromosuccinimide. When using N-bromo-succinimide as Y-donor, the reaction can be performed at 0° C. in the presence of $CHCl_3$/acetic acid as solvent.

A compound of formula (4), wherein Q is a carbon atom, can be prepared by the following synthetic pathway. $R^2$, $R^{2'}$, X and R have the meaning defined above.

$R^2$ is preferably hydrogen, $R^{2'}$ is preferably hydrogen,

X is preferably O, S or Se, more preferably S or Se, especially S,

R is preferably $C_{1-30}$-alkyl, $R^L$ is defined as R, but is preferably $C_{1-29}$-alkyl;

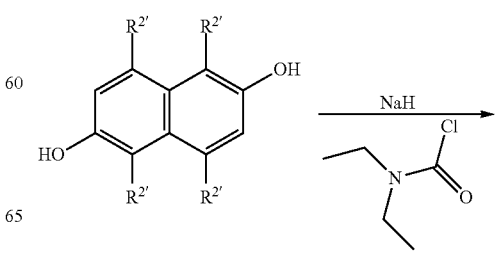

55
-continued
56
-continued
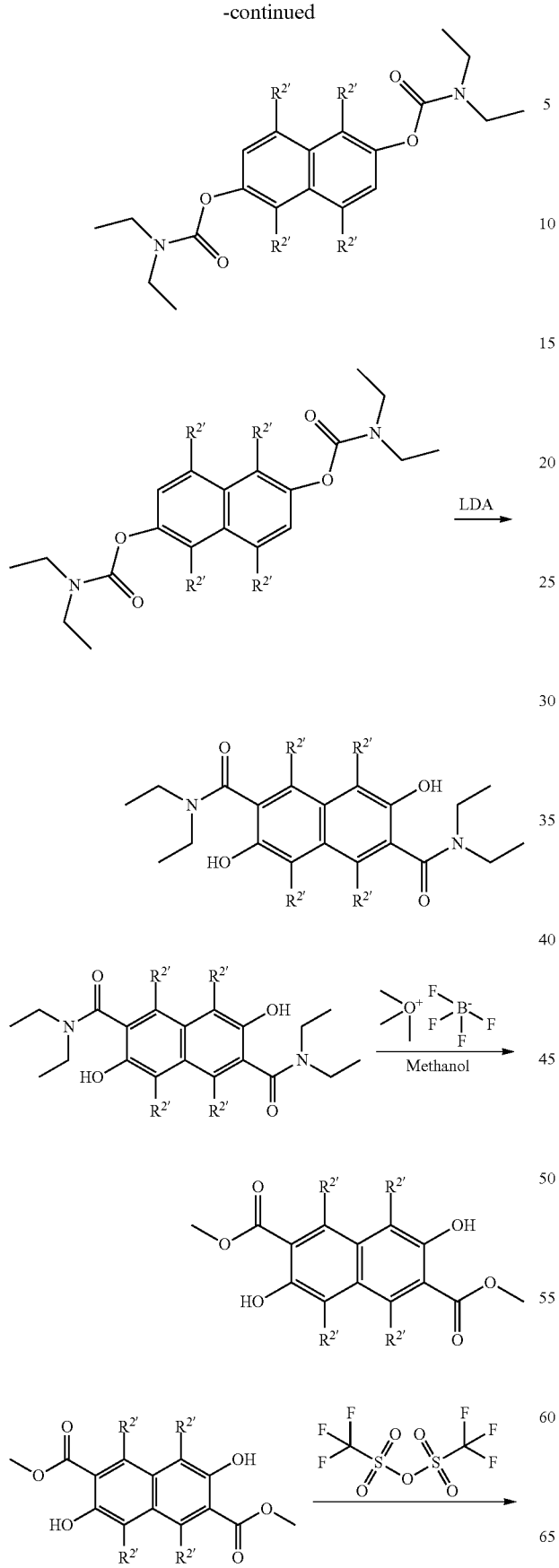
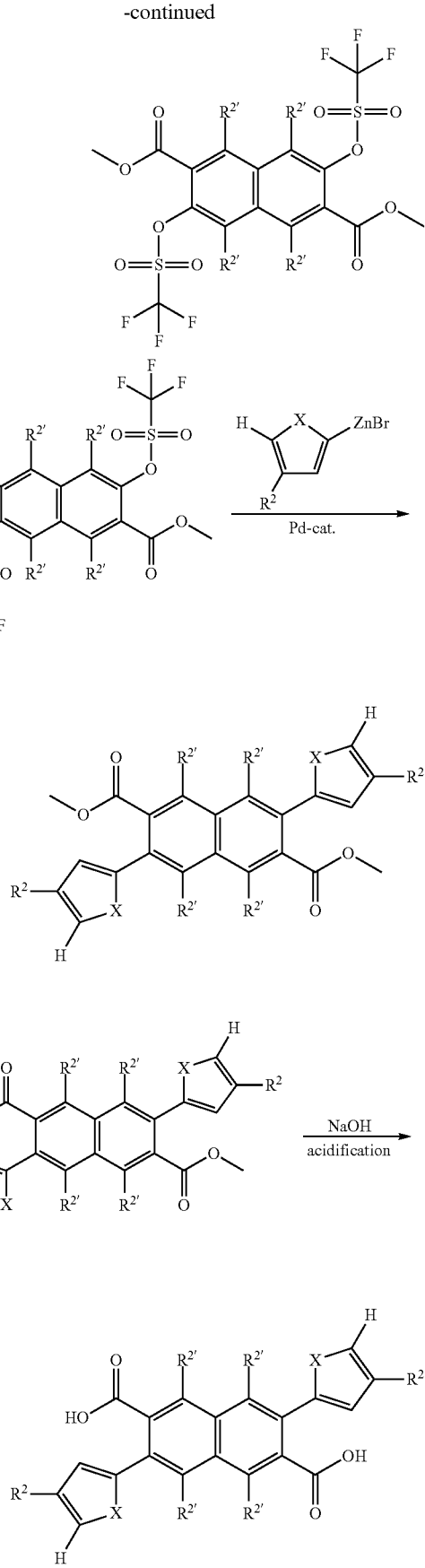

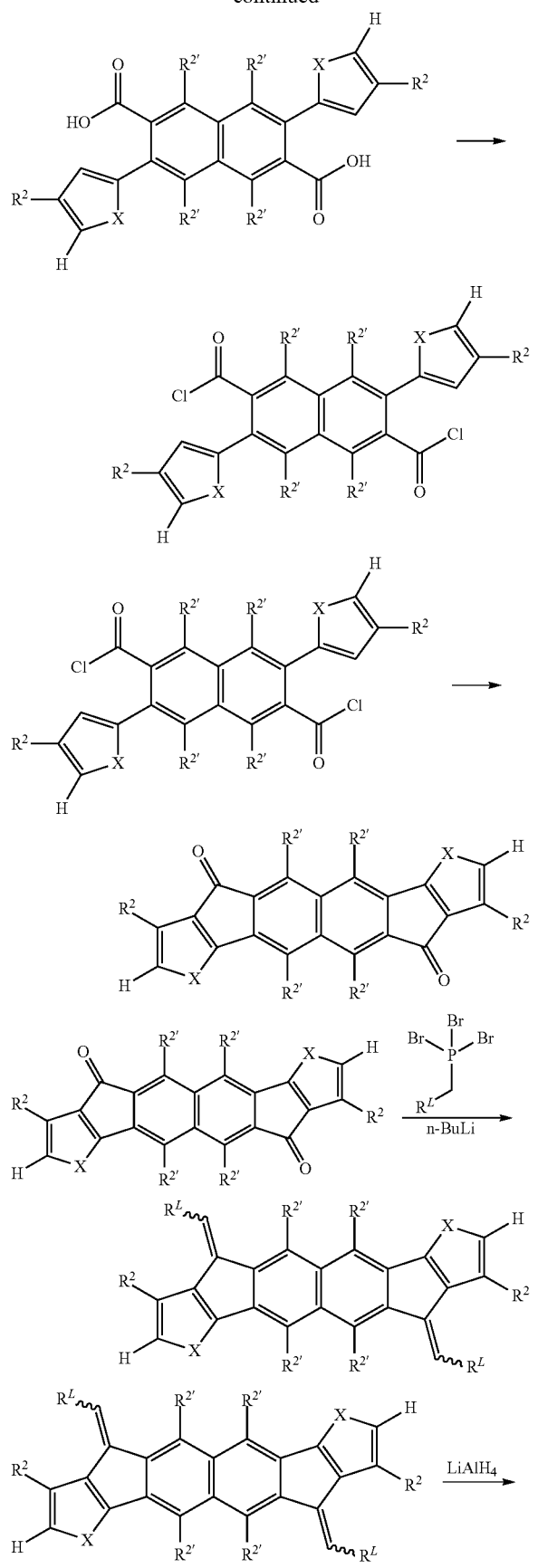

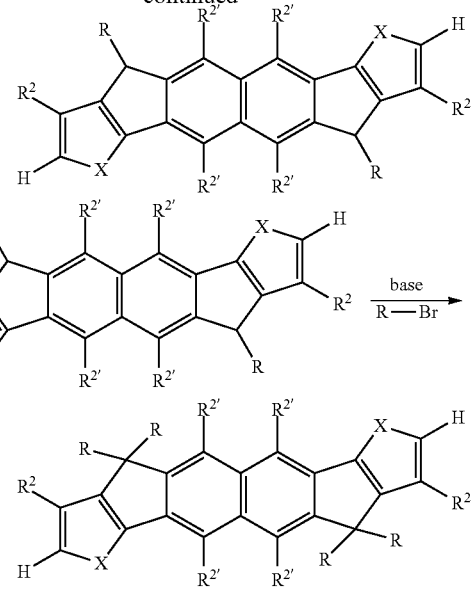

Also part of the invention are intermediates of formula

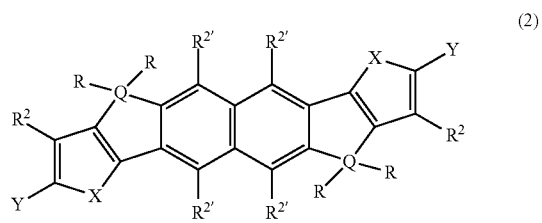
(2)

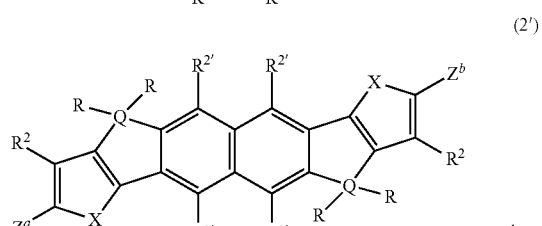
(2')

and

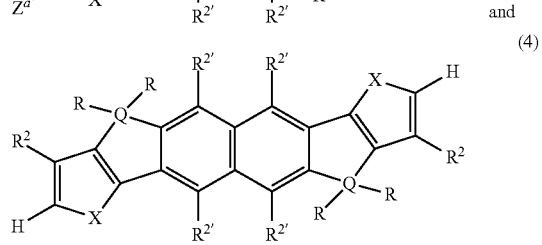
(4)

wherein
R², R²', X, Q, Z^a, Z^b and R have the meaning defined above.
Y is at each occurence I, Br, Cl or O—S(O)₂CF₃.
In preferred intermediates of formulae (2), (2') and (4) at each occurence
R² and R²' are hydrogen, unsubstituted $C_{1-30}$-alkyl or halogen;
X is O, S or Se;
Q is a carbon atom;
R is hydrogen, $C_{1-30}$-alkyl, $C_{2-30}$-alkenyl, $C_{2-30}$-alkynyl, $C_{5-12}$-cycloalkyl, or phenyl, preferably $C_{1-30}$-alkyl;
Y is at each occurence I or Br;
Z^a, Z^b are

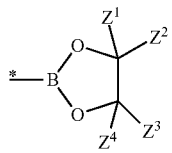

where $Z^1$-$Z^4$ are methyl.

In more preferred intermediates of formulae (2) and (4) at each occurence
$R^2$ and $R^{2'}$ are hydrogen or halogen;
X is S or Se;
Q is a carbon atom;
R is $C_{1-30}$-alkyl,
Y is I or Br;

In most preferred intermediates of formulae (2) and (4) at each occurence
$R^2$ and $R^{2'}$ are hydrogen,
X is S,
Q is a carbon atom;
R is $C_{1-30}$-alkyl,
Y is I or Br;

Particular preferred intermediates of formula (2)

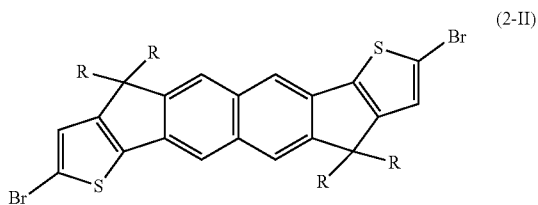

(2-II)

wherein, R is at each occurrence $C_{1-30}$-alkyl and $R^2$ is hydrogen.

Also part of the invention is an electronic device comprising the polymer of the present invention.

The electronic device can be an organic photovoltaic device (OPVs), an organic field-effect transistor (OFETs), an organic light emitting diode (OLEDs) or an organic photodiode (OPDs).

Preferably, the electronic device is an organic photovoltaic device (OPVs), an organic field-effect transistor (OFETs) or an organic photodiode (OPDs).

More preferably, the electronic device is an organic field effect transistor (OFET).

Usually, an organic field effect transistor comprises a dielectric layer, a semiconducting layer and a substrate. In addition, an organic field effect transistor usually comprises a gate electrode and source/drain electrodes.

Preferably, the semiconducting layer comprises the polymer of the present invention. The semi-conducting layer can have a thickness of 5 to 500 nm, preferably of 10 to 100 nm, more preferably of 20 to 50 nm.

The dielectric layer comprises a dielectric material. The dielectric material can be silicon dioxide or aluminium oxide, or, an organic polymer such as polystyrene (PS), poly(methylmethacrylate) (PMMA), poly(4-vinylphenol) (PVP), poly(vinyl alcohol) (PVA), benzocyclobutene (BCB), or polyimide (PI). The dielectric layer can have a thickness of 10 to 2000 nm, preferably of 50 to 1000 nm, more preferably of 100 to 800 nm.

The dielectric layer can in addition to the dielectric material comprise a self-assembled monolayer of organic silane derivates or organic phosphoric acid derivatives. An example of an organic silane derivative is octyltrichlorosilane. An examples of an organic phosphoric acid derivative is octyldecylphosphoric acid. The self-assembled monolayer comprised in the dielectric layer is usually in contact with the semiconducting layer.

The source/drain electrodes can be made from any suitable organic or inorganic source/drain material. Examples of inorganic source/drain materials are gold (Au), silver (Ag) or copper (Cu), as well as alloys comprising at least one of these metals. The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide or gold (Au), or alloys comprising at least one of these metals. The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the design of the organic field effect transistor, the gate electrode, for example highly doped silicon can also function as substrate.

The organic field effect transistor can be prepared by methods known in the art.

For example, a bottom-gate top-contact organic field effect transistor can be prepared as follows: The dielectric material, for example $Al_2O_3$ or silicon dioxide, can be applied as a layer on a gate electrode such as highly doped silicon wafer, which also functions as substrate, by a suitable deposition method such as atom layer deposition or thermal evaporation. A self-assembled monolayer of an organic phosphoric acid derivative or an organic silane derivative can be applied to the layer of the dielectric material. For example, the organic phosphoric acid derivative or the organic silane derivative can be applied from solution using solution-deposition techniques. The semiconducting layer can be formed by either solution deposition or thermal evaporation in vacuo of the polymer of the present invention on the self-assembled monolayer of the organic phosphoric acid derivative or the organic silane derivative. Source/drain electrodes can be formed by deposition of a suitable source/drain material, for example tantalum (Ta) and/or gold (Au), on the semiconducting layer through a shadow masks. The channel width (W) is typically 10 to 1000 μm and the channel length (L) is typically 5 to 500 μm.

For example, a top-gate bottom-contact organic field effect transistor can be prepared as follows: Sorce/drain electrodes can be formed by evaporating a suitable source/drain material, for example gold (Au), on photo-lithographically defined electrodes on a suitable substrate, for example a glass substrate. The semiconducting layer can be formed by depositing a solution of the polymers of the present invention, for example by spin-coating, on the source/drain electrodes, followed by annealing the layer at elevated temperatures such as at a temperature in the range of 80 to 360° C. After quenching the semiconducting layer, a dielectric layer can be formed by applying, for example, by spin-coating, a solution of a suitable dielectric material such as poly(methylmethacryate), on the semiconducting layer. The gate electrode of a suitable gate material, for example gold (Au), can be evaporated through a shadow mask on the dielectric layer.

Also part of the invention is the use of the polymer of the present invention as semiconducting material.

The polymers of the present invention show high charge carrier mobilities. The polymer of the present invention can show ambipolar properties with high hole and electron mobilities. In addition, the polymers of the present invention show a high stability, in particular a high thermal stability. Furthermore the polymers of the present invention are compatible with liquid processing techniques. In addition, the polymers of the present invention show a strong absorption of the near infra-red light.

EXAMPLES

Example 1

Naphthalene-2,6-diyl bis(diethylcarbamate)

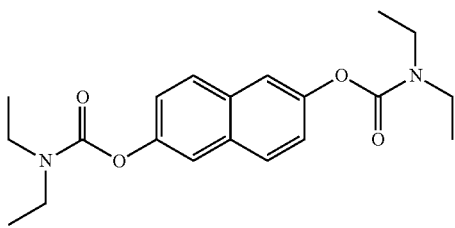 [SMILES: CCN(CC)C(=O)Oc1ccc2cc(OC(=O)N(CC)CC)ccc2c1]

10 g (62.4 mmol) of napthhalene 2,6-diol were dissolved in 100 ml of THF and added to a stirred suspension of NaH (50% in mineral oil, 9 g, 187.3 mmol, 3 equiv) in THF (80 ml) at 0° C. Then, the resulting suspension was stirred at 0° C. for one hour before 23.7 ml of diethylcarbamoyl chloride (187.3 mmol, 3 equiv.) were added dropwise. The reaction was allowed to warm up to room temperature and stirred overnight. Then, the reaction was carefully quenched by adding a few drops of water. Then, the THF was removed by distillation and the residue was extracted with $H_2O$ and ethyl acetate. The organic layer was washed with aq. KOH (1M) and $H_2O$, then dried over $MgSO_4$ and evaporated. The retrieved product could be used without further purification Yield 22.2 g (~99%)

$^1$H NMR (400 MHz, $CDCl_3$, δ) 7.77 (d, 2H), 7.57 (dd, 2H), 7.28 (dd, 2H), 3.45 (m, 8H), 1.25 (m, 12H)

$^{13}$C-NMR (100 MHz, $CDCl_3$, δ) 13.29, 14.16, 41.82, 42.16, 118.19, 122.08, 128.51, 131.37, 148.74, 154.20

Example 2

N2,N2,N6,N6-tetraethyl-3,7-dihydroxynaphthalene-2,6-dicarboxamide

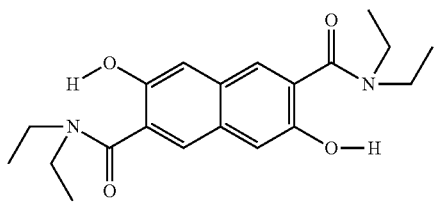 [SMILES: CCN(CC)C(=O)c1cc2cc(O)c(C(=O)N(CC)CC)cc2cc1O]

Under an argon atmosphere, 162 mL of LDA solution (323.6 mmol, 2M in THF/heptane/ethylbenzene, 5 equiv.) were slowly added via a syringe to a solution of 23.2 g (64.7 mmol, 1.0 equiv) of naphthalene-2,6-diyl bis(diethylcarbamate) in THF (600 ml) at −78° C. The resulting mixture was allowed to warm to room temperature overnight while it turned deep green. Then, the reaction mixture was carefully quenched with HCl(2M) solution, and the formed precipitate was filtered off and washed with $Et_2O$. After drying, 11.29 g (49%) of a pale yellow solid were obtained which could be used without further purification.

$^1$H NMR (400 MHz, DMSO-$d^6$, δ): 9.72 (s, 2H), 7.46, (s, 2H), 7.12 (s, 2H), 3.45 (m, 4H), 3.13 (m, 4H), 1.16 (t, 6H), 1.00 (t, 6H)

$^{13}$C-NMR (100 MHz, DMSO-$d^6$, δ): 167.6, 149.4, 129.0, 128.1, 124.4, 109.3, 44.2, 42.3, 13.9, 12.9

ESI-TOF-MS: for $C_{20}H_{27}N_2O_4$ [M+] calc'd 359.1971 found 359.1989

Example 3

3,7-Bis((tert-butyldimethylsilyl)oxy)-$N^2$, $N^2$, $N^6$, $N^6$-tetraethylnaphthalene-2,6-dicarboxamide 10.54 g $N^2,N^2$00-tetraethyl-3,7-dihydroxynaphthalene-2,6-dicarboxamide were dissolved in 50 ml of DMF and 8 g of imidazole were added. Then, TBSCl was added portionwise and the reaction mixture stirred at room temperature for 24 h. The reaction was quenched by pouring into water and the resulting white precipitate was filtered off, washed with copious amounts of water, and dried in vacuo Yield 16.85 g (98%).

$^1$H NMR (400 MHz, $CDCl_3$, δ): 7.54 (d, 2H), 7.07 (d, 2H), 3.57 (m, 2H), 3.19 (m, 2H), 1.27 (t, 3H), 1.03 (m, 3H), 0.98 (s, 18H), 0.20-0.28 (4s, 12H)

$^{13}$C-NMR (100 MHz, $CDCl_3$, δ): 168.8, 148.5, 132.4, 129.8, 125.9, 125.7, 114.7, 114.3, 43.2, 43.1, 39.5, 25.9, 18.4, 14.3, 13.5, -3.85, -3.9, -4.3, -4.4

Example 4

Dimethyl 3,7-dihydroxynaphthalene-2,6-dicarboxylate

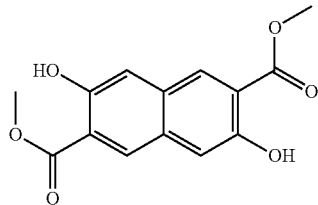 [SMILES: COC(=O)c1cc2cc(O)c(C(=O)OC)cc2cc1O]

3,7-bis((tert-butyldimethylsilypoxy)-$N^2,N^2,N^6,N^6$-tetraethylnaphthalene-2,6-dicarboxamide (16.85 g, 28.7 mmol) was dissolved in anhydrous DCM and $(CH_3)_3OBF_4$ (10.19 g, 68.9 mmol, 2.4 equiv) was added in portions. After consumption of the amide was complete, as indicated by TLC (ca. 18 h), the reaction mixture was evaporated to dryness and methanol (100 ml) was added followed by a saturated solution of $Na_2CO_3$ (100 mL) and solid $Na_2CO_3$ (1 g). The resulting mixture was filtered and acidified with HCl to a pH of 1. The formed solid was recovered by filtration as a first fraction, which could be used without further purification (2.7 g, 34%). The organic layer was dried, evaporated and purified by silica gel filtration (chloroform as eluent) to yield a second fraction (1.2 g). 49% yield were obtained in total.

$^1$H NMR (400 MHz, CDCl$_3$, δ): 10.23 (s, 2H), 8.36 (s, 2H), 7.32 (s, 2H), 4.04 (s, 6H)

$^{13}$C-NMR (100 MHz, CDCl$_3$, δ): only sparingly soluble in chloroform: 130.6 (CH, arom, naptht), 112.7 (CH, arom, naptht), 52.8 (CH$_3$)

Example 5

3,7-Bis(((trifluoromethyl)sulfonyl)oxy)naphthalene-2,6-dicarboxylic acid dimethylester

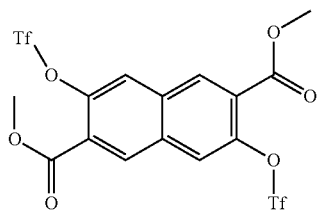

1.58 g (5.7 mmol) of dimethyl 3,7-dihydroxynaphthalene-2,6-dicarboxylate were dissolved (suspended) in DCM (50 ml) and 2.5 ml dry pyridine were added. Then, the reaction mixture was cooled to 0° C. and 2.10 ml (3.514 g, 12.5 mmol, 2.2 equiv.) of triflic anhydride were added dropwise. The reaction mixture was allowed to warm up to room temperature and was stirred overnight. Then, water (20 ml) and 2M HCl (20 ml) were added and the aqueous phase was subsequently extracted with 2×50 mL DCM. The combined organic layers were extracted with sat. NaHCO3 solution (50 ml) and brine, dried over MgSO$_4$ and evaporated to dryness. A white solid was retrieved which could be directly used for the next step. Yield: 2.63g (85%)

$^1$H NMR (400 MHz, CDCl$_3$, δ): 8.71 (s, 2H), 7.92 (s, 2H), 4.05 (s, 6H)

$^{13}$C-NMR (100 MHz, CDCl$_3$, δ): C 163.65, 146.31, 134.49, 133.19, 126.06, 122.53, 120.57, 53.42

Example 6

3,7-Di(thiophen-2-yl)naphthalene-2,6-dicarboxylic Acid Dimethylester

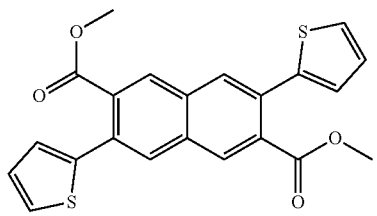 [SMILES: COC(=O)c1cc2cc(-c3cccs3)c(C(=O)OC)cc2cc1-c1cccs1]

A mixture of 3,7-bis(((trifluoromethyl)sulfonyl)oxy) naphthalene-2,6-dicarboxylic acid dimethyl-ester (2.59 g, 4.79 mmol), 2-thienylzinc bromide (0.50 M in THF, 24 ml, 12.16 mmol) and Pd(PPh$_3$)$_4$ (265 mg, 0.243 mmol) was heated to reflux for 3 h. The reaction was allowed to cool to room temperature and sat. NH$_4$Cl solution was added, after which a white precipitate formed. The product was recovered by filtration, washed with water and methanol and dried in vacuo to give dimethyl 3,7-di(thiophen-2-yl)naphthalene-2,6-dicarboxylic acid dimethyl ester as a pale yellow solid (1.62 g, 82%).

$^1$H NMR (400 MHz, CDCl$_3$, δ): 8.26 (s, 2H), 8.01 (s, 2H), 7.40 (dd, 2H), 7.12 (m, 4H), 3.81 (s, 6H).

A $^{13}$C-NMR could not be recorded due to poor solubility in chloroform.

Example 7

3,7-Di(thiophen-2-yl)naphthalene-2,6-dicarboxylic Acid

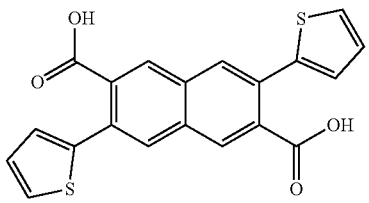 [SMILES: O=C(O)c1cc2cc(-c3cccs3)c(C(=O)O)cc2cc1-c1cccs1]

To a solution of 3,7-di(thiophen-2-yl)naphthalene-2,6-dicarboxylic acid dimethylester (1.28 g, 3.13 mmol) in ethanol (50 ml), a solution of sodium hydroxide (2.0 g NaOH in 15 ml water) was added. The reaction mixture was heated to reflux for 15 h. Then, the ethanol was removed on a rotary evaporator. The remaining aqueous solution was then acidified with concentrated hydro-chloric acid. The precipitated product was isolated by filtration, washed with water and methanol and dried in vacuo. 1.1 g (92%) of a yellow solid were obtained which could be used without further purification.

$^1$H NMR (400 MHz, DMSO-d$^6$): δ(ppm) 13.24 (2H, COOH), 8.32 (s, 2H), 8.17 (s, 2H), 7.62 (dd, 2H), 7.21 (dd, 2H), 7.13 (dd, 2H)

$^{13}$C NMR (100 MHz, DMSO-d$^6$): δ(ppm) 169.5, 141.1, 133.2, 131.7, 130.4, 129.6, 128.6, 127.8, 126.9, 126.7

Example 8

4,10-Dihydro-naphtho[3",2":3,4;7",6":3',4'] dicyclopenta[2,1-b:2',1-b'] dithiophene-4,10-dione

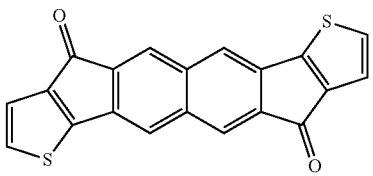 [SMILES: O=c1c2cc3cc4c(cc3cc2c2sccc12)c(=O)c1ccsc14]

To a suspension of 3,7-di(thiophen-2-yl)naphthalene-2,6-dicarboxylic acid (1.1 g, 2.89 mmol) in anhydrous DCM (50 ml), oxalyl chloride (1.48 g g, 11.56 mmol) was added, followed by drop-wise addition of anhydrous DMF (200 µl). The resultant mixture was stirred overnight at room temperature. Then, the solvents were removed in vacuo and after drying, the formed crude acid chloride (yellow solid) was redissolved in anhydrous DCM (80 ml). This solution was then added dropwise (via cannula) to a suspension of anhydrous AlCl$_3$ (2 g) in DCM (50 ml) which was cooled to 0° C. The reaction mixture was stirred overnight while being allowed to warm up to room temperature. Then, it was poured onto ice containing HCl. A red precipitate was formed which was collected by filtration and washed with 2M HCl solution, water and acetone. After drying in vacuo, a red solid was obtained (748 mg, 75%).

$^1$H NMR (400 MHz, CDCl$_3$, δ): 7.83 (s, 2H) 7.49 (s, 2H), 7.29 (d, 2H), 7.21 (d, 2H)

A $^{13}$C spectrum could not be recorded due to poor solubility.

Example 9

4,10-Bis(hexadecylidene)-4,10-dihydro-naphtho[3",2":3,4;7",6":3',4'] dicyclopenta[2,1-b:2',1'-b']dithiophene

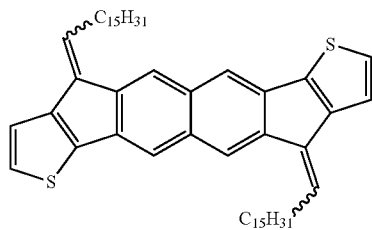

2.712 g (4.78 mmol, 2.2 equiv.) of hexadecylphosphonium tribromide were dissolved in 60 ml of THF and cooled to −78° C. Then, 3 ml (4.78, 2.2 equiv.) of n-BuLi were added dropwise with a syringe and the resulting solution was stirred for 30 min at −78° C. Then 748 mg of 4,10-dihydro-naphtho[3",2":3,4;7",6":3',4'] dicyclopenta[2,1-b:2',1'-1'] dithiophene-4,10-dione (2.17 mmol, 1 equiv) were suspended in 100 ml of THF and added dropwise via cannula.

The reaction was left at −78° C. for 1 h and then let warm up to room temperature and carefully quenched by addition of water. The aqueous phase was extracted with 2×40 ml of EtOAc, dried over MgSO$_4$ and dried in vacuo.

The residue was purified by column chromatography (PET/EtAc 20/1) and 788 mg (48% yield) of a yellow solid were obtained which contained a mixture of three diastereomers. MALDI-TOF-MS: C$_{52}$H$_{72}$S$_2$ [C$_{52}$H$_{73}$S$_2$+=MH+] calc'd 761.52 found 760.7

Example 10

4,4,10,10-Tetrakis-(hexadecyl)-4,10-dihydro-naphtho[3",2":3,4;7",6":3',4']-dicyclopenta[2,1-b:2',1'-b']-dithiophene

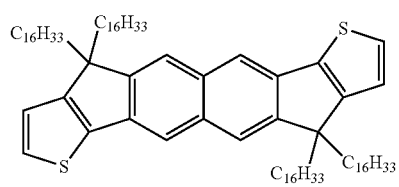

A 250 mL flask was charged with LiAlH$_4$ (78.55 mg, 2.07 mmol), hexadecyl bromide (632 mg, 2.07 mmol), and 60 mL of dry THF. The solution was stirred and cooled down in an ice/water bath to approx. 15° C. before a solution of 4,10 bis(hexadecylidene)-4,10-dihydro-naphtho[3",2":3,4;7",6":3',4'] dicyclopenta[2,1-b:2',1'-b] dithiophene (788 mg, 1.04 mmol) in 60 mL of dry THF was added slowly via a syringe. More LiAlH$_4$ (30 mg) and hexadecyl bromide (200 µl) were added until the starting material was entirely consumed, then left to stir at RT for another hour. Then the reaction mixture was quenched by carefully adding H$_2$O and the THF was distilled off. The residue was extracted with ethyl acetate and the combined organic layers dried over MgSO4. The crude was purified by column chromatography (using hexanes as eluent) followed by recrystallization from hexanes. Yield: 194 mg (15%).

$^1$H NMR (400 MHz, CDCl$_3$, δ): 7.76 (s, 2H), 7.64 (s, 2H), 7.33 (d, 2H), 6.99 (d, 2H), 1.95 (m, 8H) 1.3-1.15 (m, 112 H) 0.87 (t, 12H)

MALDI-TOF-MS: C$_{84}$H$_{140}$S$_2$ [C$_{84}$H$_{141}$S$_2$+=MH+] calc'd 1214.1 found: 1214.2

Example 11

2,8-Dibromo-4,4,10,10-tetrakis-(hexadecyl)-4,10-dihydro-naphtho[3",2":3,4;7",6":3',4']-dicyclopenta[2,1-b:2',1'-b']-dithiophene

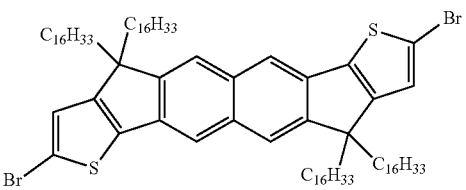

A solution of 4,4,10,10-tetrakis-(hexadecyl)-4,10-dihydro-naphtho[3",2":3,4;7",6":3',4'] dicyclopenta[2,1-b:2',1'-b']-dithiophene (104 mg, 0.086 mmol) in chloroform (20 ml) was cooled to 0° C. under argon in the absence of light. N-bromosuccinimide (33.6 mg, 0.189 mmol) dissolved in chloroform (5 ml) was added in portions and the reaction progress was monitored by TLC. After full conversion had been detected, the reaction mixture was extracted with water, dried over magnesium sulphate and evaporated to dryness. The crude was purified by column chromatography (using hexanes as mobile phase) Yield: 107 mg of a white solid (90%).

$^1$H NMR (400 MHz, CDCl$_3$, δ): 7.69 (s, 2H), 7.62 (s, 2H), 7.00 (s, 2H), 1.92 (m, 8 H), 1.30-1.05 (m, 112 H), 0.87 (t, 12 H)

$^{13}$C-NMR (100 MHz, CDCl$_3$, δ): 155.35, 150.93, 141.57, 131.98, 125.03, 121.27, 116.66, 114.38, 54.64, 40.00, 32.15, 30.27, 29.90, 29.85, 29.59, 24.47, 22.92, 14.34

MALDI-TOF-MS: C$_{84}$H$_{138}$Br$_2$S$_2$ [C$_{84}$H$_{139}$Br$_2$S$_2$+=MH+] calc'd 1371.9, found 1372.0

Example 12

P1 (polymer)

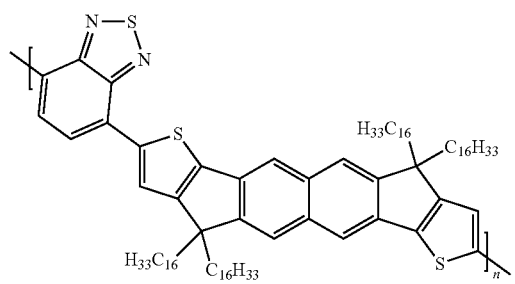

P1

2,8-Dibromo-4,4,10,10-tetrakis(hexadecyl)-4,10-dihydro-naphtho[3",2":3,4;7",6":3',4'] dicyclopenta[2,1-b:2',1'-b']-dithiophene (85.63 mg, 0.06241 mmol) and 4,7-bis(4,4,5,5-tetramethyl-1,3,2-dioxaborolan-2-Abenzo[c][1,2,5]thiadiazole (24.23 mg, 0.06243 mmol) were placed in a 20 mL microwave vial. $Pd_2(dba)_3$ (3.01 mg, $3.3 \times 10^{-3}$ mmol), (o-tol)$_3$P (4.03 mg, 0.0132 mmol), Aliquat 336 (1 drop) and toluene (5 ml) were added. This solution was degassed with argon for 30 min. Then, degassed $Na_2CO_3$ solution (1M) was added and the resulting mixture was degassed for another 10 minutes. Then, the vial was sealed and heated at 120° C. for 48 h.

To end-cap the polymer chains, a few drops of bromobenzene were added (approx. 100 μl) via a syringe and the reaction mixture was continued to reflux for 2 h. Then, phenylboronic acid (100 mg) was added and the reaction mixture was refluxed overnight. The resulting blue solution was precipitated into methanol and the precipitated polymer was recovered by filtration directly into an extraction thimble. Soxleth extractions were performed with acetone, hexanes and chloroform. The majority of the polymer was dissolved in the hexanes fraction. Therefore, the hexanes and chloroform fractions were combined and redissolved in chloroform. This solution was treated with diethylammonium dithiocarbamate to remove palladium salts after which the organic phase was extracted with water three times, dried over magnesium sulphate and concentrated to about 2 ml. This concentrated solution was precipitated into methanol and this precipitation was repeated twice.

67 mg (79%) of a deep blue metallic solid of formula P1 with purple reflection were obtained. GPC (chlorobenzene, 80° C.): Mn=15000, Mw=26000, PDI=1.7

$^1$H NMR (400 MHz, CDCl$_3$, δ): 8.2 (br s, 2H), 8.0 (br s, 1H), 7.9 (br s, 1 H), 7.8 (br s, 2H), 2.2 -2.0 (br m, 8H), 1.3-1.1 (br m, 112H). 0.89 (t, 12H)

TABLE 1

| | Comonomer | Polymer (Yield) | $\lambda_{max}$ (film) | Eg opt | HOMO/LUMO |
|---|---|---|---|---|---|
| I-NDT | BT | P1 | 639 | 1.81 | −5.4/−3.6[a] |

Example 13

P2 (polymer)

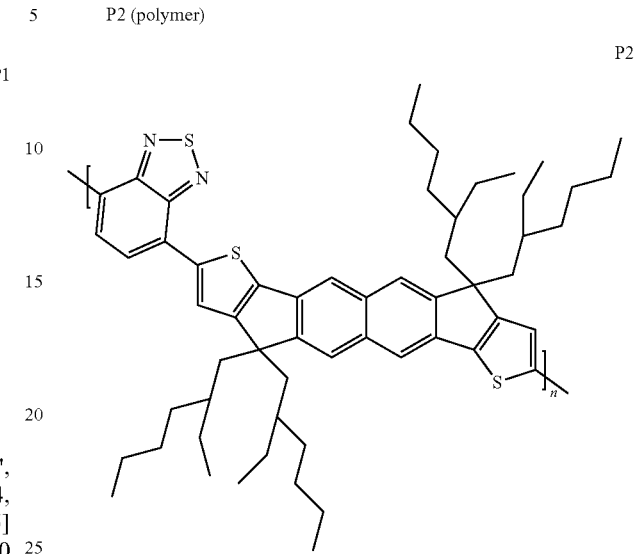

P2

The polymer P2 Has Been Synthesized in Analogy to Polymer P1

Preparation of Back-Contact, Top-Gate FETs

Semiconducting compound or polymer is dissolved at a concentration of 0.75 wt % in orthodichlorobenzene and subsequently coated onto a PET-substrate with lithographically prepatterned gold contacts, serving as Source and Drain contact of the FET.

The formulation is applied by spin coating (1200 rpm, 30 seconds). After the coating is completed, the substrate is immediately transferred onto a preheated hotplate and heated for 60 s at 90° C. Next the gate dielectric layer consisting of 4 wt % PS dissolved in propylene glycol monomethyl ether acetate (PGMEA) is spincoated on top of the organic semiconductor (2500 rpm, 30 seconds). After Spincoating, the substrate is again transferred to the hotplate and annealed for another 5 Min at 90° C. The thickness of the dielectric layer is 450 nm measured by profilometer. Finally 50 nm thick shadow-mask patterend gold gate electrodes are deposited by vacuum evaporation to complete FETs in the BCTG configuration.

Electrical Characterization

The mobility μ is calculated from the root representation of the transfer characteristic curve (solid grey curve) calculated in the saturation region. The slope m is determined from the dashed black line in FIG. 1. The dashed black line in FIG. 1 is fitted to a region of the root representation of the current characteristic ID such that a good correlation to the linear slope of the root representation is obtained.

The threshold voltage Um can be taken from the intersection of black dashed line in FIG. 1 with the X-axis portion ($V_{GS}$).

In order to calculate the electrical properties of the OFET, the following equations are employed:

$$\mu = \frac{m^2 * 2L}{C_G * W} \quad C_G = \varepsilon_0 * \varepsilon_r \frac{1}{d} \quad U_{th} = -1 * \frac{m}{b}$$

-continued $$ON/OFF = \frac{I_D max}{I_D min}$$

where $\varepsilon_0$ is the vacuum permittivity of $8.85 \times 10^{-12}$ As/Vm. $!_r=2{,}6$ for Cytop and d=450 nm is the thickness of the dielectric. The W/L ratio is 25.

TABLE 2

The following mobilities have been calculated for the respective compounds:

| Compound | Field-effect mobility μ [cm²/Vs] | Threshold voltage $U_{TH}$ [V] | ON/OFF ratio |
|---|---|---|---|
| P1 | 0.3 | −8 | 5E5 |
| P2 | 0.006 | −4.5 | 2E4 |

Figure 1:
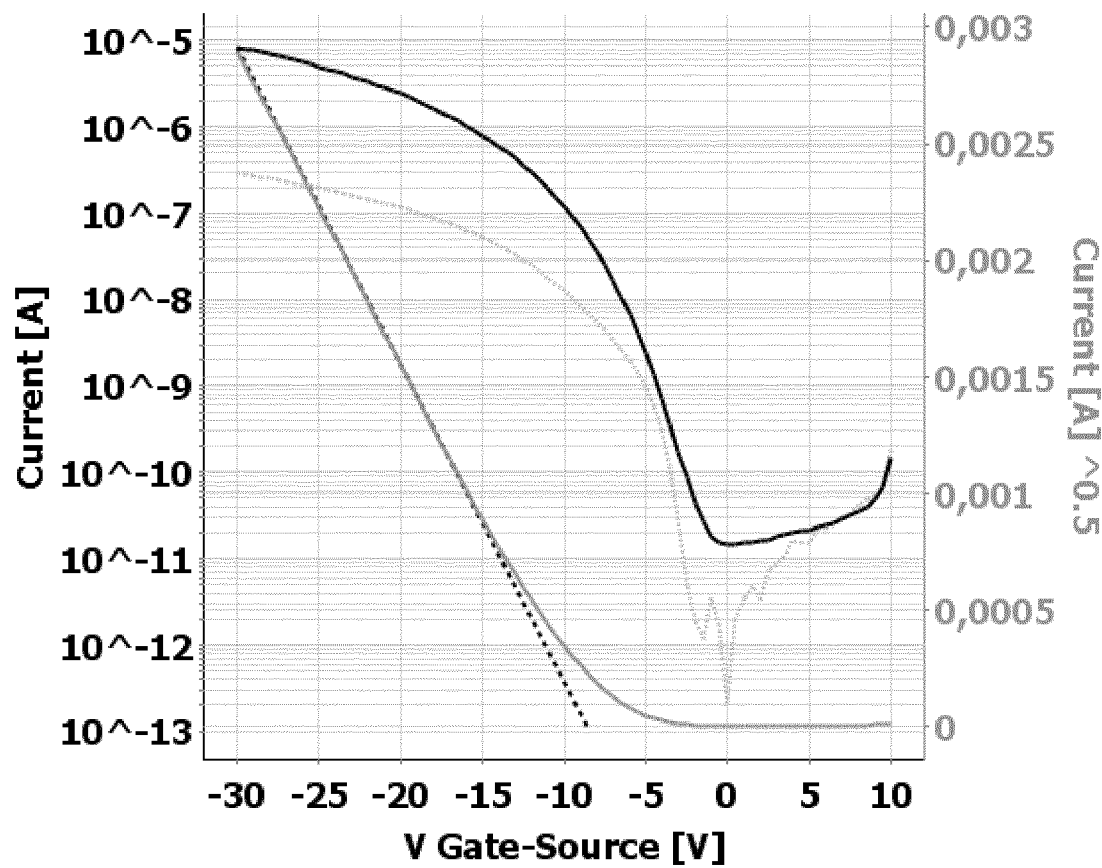
FIG. 1 shows a representative transfer characteristics of a FET fabricated from polymer P1 with VGS=10 V to −30 V at 0.5V step size with VDS=−30V:Drain current (black solid curve), gate current (dotted grey curve), square root of drain current (grey solid curve), and fitted slope of square root (dashed black curve).
Figure 2:
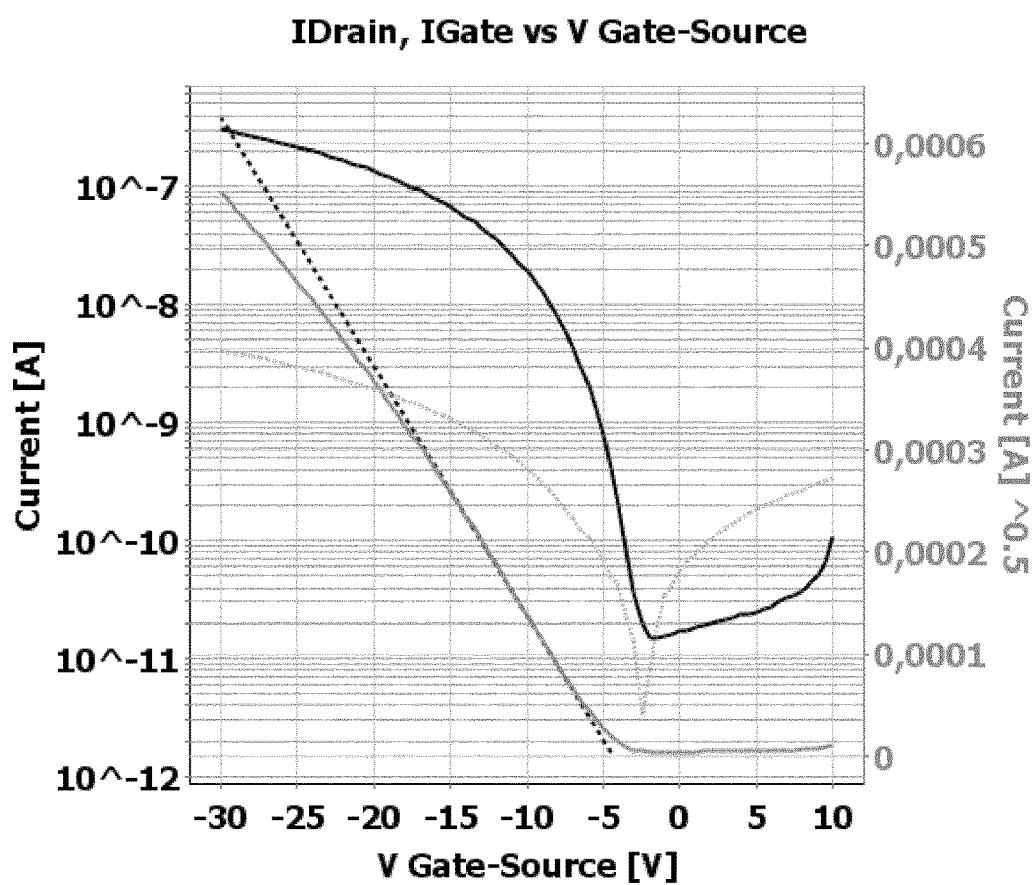
FIG. 2 shows a representative transfer characteristics of a FET fabricated from Polymer P2 with $V_{GS}$=10 V to −30 V at 0.5V step size with $V_{DS}$=−30V:Drain current (black solid curve), gate current (dotted grey curve), square root of drain current (grey solid curve), and fitted slope of square root (dashed black curve).

The invention claimed is:
1. A polymer comprising a unit of formula 1:

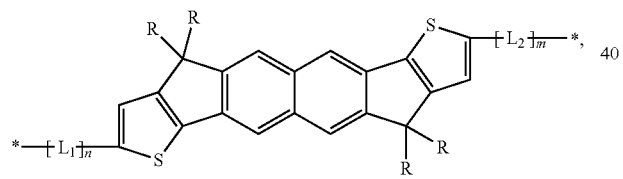

1 wherein:
n is 0, 1, 2, 3, or 4;
m is 0, 1, 2, 3, or 4;
R is selected from the group consisting of hydrogen, $C_{1-30}$-alkyl, and phenyl;
$L^1$ and $L^2$ are each independently selected from the group consisting of $C_{6-30}$-arylene, 5 to 30 membered heteroarylene,

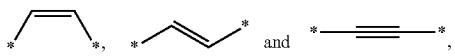

wherein $C_{6-30}$-arylene and 5 to 30 membered heteroarylene are optionally substituted with one to six substituents $R^3$ selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)$—$R^{31}$, $C(O)$—$OR^{31}$, $C(O)$—$R^{31}R^{32}$, $NR^{31}$—$C(O)R^{32}$,$C(O)$—$NR^{31}R^{32}$, $N[C(O)R^{31}][C(O)R^{32}]$, SR$^{31}$, halogen, CN, $SiR^{Siv}R^{Siw}R^{Six}$ and OH, wherein

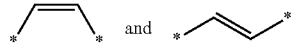

are optionally substituted with one or two substituents $R^4$ selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)$—$R^{41}$, $C(O)$—$NR^{41}R^{42}$, $C(O)$—$OR^{41}$ and CN, wherein, in $R^{31}$, $R^{32}$, $R^{41}$, and $R^{42}$, are each independently selected from the group consisting of H, $C_{1-30}$-alkynyl, $C_{2-30}$-alkenyl, $C_{2-36}$-alkynyl, $C_{5-12}$, -cycloalkyl, $C_{6-18}$-aryl and 5 and 20 membered heroaryl, wherein, in $R^{31}$, $R^{32}$, $R^{41}$, are each independently selected from the group consisting of H, $C_{1-30}$-alkyl, $C_{2-30}$-alkenyl and $C_{2-30}$-alkynyl $C_{5-12}$- cycloalkyl, $C_{6-18}$-aryl and 5 to 20 membered heteroaryl, wherein, in $R^{31}$, $R^{32}$, $R^{41}$, and $R^{42}$, $C_{5-12}$-cycloalkyl is optionally substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, $SiR^{Siv}R^{Siw}R^{Six}$ and NO$_2$: and one or two CH$_2$-groups, but not adjacent CH$_2$-groups, of $C_{5-12}$-cycloalkyl are optionally replaced by O, S, OC(O), CO, NR$^i$ or NR$^i$—CO, wherein, in $R^{31}$, $R^{32}$, $R^{41}$, and $R^{42}$, $C_{6-18}$-aryl and 5 to 20 membered heteroaryl are optionally substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, $SiR^{Siv}R^{Siw}R^{Six}$ and NO$_2$, wherein, in $R^{31}$, $R^{32}$, $R^{41}$, and $R^{42}$, $C_{1-30}$-alkyl, $C_{2-30}$-alkenyl and $C_{2-30}$-alkynyl are optionally substituted with one to ten substituents independently selected from the group consisting of $C_{5-8}$-cycloalkyl, $C_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, $SiR^{Siv}R^{Siw}R^{Six}$ and NO$_2$; and at least two CH$_2$-groups, but not adjacent CH$_2$-groups of $C_{1-30}$-alkyl, $C_{2-30}$-alkenyl and $C_{2-30}$-alkynyl are optionally replaced by O or S, wherein, in $R^{31}$, $R^{32}$, $R^{41}$, and $R^{42}$, $C_{5-12}$-cycloalkyl is optionally substituted with one to six substituents independently selected from the group consisting of $C_{1-20}$-alkyl, and $C_{2-20}$-alkeynyl and $C_{2-20}$-alkynyl, $C_{5-8}$-cycloalkyl, $C_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$C(O)R$^i$], SR$^i$, halogen, CN, $SiR^{Siv}R^{Siw}R^{Six}$ and NO$_2$: and one or two CH$_2$-groups, but not adjacent CH$_2$-groups, of $C_{5-12}$-cycloalkyl are optionally replaced by O, S, OC(O), CO, NR$^i$ or NR$^i$—CO, wherein, in $R^{31}$, $R^{32}$, $R^{41}$, and $R^{42}$, $C_{6-18}$-aryl and 5 to 20 membered heteroaryl are optionally substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, $SiR^{Siv}R^{Siw}R^{Six}$ and NO$_2$, wherein $R^{Siv}$, $R^{Siw}$, and $R^{Six}$ are each independently selected from the group consisting of H, $C_{1-20}$-alkyl, $C_{2-20}$-alkenyl, $C_{2-20}$-alkynyl, $C_{5-6}$-cycloalkyl, phenyl and $O-Si(CH_3)_3$, wherein $R^i$, $R^j$ are each independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, wherein, in $R^{Siv}$, $R^{Siw}$, $R^{Six}$, $R^i$, $R^j$, $C_{1-20}$-alkyl, $C_{2-20}$-alkenyl and $C_{20}$-alkynyl are optionally substituted with one to five substituents selected from the group consisting of $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^1$, $NR^k-C(O)R^1$, $C(O)-NR^kR^l$, $N[C(O)R^k][C(O)R^1]$, $SR^k$, halogen, CN, and $NO_2$, wherein, in $R^{Siv}$, $R^{Siw}$, $R^{Six}$, $R^i$, and $R^j$, $C_{5-8}$-cycloalkyl is optionally substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^1$, $NR^k-C(O)R^1$, $C(O)-NR^kR^1$, $N[C(O)R^k][C(O)R^1]$, $SR^k$, halogen, CN, and $NO_2$.

wherein, in $R^{Siv}$, $R^{Siw}$, $R^{Six}$, $R^i$, and $R^j$, $C_{6-14}$-aryl and 5 to 14 membered heteroaryl are optionally substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^1$, $NR^k-C(O)R^1$, $C(O)-NR^kR^1$, $N[C(O)R^k][C(O)R^l]$, $SR^k$, halogen, CN, and $NO_2$, wherein $R^k$ and $R^l$, are independently selected from the group consisting of H, $C_{1-10}$-alkyl, $C_{2-10}$-alkenyl and $C_{2-10}$-alkynyl, and wherein, in $R^k$ and $R^l$, $C_{1-10}$-alkyl, $C_{2-10}$-alkenyl and $C_{2-10}$-alkynyl are optionally substituted with one to five substituents selected from the group consisting of halogen, CN and $NO_2$.

2. The polymer of claim 1, wherein $L^1$ and $L^2$ are each independently selected from the group consisting of $C_{6-30}$-arylene and 5 to 30 membered heteroarylene, and

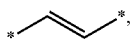

wherein $C_{6-30}$-arylene and 5 to 30 membered heteroarylene are optionally substituted with one to six substituents $R^3$ selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)-R^{31}$, $C(O)-OR^{31}$, $C(O)-R^{31}$, $NR^{31}R^{32}$, $NR^{31}-C(O)R^{32}$, $C(O)-NR^{31}R^{32}$, $SR^{31}$, halogen, CN, $SiR^{Siv}R^{Siw}R^{Six}$ and OH, and wherein

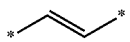

is optionally substituted with one or two substituents $R^4$ selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)-R^{41}$, $C(O)-NR^{41}R^{42}$, $C(O)-OR^{41}$ and CN, wherein $R^{31}$, $R^{32}$, $R^{41}$ and $R^{42}$ are each independently selected from the group consisting of H, $C_{1-30}$alkyl, $C_{2-30}$-alkenyl, $C_{2-30}$-alkynyl, $C_{5-12}$-cycloalkyl, $C_{6-18}$-aryl and 5 to 20 membered heteroaryl, wherein, $R^{31}$, $R^{32}$, $R^{41}$, and $R^{42}$, $C_{1-30}$-alkyl, $C_{2-30}$-alkenyl and $C_{2-30}$-alkynyl are optionally substituted with one to ten substituents independently selected from the group consisting of $C_{5-8}$-cycloalkyl, $C_{6-14}$-aryl, 5 to 14 membered heteroaryl, $OR^i$, $OC(O)R^j$, $C(O)$- $OR^i$, $C(O)-R^i$, $NR^iR^j$, $NR^i-C(O)R^j$, $C(O)-NR^iR^j$, $N[C(O)R^i][C(O)R^j]$, $SR^i$, halogen, CN, $SiR^{Siv}R^{Siw}R^{Six}$ and $NO_2$; and at least two $CH_2$-groups, but not adjacent $CH_2$-groups of $C_{1-30}$- alkyl, $C_{2-30}$-alkenyl and $C_{2-30}$-alkynyl are optionally replaced by O or S, wherein, $R^{31}$, $R^{32}$, $R^{41}$, and $R^{42}$, $C_{5-12}$-cycloalkyl is optionally substituted with one to six substituents independently selected from the group consisting of $C_{1-20}$-alkyl, $C_{2-20}$-alkenyl and $C_{2-20}$alkynyl, $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR-C(O)R^k$, $C(O)-NR^iR^j$, $N[C(O)R^i][C(O)R^j]$, $SR^i$, halogen, CN, $SiR^{Siv}R^{Siw}R^{Six}$ and $NO_2$; and one or two $CH_2$-groups, but not adjacent $CH_2$-groups, of $C_{5-12}$-cycloalkyl are optionally replaced by O, S, OC(O), CO, $NR^i$or $NR^i$—CO, wherein, $R^{31}$, $R^{32}$, $R^{41}$, and $R^{42}$, $C_{6-18}$-aryl and 5 to 20 membered heteroaryl are optionally substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^j$, $C(O)-NR^iR^j$, $N[C(O)R^i][C(O)R^j]$, $SR^i$, halogen, CN, $SiR^{Siv}R^{Siw}R^{Six}$ and $NO_2$, wherein $SiR^{Siv}R^{Siw}R^{Six}$ are each independently selected from the group consisting of H, $C_{1-20}$-alkyl, $C_{2-20}$-alkenyl, $C_{2-20}$-alkynyl, $C_{5-6}$-cycloalkyl, phenyl and $O-Si(CH_3)_3$, and wherein $R^i$ and $R^j$ are independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, wherein, in $R^i$ and $R^j$, $C_{1-20}$-alkyl, $C_{2-20}$-alkenyl and $C^{2-20}$-alkynyl are optionally substituted with one to five substituents selected from the group consisting of $C_{5-6}$-cycloalkyl, $C_{6-10}$-aryl, 5 to 10 membered heteroaryl, $OR^k$, $OC(O)-R^l$, $C(O)-OR^k$, $C(O)-R^k$, $NR^kR^1$, $NR^k-C(O)R^1$, $C(O)-NR^kR^1$, $N[C(O)R^k][C(O)R^1]$, $SR^k$, halogen, CN, and $NO_2$, wherein, in $R^i$ and $R^j$ , $C_{5-8}$-cycloalkyl is optionally substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^1$, $NR^k-C(O)R^1$, $C(O)-NR^kR^1$, $N[C(O)R^k][C(O)R^l]$, $SR^k$, halogen, CN, and $NO_2$, wherein, in $R^i$ and $R^j$, $C_{6-14}$-aryl and 5 to 14 membered heteroaryl are optionally substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^1$, $NR^k-C(O)R^1$, $C(O)-NR^kR^1$, $N[C(O)R^k][C(O)R^1]$, $SR^k$, halogen, CN, and $NO_2$, wherein $R^k$ and $R^l$ are independently selected from the group consisting of H, $C_{1-10}$alkyl, $C_{2-10}$-alkenyl and $C_{2-10}$-alkynyl, and wherein, in $R^k$ and $R^1$, $C_{2-10}$-alkenyl and $C_{2-10}$-alkynyl are optionally substituted with one to five substituents selected from the group consisting of halogen, CN and NO$_2$.

3. The polymer of claim 2, wherein $L^1$ and $L^2$ are each independently selected from the group consisting of $C_{6-30}$-arylene and 5 to 30 membered heteroarylene, and

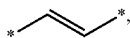

wherein $C_{6-30}$-arylene and 5 to 30 membered heteroarylene is selected from the group consisting of

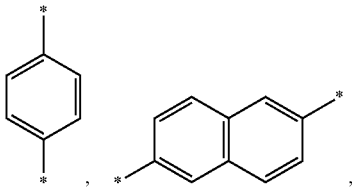

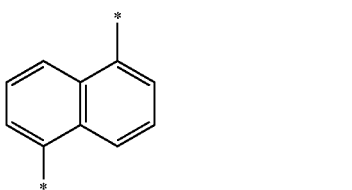

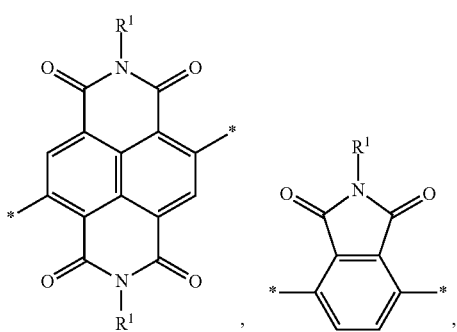

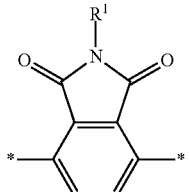

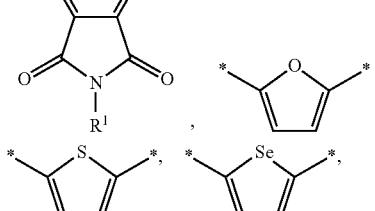

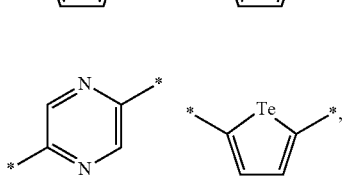

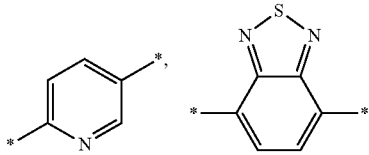

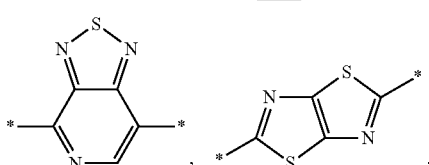

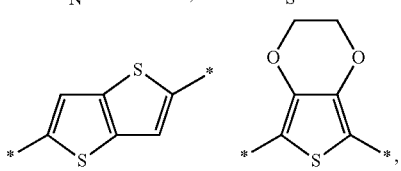

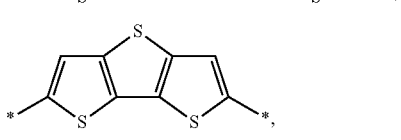

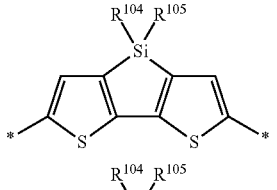

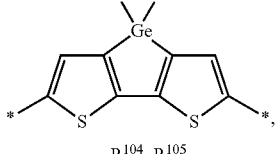

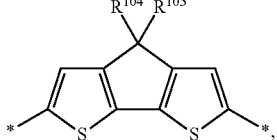

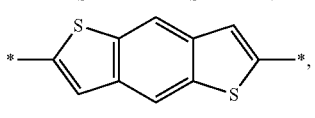

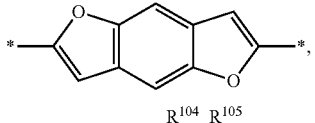

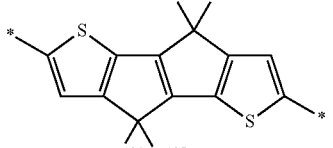

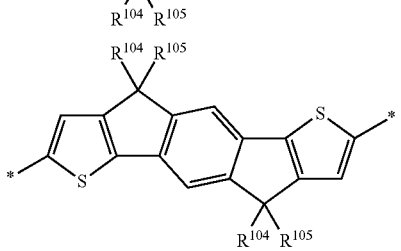 and

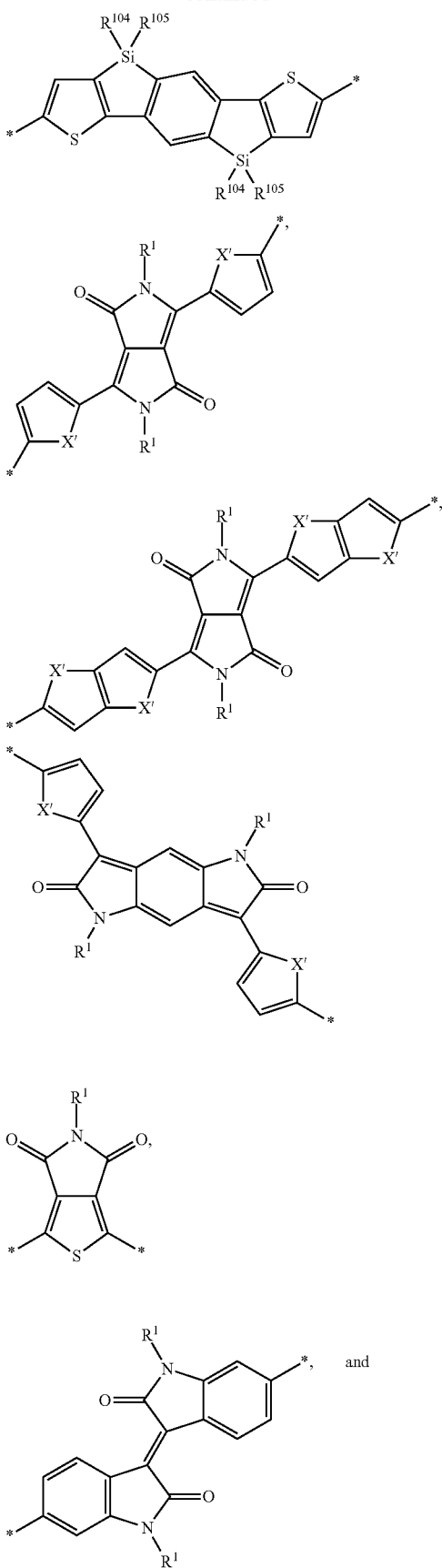

wherein $R^1$ is selected from the group consisting of $C_{1-36}$-alkyl, $C_{3-36}$-alkenyl and $C_{3-36}$alkynyl, wherein $C_{1-36}$-alkyl, $C_{3-36}$-alkenyl and $C_{3-36}$-alkynyl are optionally substituted with one to twenty substituents independently selected from the group consisting of $C_{5-6}$-cycloalkyl, $C_{6-10}$-aryl, 5 to 10 membered heteroaryl, $OR^a$, $SR^a$, $Si(R^{sia})(R^{Sib})(R^{Sic})$, —O—Si$(R_{Sia})(R^{Sib})(R^{Sic})$, halogen, and CN; and at least two $CH_2$-groups, but not adjacent $CH_2$-groups, of $C_{1-36}$-alkyl, $C_{2-36}$-alkenyl and $C_{2-36}$-alkynyl are optionally replaced by O or S, wherein $R^a$ is independently selected from the group consisting of H, $C_{3-20}$-alkenyl, $C_{3-20}$-alkynyl, $C_{5-6}$-cycloalkyl and $C_{6-10}$aryl, wherein $R^{Sia}$, $R^{Sib}$ and $R^{Sic}$ are independently selected from the group consisting of H, $C_{1-26}$-alkyl, $C_{2-20}$-alkenyl, $C_{2-20}$-alkynyl, $C_{5-6}$-cycloalkyl, $C_{6-10}$-aryl, —[O—SiR$^{Sid}$R$^{Sie}$]$_o$—R$^{Sif}$ wherein o is an integer from 1 to 50, wherein $R^{Sid}$, $R^{Sie}$, $R^{Sif}$ are independentl selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, -[O—SiR$^{Sig}$R$^{Sih}$]$_p$—R$^{Sii}$, wherein p is an integer from 1 to 50, wherein $R^{Sig}$ $R^{Sih}$, $R^{Sii}$ are indeendently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, O—Si$(CH_3)_3$, $C_{1-20}$-alkyl, $C_{2-20}$-alkenyl and $C_{2-20}$-alkynyl are optionally substituted with one to ten substituents selected from the group consisting of halogen and CN, wherein $R^{104}$ and $R^{105}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{104}$ and $R^{105}$, if attached to the same atom, together with the atom, to which they are attached, form a 5 to 12 membered ring system, wherein, in $R^{104}$ and $R^{105}$, $C_{1-20}$-alkyl, $C_{2-20}$-alkenyl and $C_{2-20}$-alkynyl are optionally substituted with one to five substituents selected from the group consisting of $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^1$, $C(O)$—$NR^sR^t$, $N[C(O)R^s][C(O)R^t]$, $SR^s$, halogen, CN, and $NO_2$, wherein, in $R^{104}$ and $R^{105}$, $C_{5-8}$-cycloalkyl is optionally substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, wherein, in $R^{104}$ and $R^{105}$, $C_{6-14}$-aryl and 5 to 14 membered heteroaryl are optionally substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, wherein, in $R^{104}$ and $R^{105}$, 5 to 12 membered ring system is optionally substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^3$, $OC(O)$—$R^t$, $C(O)$—$OR^s$, $C(O)$-$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, wherein $R^s$ and $R^t$ are independently selected from the group consisting of H, $C_{1-10}$-alkyl, $C_{2-10}$-alkenyl and $C_{2-10}$-alkynyl, wherein, in $R^s$ and $R^t$, $C_{1-10}$-alkyl, $C_{2-10}$-alkenyl and $C_{2-10}$-alkynyl are optionally substituted with one to five substituents selected from the group consisting of halogen, CN and $NO_2$, wherein $C_{6-30}$-arylene and 5 to 30 membered heteroarylene are optionally substituted with one to six substituents $R^3$ at each occurrence selected from the group consisting of $C_{1-30}$-alkyl and halogen, wherein

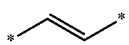

is optionally substituted with one or two substituents $R^4$ selected from the group consisting of $C_{1-30}$-alkyl, $C(O)$—$R^{41}$, $C(O)$—$OR^{41}$ and CN, and wherein $R^{41}$ is at each occurrence $C_{1-30}$-alkyl.

4. The polymer of claim 3, wherein $L^1$ and $L^2$ are each independently selected from a group consisting of

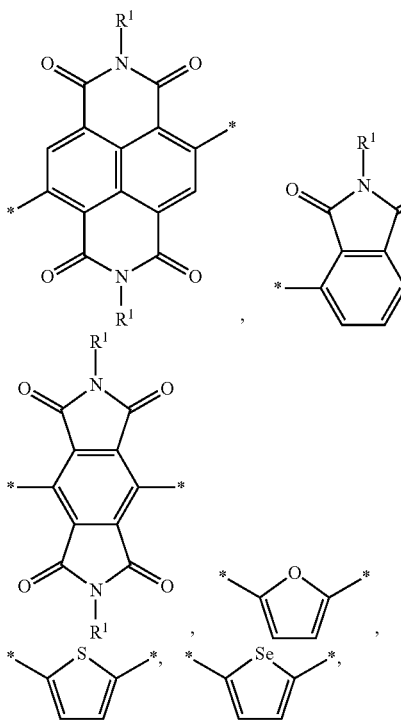

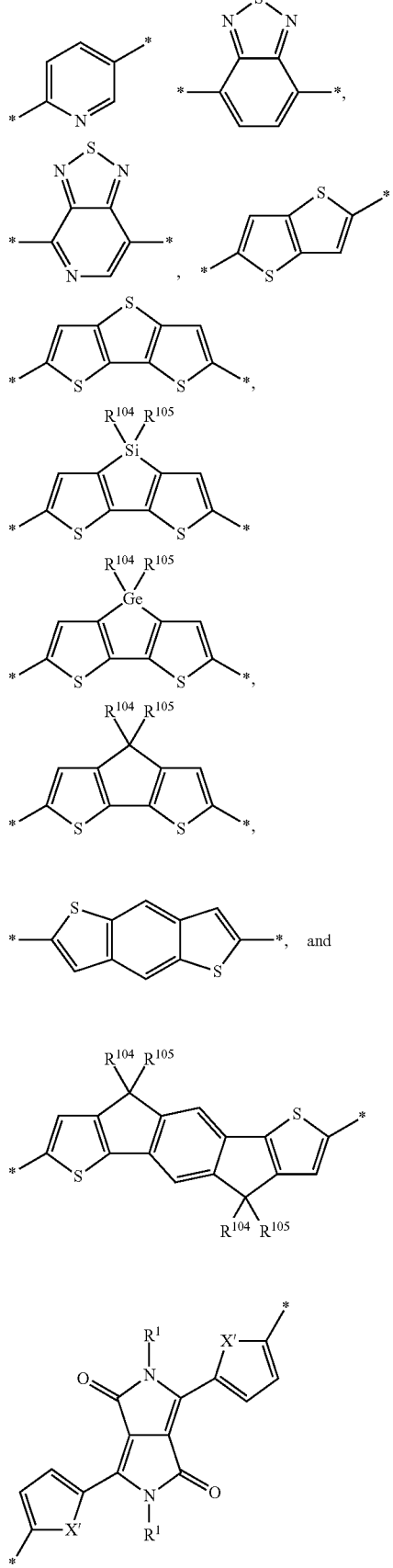

-continued

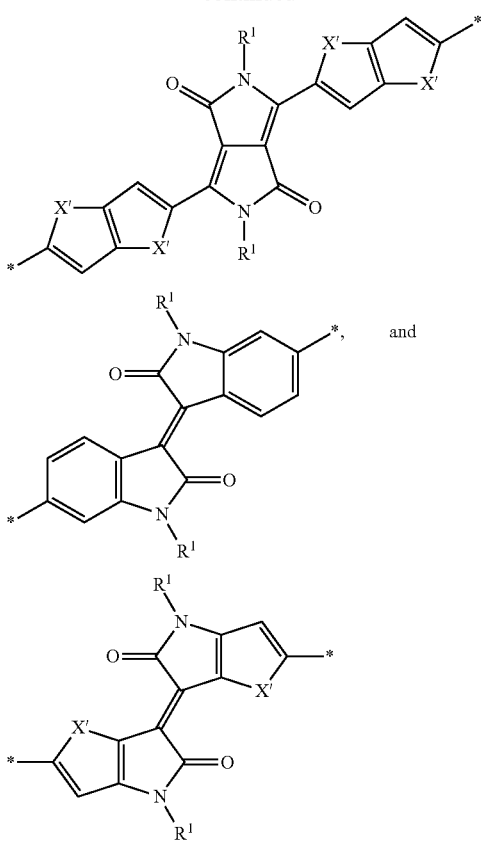

and wherein L¹ and L² are not further substituted.

5. The polymer of claim 1, wherein L¹ and L² are selected from

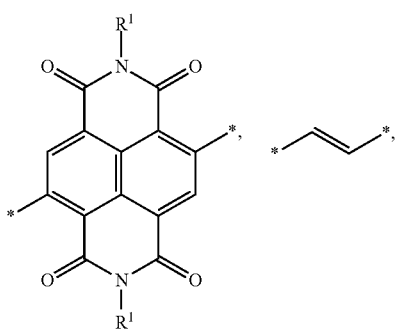

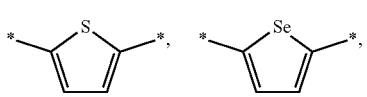

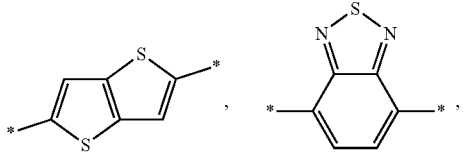

-continued

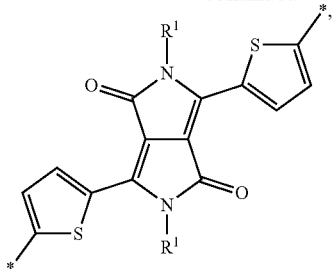

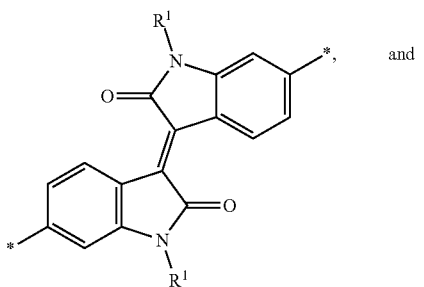

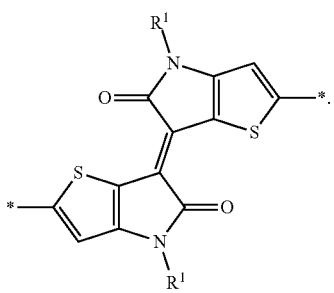

6. The polymer of claim 1, wherein:
n is 0, 1, or 2; and
m is 0, 1, or 2.

7. An electronic device, comprising the polymer of claim 1.

8. The electronic device of claim 7, wherein the electronic device is an organic field effect transistor.

9. The polymer of claim 1, comprising at least 2 units of the formula 1 and having a $M_n$ of up to 15000 and/or $M_w$ of up to 26000.

10. The polymer of claim 1, wherein the polymer has a PDI up to 1.7.

11. A polymer comprising a unit of formula 1

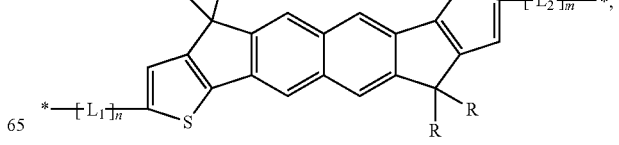

or
a compound of formula 1':

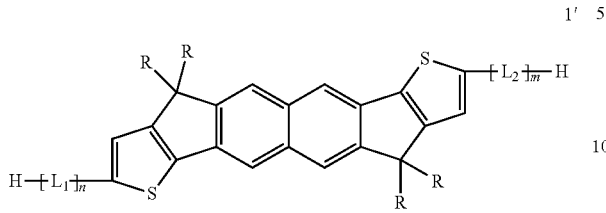

wherein
n is 1, 2, 3, or 4,
m is 0, 1, 2, 3, or 4,
R is hydrogen, $C_{1-30}$-alkyl, and phenyl;
wherein $L_1$ comprises

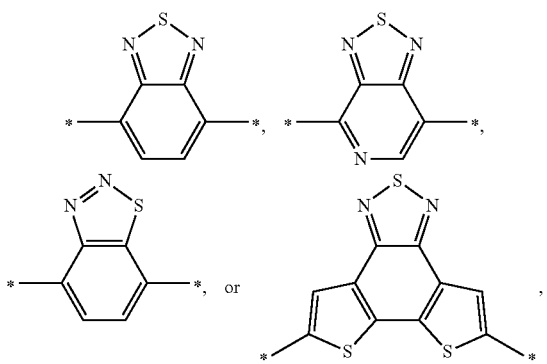

wherein $L_2$, is selected from the group consisting of $C_{6-30}$-arylene, 5 to 30 membered heteroarylene,

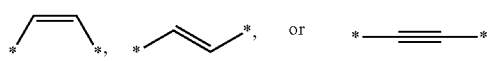

wherein $C_{6-30}$-arylene and 5 to 30 membered heteroarylene are optionally substituted with one to six substituents $R^3$ selected from the group consisting of $C_{1-30}$-alkyl, $C_{2-30}$-alkenyl, $C_{2-30}$-alkynyl, $C_{5-12}$-cycloalkyl, $C_{6-18}$-aryl, 5 to 20 membered heteroaryl, $OR^{31}$, $OC(O)—R^{31}$, $C(O)—OR^{31}$, $C(O)—R^{31}$, $NR^{31}R^{32}$, $NR^{31}—C(O)R^{32}$, $C(O)—NR^{31}R^{32}$, $N[C(O)R^{31}][C(O)R^{32}]$, $SR^{31}$, halogen, CN, $SiR^{Siv}R^{Siw}R^{Six}$, and OH,
wherein

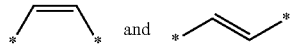

are optionally substituted with one or two substituents $R^4$ selected from the group consisting of $C_{1-30}$-alkyl, $C_{2-30}$-alkenyl, $C_{2-30}$-alkynyl, $C_{5-12}$-cycloalkyl, $C_{6-18}$-aryl, 5 to 20 membered heteroaryl, $C(O)—R^{41}$, $C(O)—NR^{41}R^{42}$, $C(O)—OR^{41}$, and CN,
wherein $R^{31}$, $R^{32}$, $R^{41}$, and $R^{42}$ are each independently selected from the group consisting of H, $C_{1-30}$-alkyl, $C_{2-30}$-alkenyl, $C_{2-30}$-alkynyl, $C_{5-12}$-cycloalkyl, $C_{6-18}$-aryl, and 5 to 20 membered heteroaryl, wherein, in $R^{31}$, $R^{32}$, $R^{41}$, and $R^{42}$, $C_{1-30}$-alkyl, $C_{2-30}$-alkenyl and $C_{2-30}$-alkynyl are optionally substituted with one to ten substituents independently selected from the group consisting of $C_{5-8}$-cycloalkyl, $C_{6-14}$-aryl, 5 to 14 membered heteroaryl, $OR^i$, $OC(O)—R^j$, $C(O)—OR^j C(O)—R^i$, $NR^iR^j$, $NR^i—C(O)R^j$, $C(O)—NR^iR^j$, $N[C(O)R^i][C(O)R^j]$, $SR^i$, halogen, CN, $SiR^{Siv}R^{Siw}R^{Six}$, and $NO_2$; and at least two $CH_2$-groups, but not adjacent $CH_2$-groups of $C_{1-30}$-alkyl, $C_{2-30}$-alkenyl and $C_{2-30}$-alkynyl are optionally replaced by O or S, wherein, in $R^{31}$, $R^{32}$, $R^{41}$, and $R^{42}$, $C_{5-12}$-cycloalkyl is optionally substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, $OC(O)—R^j$, $C(O)—OR^i$, $C(O)—R^i$, $NR^iR^j$, $NR^i—C(O)R^j$, $C(O)—NR^iR^j$, $N[C(O)R^i][C(O)R^j]$, $SR^i$, halogen, CN, $SiR^{Siv}R^{Siw}R^{Six}$, and $NO_2$; and one or two $CH_2$-groups, but not adjacent $CH_2$-groups, of $C_{5-12}$-cycloalkyl are optionally replaced by O, S, OC(O), CO, $NR^i$, or $NR^i—CO$, wherein, in $R^{31}$, $R^{32}$, $R^{41}$, and $R^{42}$, $C_{6-18}$-aryl and 5 to 20 membered heteroaryl are optionally substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, $OC(O)—R^j$, $C(O)—OR^i$, $C(O)—R^i$, $NR^iR^j$, $NR^i—C(O)R^j$, $C(O)—NR^iR^j$, $N[C(O)R^j][C(O)R^j]$, $SR^i$, halogen, CN, $SiR^{Siv}R^{Siw}R^{Six}$, and $NO_2$, wherein $R^{Siv}$, $R^{Siw}$, $R^{Six}$ are each independently selected from the group consisting of H, $C_{1-20}$-alkyl, $C_{2-20}$-alkenyl, $C_{2-20}$-alkynyl, $C_{5-6}$-cycloalkyl, phenyl and $O-Si(CH_3)_3$, wherein $R^i$ and $R^j$ are independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, wherein, in $R^{Siv}$, $R^{Siw}$, $R^{Six}$, $R^i$, $R^j$, $C_{1-20}$-alkyl, $C^{2-20}$-alkenyl, and $C_{2-20}$-alkynyl are optionally substituted with one to five substituents selected from the group consisting of $C_{5-6}$-cycloalkyl, $C_{6-10}$-aryl, 5 to 10 membered heteroaryl, $OR^k$, $OC(O)—R^1$, $C(O)—OR^k$, $C(O)—R^k$, $NR^kR^1$, $NR^k—C(O)R^1$, $C(O)—NR^kR^1$, $N[C(O)R^k][C(O)R^1]$, $SR^k$, halogen, CN, and $NO_2$, wherein, in $R^{Siv}$, $R^{Siw}$, $R^{Six}$, $R^i$, and $R^j$, $C_{5-8}$-cycloalkyl is optionally substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)—R^1$, $C(O)—OR^k$, $C(O)—R^k$, $NR^kR^1$, $NR^k—C(O)R^1$, $C(O)—NR^kR^1$, $N[C(O)R^k][C(O)R^1]$, $SR^k$, halogen, CN, and $NO_2$, wherein, in $R^{Siv}$, $R^{Siw}$, $R^{Six}$, $R^i$, $R^j$, $C_{6-14}$-aryl and 5 to 14 membered heteroaryl are optionally substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)—R^1$, $C(O)—OR^k$, $C(O)—R^k$, $NR^kR^1$, $NR^k—C(O)R^1$, $C(O)—NR^kR^1$, $N[C(O)R^k][C(O)R^1]$, $SR^k$, halogen, CN, and $NO_2$, wherein $R^k$ and $R^1$ are independently selected from the group consisting of H, $C_{1-10}$-alkyl, $C_{2-10}$-alkenyl, and $C_{2-10}$-alkynyl, and wherein, in $R^k$ and $R^1$, $C_{1-10}$-alkyl, $C_{2-10}$-alkenyl, and $C_{2-10}$-alkynyl are optionally substituted with one to five substituents selected from the group consisting of halogen, CN, and $NO_2$.

12. The polymer or compound of claim 11, wherein $L^2$ is selected from the group consisting of $C_{6-30}$-arylene and 5 to 30 membered heteroarylene, and

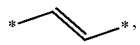

wherein $C_{6-30}$-arylene and 5 to 30 membered heteroarylene are optionally substituted with one to six substituents $R^3$ selected from the group consisting of $C_{1-30}$-alkyl, $C_{2-30}$-alkenyl, $C_{2-30}$-alkynyl, $C_{5-12}$-cycloalkyl, $C_{6-18}$-aryl, 5 to 20 membered heteroaryl, $OR^{31}$, $OC(O)-R^{31}$, $C(O)-OR^{31}$, $C(O)-R^{31}$, $NR^{31}R^{32}$, $NR^{31}-C(O)R^{32}$, $C(O)-NR^{31}R^{32}$, $SR^{31}$, halogen, CN, $SiR^{Siv}R^{Siw}R^{Six}$, and OH, and
wherein

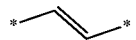

is optionally substituted with one or two substituents $R^4$ selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)R^{41}$, $C(O)-NR^{41}R^{42}$, $C(O)-OR^{41}$, and CN,
wherein $R^{31}$, $R^{32}$, $R^{41}$, and $R^{42}$ are each independently selected from the group consisting of H, $C_{1-30}$-alkyl, $C_{2-30}$-alkenyl, $C_{2-30}$-alkynyl, $C_{5-12}$-cycloalkyl, $C_{6-18}$-aryl, and 5 to 20 membered heteroaryl,
wherein, $R^{31}$, $R^{32}$, $R^{41}$, and $R^{42}$, $C_{1-30}$-alkyl, $C_{2-30}$-alkenyl, and $C_{2-30}$-alkynyl are optionally substituted with one to ten substituents independently selected from the group consisting of $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^j$, $C(O)-NR^iR^j$, $N[C(O)R^i][C(O)R^j]$, $SR^i$, halogen, CN, $SiR^{Siv}R^{Siw}R^{Six}$, and $NO_2$; and at least two $CH_2$-groups, but not adjacent $CH_2$-groups of $C_{1-30}$-alkyl, $C_{2-30}$-alkenyl, and $C_{2-30}$-alkynyl are optionally replaced by O or S,
wherein, $R^{31}$, $R^{32}$, $R^{41}$, and $R^{42}$, $C_{5-12}$-cycloalkyl is optionally substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^j$, $C(O)-NR^iR^j$, $N[C(O)R^i]$, $[C(O)R^j]$, $SR^i$, halogen, CN, $SiR^{Siv}R^{Siw}R^{Six}$, and $NO_2$; and one or two $CH_2$-groups, but not adjacent $CH_2$-groups, of $C_{5-12}$-cycloalkyl are optionally replaced by O, S, OC(O), CO, $NR^i$, or $NR^i-CO$,
wherein, $R^{31}$, $R^{32}$, $R^{41}$, and $R^{42}$, $C_{6-18}$-aryl and 5 to 20 membered heteroaryl are optionally substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, $OC(O)-R^j$, $C(O)-OR^i$, $C(O)-R^i$, $NR^iR^j$, $NR^i-C(O)R^j$, $C(O)-NR^iR^j$, $N[C(O)R^i][C(O)R^j]$, $SR^i$, halogen, CN, $SiRs^{Siv}R^{Siw}R^{Six}$, and $NO_2$,
wherein $SiR^{Siv}R^{Siw}R^{Six}$ are each independently selected from the group consisting of H, $C_{1-20}$-alkyl, $C_{2-20}$-alkenyl, $C_{2-20}$-alkynyl, $C_{5-6}$-cycloalkyl, phenyl, and $O-Si(CH_3)_3$, and
wherein $R^i$ and $R^j$ are independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, wherein, in $R^i$ and $R^j$, $C_{1-20}$-alkyl, $C_{2-20}$-alkenyl and $C_{2-20}$-alkynyl are optionally substituted with one to five substituents selected from the group consisting of $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^l$, $NR^k-C(O)R^1$, $C(O)-NR^kR^1$, $N[C(O)R^k][C(O)R^1]$, $SR^k$, halogen, CN, and $NO_2$, wherein, in $R^i$ and $R^j$, $C_{5-8}$-cycloalkyl is optionally substituted with one to five substituents selected from the group consisting of $C_{1-10}$-alkyl, $C_{2-10}$-alkenyl, $C_{2-10}$alkynyl, $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^1$, $NR^k-C(O)R^1$, $C(O)-NR^kR^1$, $N[C(O)R^k][C(O)R^1]$, $SR^k$, halogen, CN, and $NO_2$, wherein, in $R^i$ and $R^j$, $C_{6-14}$-aryl, and 5 to 14 membered heteroaryl are optionally substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)-R^1$, $C(O)-OR^k$, $C(O)-R^k$, $NR^kR^1$, $NR^k-C(O)R^1$, $C(O)-NR^kR^1$, $N[C(O)R^k][C(O)R^1]$, $SR^k$, halogen, CN, and $NO_2$, wherein $R^k$ and $R^1$ are independently selected from the group consisting of H, $C_{1-10}$-alkyl, $C_{2-10}$-alkenyl, and $C_{2-10}$-alkynyl, and wherein, in $R^k$ and $R^1$, $C_{1-10}$-alkyl, $C_{2-10}$-alkenyl, and $C_{2-10}$-alkynyl are optionally substituted with one to five substituents selected from the group consisting of halogen, CN and $NO_2$.

13. The polymer or compound of claim 12, wherein $L^2$ is selected from the group consisting of $C_{6-30}$-arylene and 5 to 30 membered heteroarylene, and

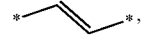

wherein $C_{6-30}$-arylene and 5 to 30 membered heteroarylene is selected from the group consisting of

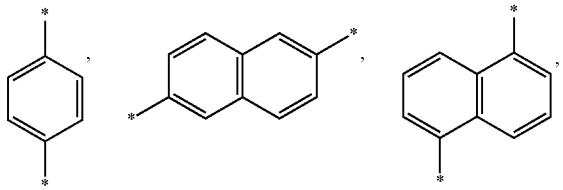

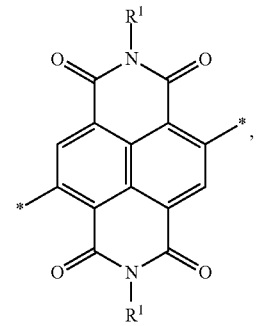

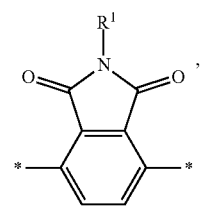

85
-continued
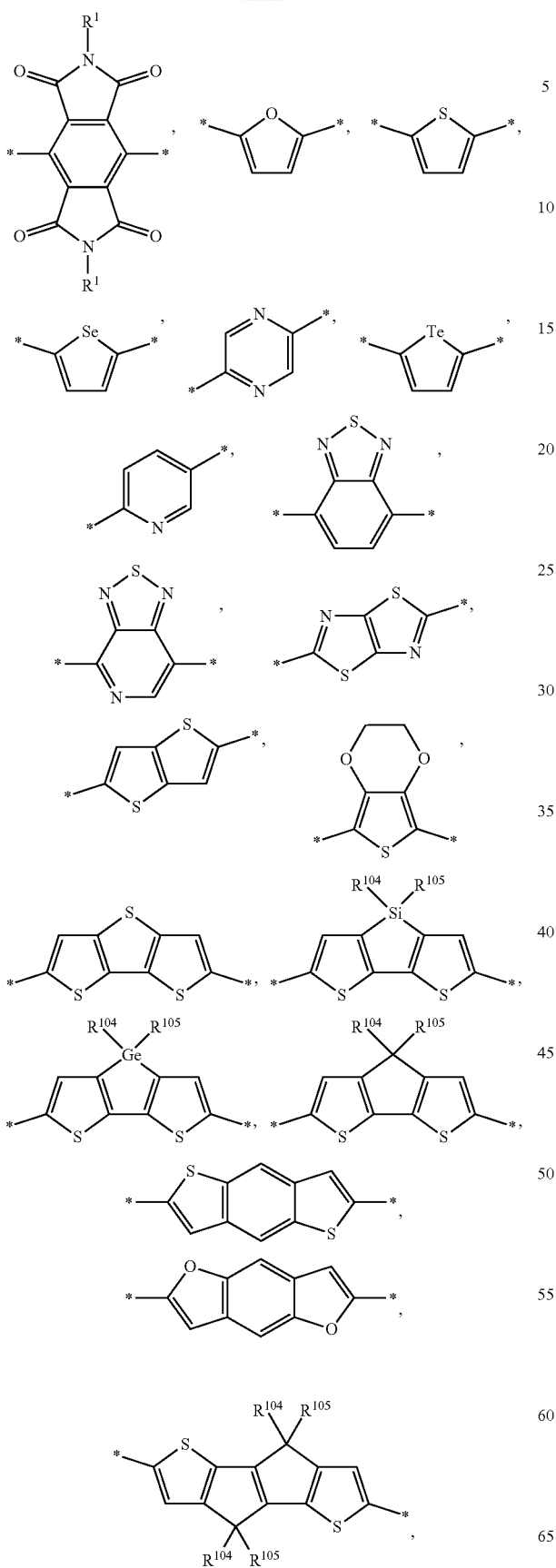
86
-continued
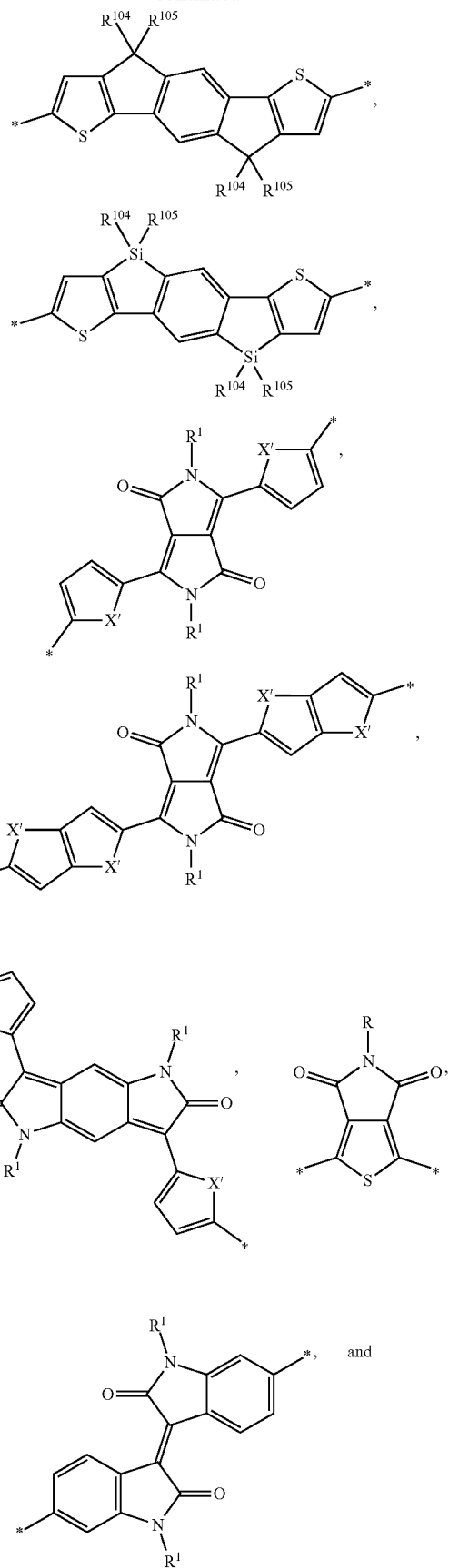

-continued

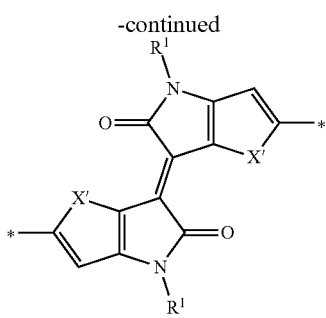

wherein R¹ is selected from the group consisting of $C_{1-36}$-alkyl, $C_{3-36}$-alkenyl, and $C_{3-36}$-alkynyl, wherein $C_{1-36}$-alkyl, $C_{3-36}$-alkenyl and $C_{3-36}$-alkynyl are optionally substituted with one to twenty substituents independently selected from the group consisting of $C_{5-6}$-cycloalkyl, $C_{6-10}$-aryl, 5 to 10 membered heteroaryl, $OR^a$, $SR^a$, $Si(R^{Sia})(R^{Sib})(R^{Sic})$, —O—$Si(R^{Sia})(R^{Sib})(R^{Sic})$, halogen, and CN; and at least two $CH_2$-groups, but not adjacent $CH_2$-groups, of $C_{1-36}$-alkyl, $C_{2-36}$-alkenyl, and $C_{2-36}$-alkynyl are optionally replaced by O or S, wherein $R^a$ is independently selected from the group consisting of H, $C_{3-20}$-alkenyl, $C_{3-20}$-alkynyl, $C_{5-6}$-cycloalkyl, and $C_{6-10}$-aryl, wherein $R^{Soa}$, $R^{Sib}$ and $R^{Sic}$ are independently selected from the group consisting of H, $C_{1-20}$-alkyl, $C_{2-20}$-alkenyl, $C_{2-20}$-alkynyl, $C_{5-6}$-cycloalkyl, $C_{6-10}$-aryl, and -[O-$SiR^{Sid}R^{Sie}]_o$—$R^{Sif}$ wherein o is an integer from 1 to 50, wherein $R^{Sid}$, $R^{Sie}$, $R^{Sif}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, and —[O-$SiR^{Sig}R^{Sih}]p$—$R^{Sii}$, wherein p is an integer from 1 to 50, wherein $R^{Sig}$ $R^{Sih}$, $R^{Sii}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, and O-Si($CH_3)_3$, $C_{1-20}$-alkyl, $C_{2-20}$-alkenyl, and $C_{2-20}$-alkynyl are optionally substituted with one to ten substituents selected from the group consisting of halogen and CN, wherein $R^{104}$ and $R^{105}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{104}$ and $R^{105}$, if attached to the same atom, together with the atom, to which they are attached, form a 5 to 12 membered ring system, wherein, in $R^{104}$ and $R^{105}$, $C_{1-20}$-alkyl, $C_{2-20}$-alkenyl, and $C_{2-20}$-alkynyl are optionally substituted with one to five substituents selected from the group consisting of $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, wherein, in $R^{104}$ and $R^{105}$, $C_{5-8}$-cycloalkyl is optionally substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, wherein, in $R^{104}$ and $R^{105}$, $C_{6-14}$-aryl and 5 to 14 membered heteroaryl are optionally substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, wherein, in $R^{104}$ and $R^{105}$, 5 to 12 membered ring system is optionally substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, wherein $R^s$ and $R^t$ are independently selected from the group consisting of H, $C_{1-10}$-alkyl, $C_{2-10}$-alkenyl, and $C_{2-10}$-alkynyl, wherein, in $R^s$ and $R^t$, $C_{1-10}$-alkyl, $C_{2-10}$-alkenyl and $C_{2-10}$-alkynyl are optionally substituted with one to five substituents selected from the group consisting of halogen, CN, and $NO_2$, wherein $C_{6-30}$-arylene and 5 to 30 membered heteroarylene are optionally substituted with one to six substituents $R^3$ at each occurrence selected from the group consisting of $C_{1-30}$-alkyl and halogen, wherein

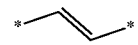

is optionally substituted with one or two substituents $R^4$ selected from the group consisting of $C_{1-30}$-alkyl, $C(O)$—$R^{41}$, $C(O)$—$OR^{41}$ and CN, and wherein $R^{41}$ is at each occurrence $C_{1-30}$-alkyl.

14. The polymer or compound of claim 13, wherein $L^2$ is selected from a group consisting of

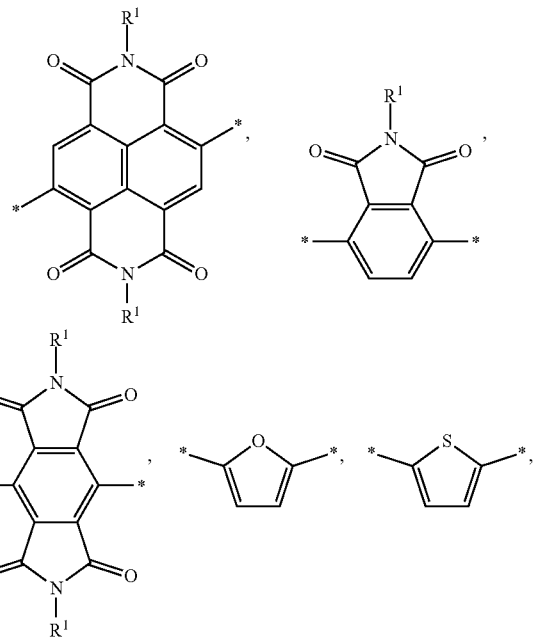

-continued
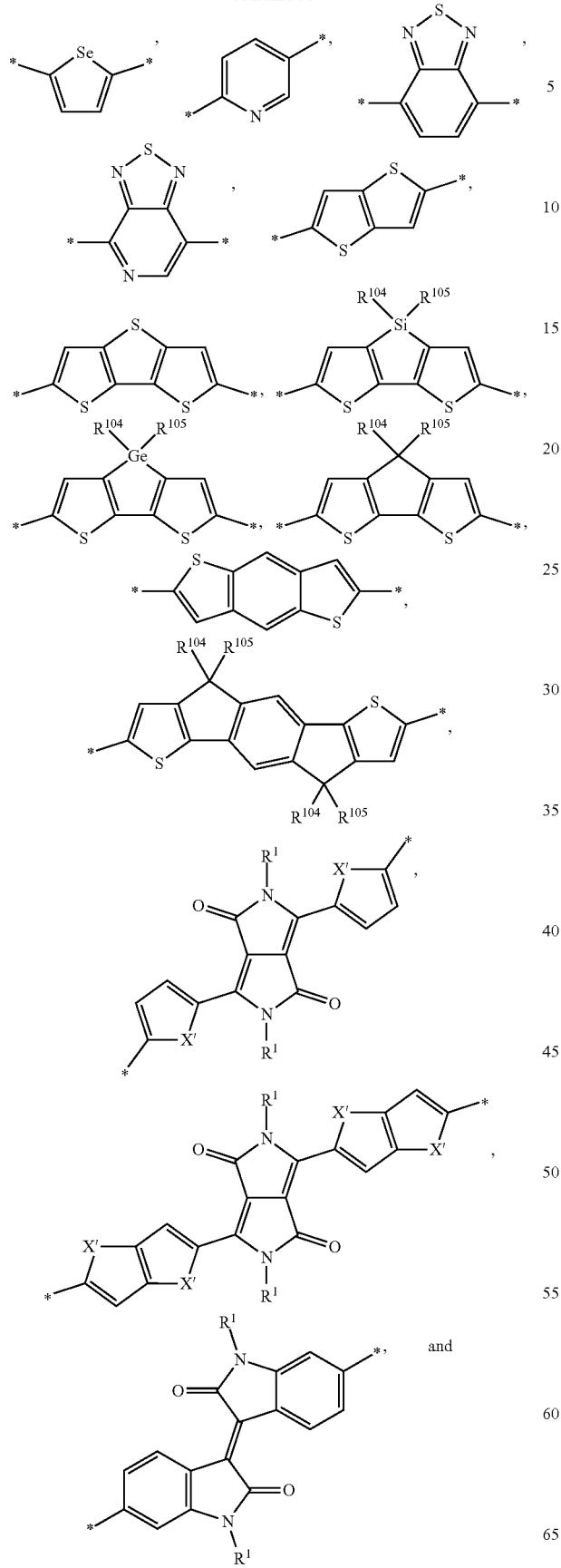
-continued
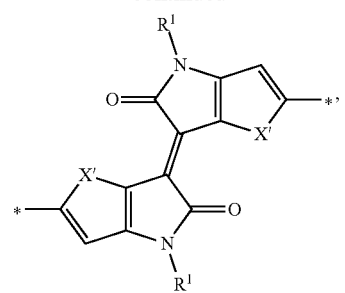
wherein $L^1$ and $L^2$ are not further substituted.
15. The polymer or compound of claim 11, wherein $L^2$ is selected from
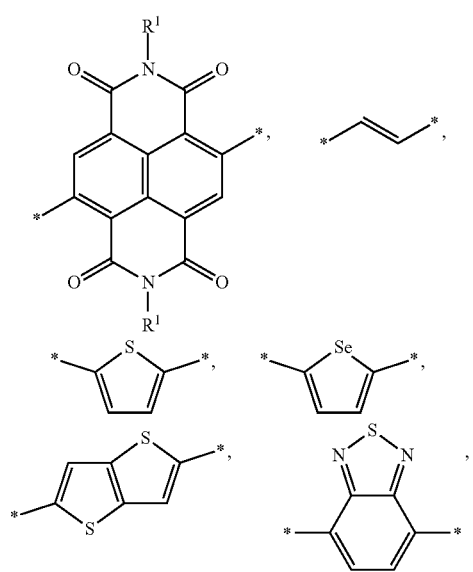
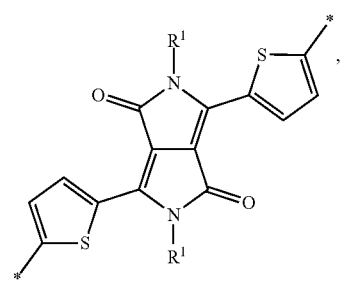
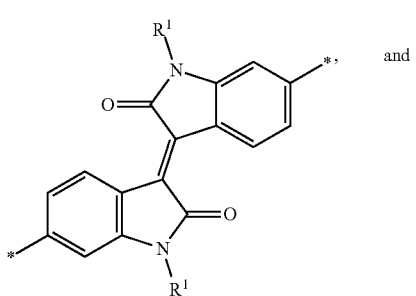

-continued
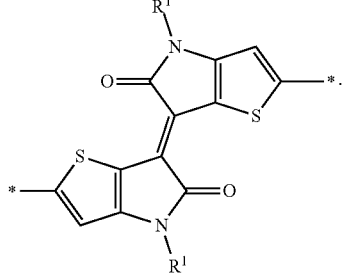
16. The polymer or compound of claim 11, wherein:
n is 1, or 2; and
m is 0, 1, or 2.
17. An electronic device, comprising the polymer or compound of claim 11.
18. The electronic device of claim 11, wherein the electronic device is an organic field effect transistor.
19. The polymer or compound of claim 11, wherein $L_1$ comprises:
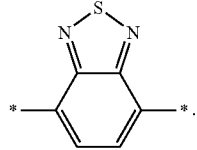
20. The polymer or compound of claim 11, wherein $L_1$ comprises:
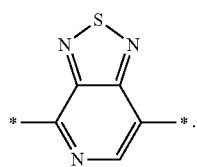
* * * * *